United States Patent
Gleeson et al.

(10) Patent No.: US 10,767,227 B2
(45) Date of Patent: *Sep. 8, 2020

(54) COMPOSITIONS AND METHODS FOR DETERMINING GENETIC POLYMORPHISMS IN THE TMEM216 GENE

(71) Applicant: The Regents of the University of California, Oakland, CA (US)

(72) Inventors: Joseph G. Gleeson, San Diego, CA (US); Jennifer Silhavy, San Diego, CA (US); Enza Maria Valente, Rome (IT); Francesco Brancati, Rome (IT)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/839,096

(22) Filed: Dec. 12, 2017

(65) Prior Publication Data
US 2018/0195126 A1 Jul. 12, 2018
Related U.S. Application Data

(63) Continuation of application No. 14/079,397, filed on Nov. 13, 2013, now Pat. No. 9,879,322, which is a continuation of application No. 13/098,345, filed on Apr. 29, 2011, now Pat. No. 8,614,094.

(51) Int. Cl.
| | |
|---|---|
| C12Q 1/6883 | (2018.01) |
| G01N 33/68 | (2006.01) |
| C07K 16/28 | (2006.01) |
| C07K 14/47 | (2006.01) |

(52) U.S. Cl.
CPC ............ *C12Q 1/6883* (2013.01); *C07K 14/47* (2013.01); *C07K 16/28* (2013.01); *G01N 33/6893* (2013.01); *G01N 33/6896* (2013.01); *A01K 2207/05* (2013.01); *A01K 2217/054* (2013.01); *A01K 2227/40* (2013.01); *C12Q 2600/156* (2013.01); *G01N 2500/04* (2013.01); *G01N 2800/28* (2013.01); *G01N 2800/50* (2013.01); *Y10T 436/105831* (2015.01)

(58) Field of Classification Search
None
See application file for complete search history.

(56) References Cited

U.S. PATENT DOCUMENTS

| | | |
|---|---|---|
| 8,119,351 B2 | 2/2012 | Vincent et al. |
| 2009/0299645 A1 | 12/2009 | Colby et al. |
| 2010/0196898 A1 | 8/2010 | Sugarbaker et al. |
| 2010/0297636 A1 | 11/2010 | Vicente et al. |

FOREIGN PATENT DOCUMENTS

WO    0198353 A2    12/2001

OTHER PUBLICATIONS

*Homo sapiens* transmembrane protein 216 (TMEM216), transcript variant 1, mRNA, NCBI Reference Sequence: NM_016499.5, Jan. 2010, p. 1-3 (Year: 2010).*

*Homo sapiens* transmembrane protein 216 (TMEM216), transcript variant 2, mRNA, NCBI Reference Sequence: NM_001173990.2, Mar. 2015, p. 1-4 (Year: 2015).*

*Homo sapiens* transmembrane protein 216 (TMEM216), transcript variant 3, mRNA, NCBI Reference Sequence: NM_001173991.2, May 2014, p. 1-4 (Year: 2014).*

Edvardson, S., et al. (201 0) "Joubert syndrome 2 (JBTS2) in Ashkenazi Jews is associated with a TMEM216 mutation". Am. J. Hum. Genet. 86 (1 ); 93-7; Epub Dec. 31, 2009.

Valente, et al. (201 0) "Mutations in TMEM216 perturb ciliogenesis and cause Joubert, Meckel and related syndromes". Nat Genet. Jul. 2010; 42(7): 619-625.

Iannicelli, et al. (201 0) "Novel TMEM67 mutations and genotype-phenotype correlates in meckelin-related ciliopathies". Hum Mutat. May 2010;31 (5):E1319-31.

Louie, et al. (2005) "Genetic basis of Joubert syndrome and related disorders of cerebellar development". Hum Mol Genet. Oct. 15, 2005;14 Spec No. 2:R235-42.

Valente, et al. (2005) "Distinguishing the four genetic causes of Jouberts syndrome-related disorders". Ann Neural. Apr. 2005;57(4):513-9.

Wang, A. (Epub 201 0) "TMEM216 joins its ciliary cousins in ciliopathies". Clin Genet. Jan. 2011;79(1 ):45-7. Epub Oct. 12, 2010.

Otto, et al. (Epub 201 0) Mutation analysis of 18 nephronophthisis associated ciliopathy disease genes . . . . J Med Genet. Feb. 2011;48(2):105-16. Epub Nov. 10, 2010.

Logan, et al. (Epub 201 0) "Molecular genetics and pathogenic mechanisms for the severe ciliopathies . . . ".Mol Neurobiol. Feb. 2011;43(1):12-26. Epub Nov. 27, 2010.

Sardana et al., Office Action for Canadian Patent Application CA 2,741,110, dated Mar. 29, 2019.

* cited by examiner

*Primary Examiner* — Christopher M Babic
*Assistant Examiner* — Arthur S Leonard
(74) *Attorney, Agent, or Firm* — Greer, Burns & Crain, Ltd.; Gregory P. Einhorn

(57) ABSTRACT

In alternative embodiments, the invention provides nucleic acid sequences that are genetic polymorphic variations of the human TMEM216 gene, and TMEM216 polypeptide encoded by these variant alleles. In alternative embodiments, the invention provides methods of determining or predicting a predisposition to, or the presence of, a ciliopathy (or any genetic disorder of a cellular cilia or cilia anchoring structure, basal body or ciliary function) in an individual, such as a Joubert Syndrome (JS), a Joubert Syndrome Related Disorder (JSRD) or a Meckel Syndrome (MKS). In alternative embodiments, the invention provides compositions and methods for the identification of genetic polymorphic variations in the human TMEM216 gene, and methods of using the identified genetic polymorphisms and the proteins they encode, e.g., to screen for compounds that can modulate the human TMEM216 gene product, and possibly treat JS, JSRD or MKS. In alternative embodiments, the invention provides cells, cell lines and/or non-human transgenic animals that can be used as screening or model systems for studying ciliopathies and testing various therapeutic approaches in treating ciliopathies, e.g., JS, JSRD or MKS.

11 Claims, 42 Drawing Sheets
(20 of 42 Drawing Sheet(s) Filed in Color)
Specification includes a Sequence Listing.

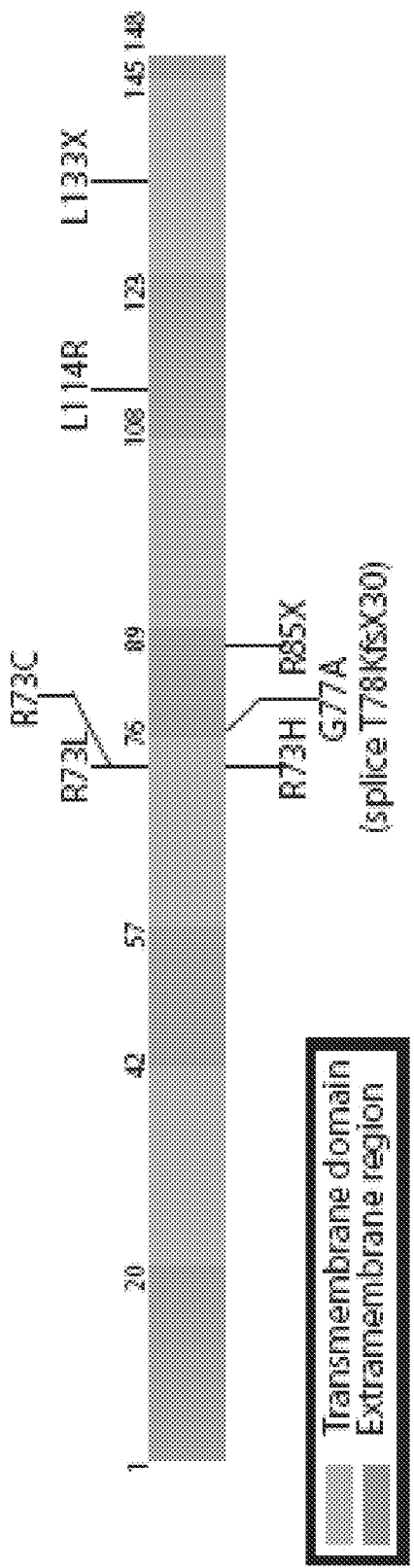
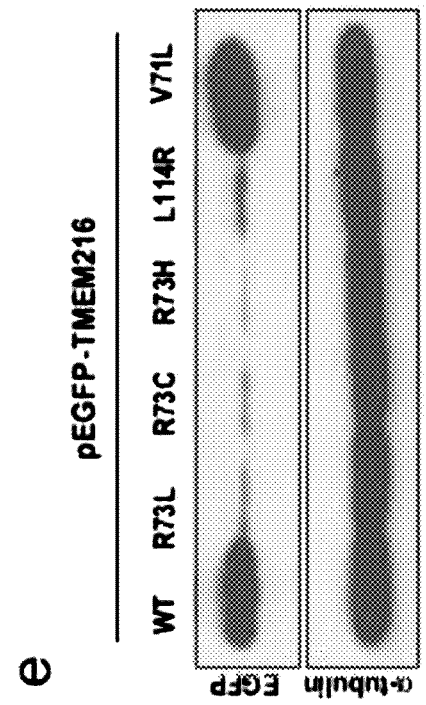
FIG. 1C
FIG. 1D
FIG. 1E

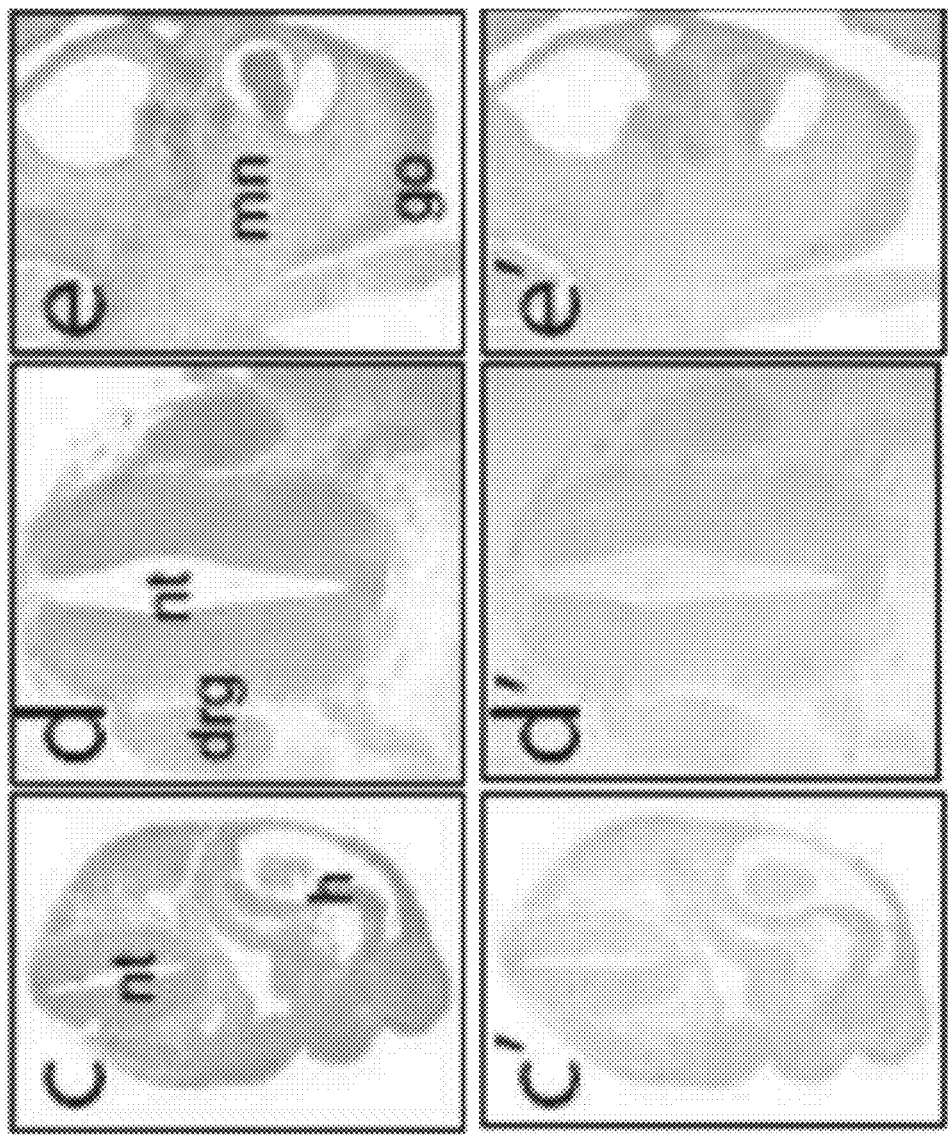

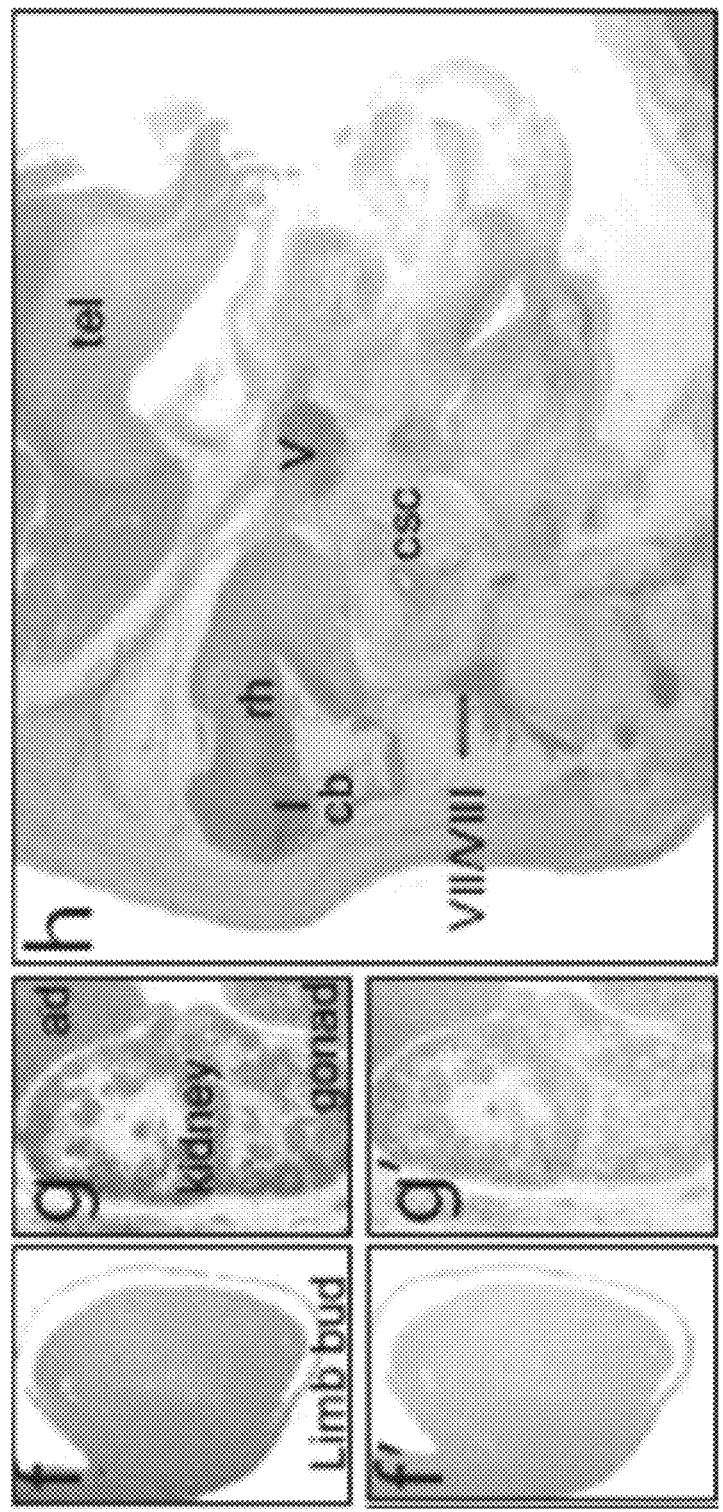

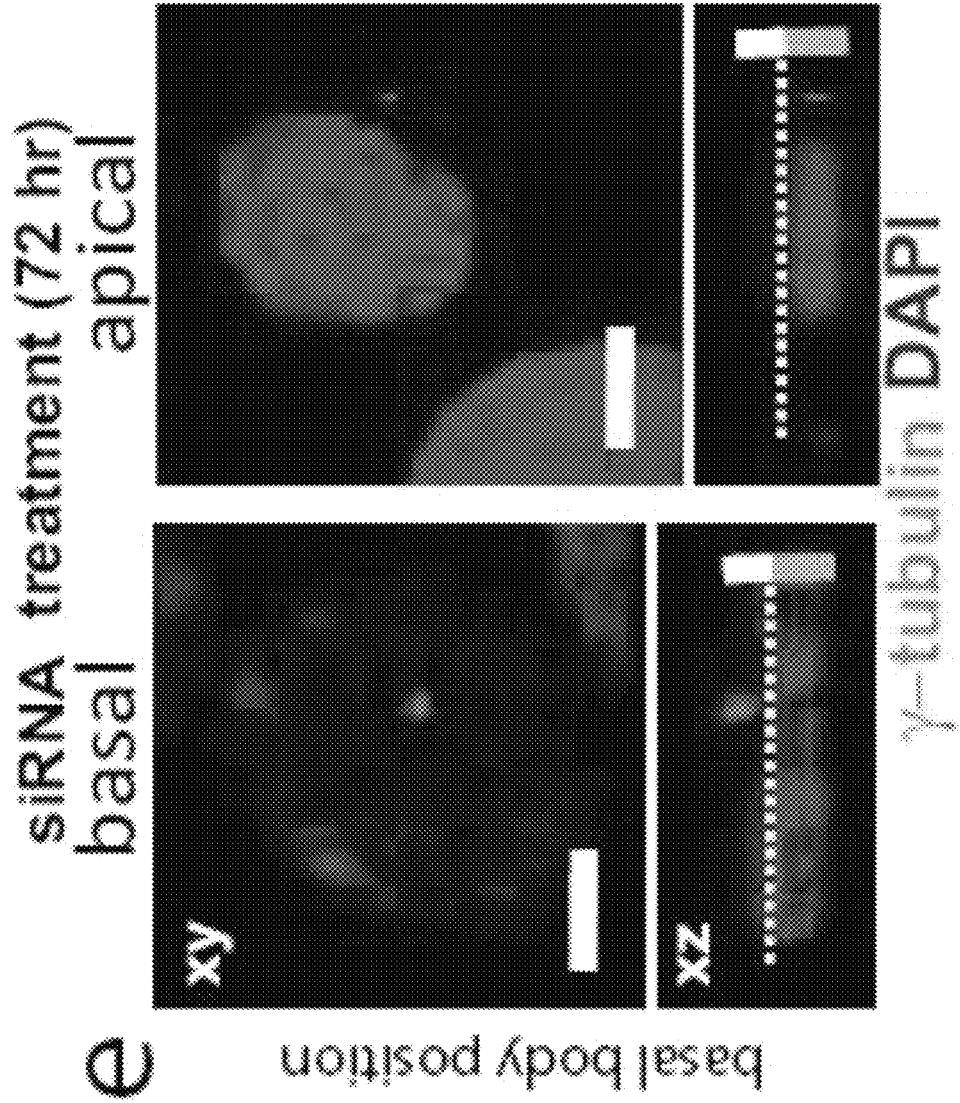

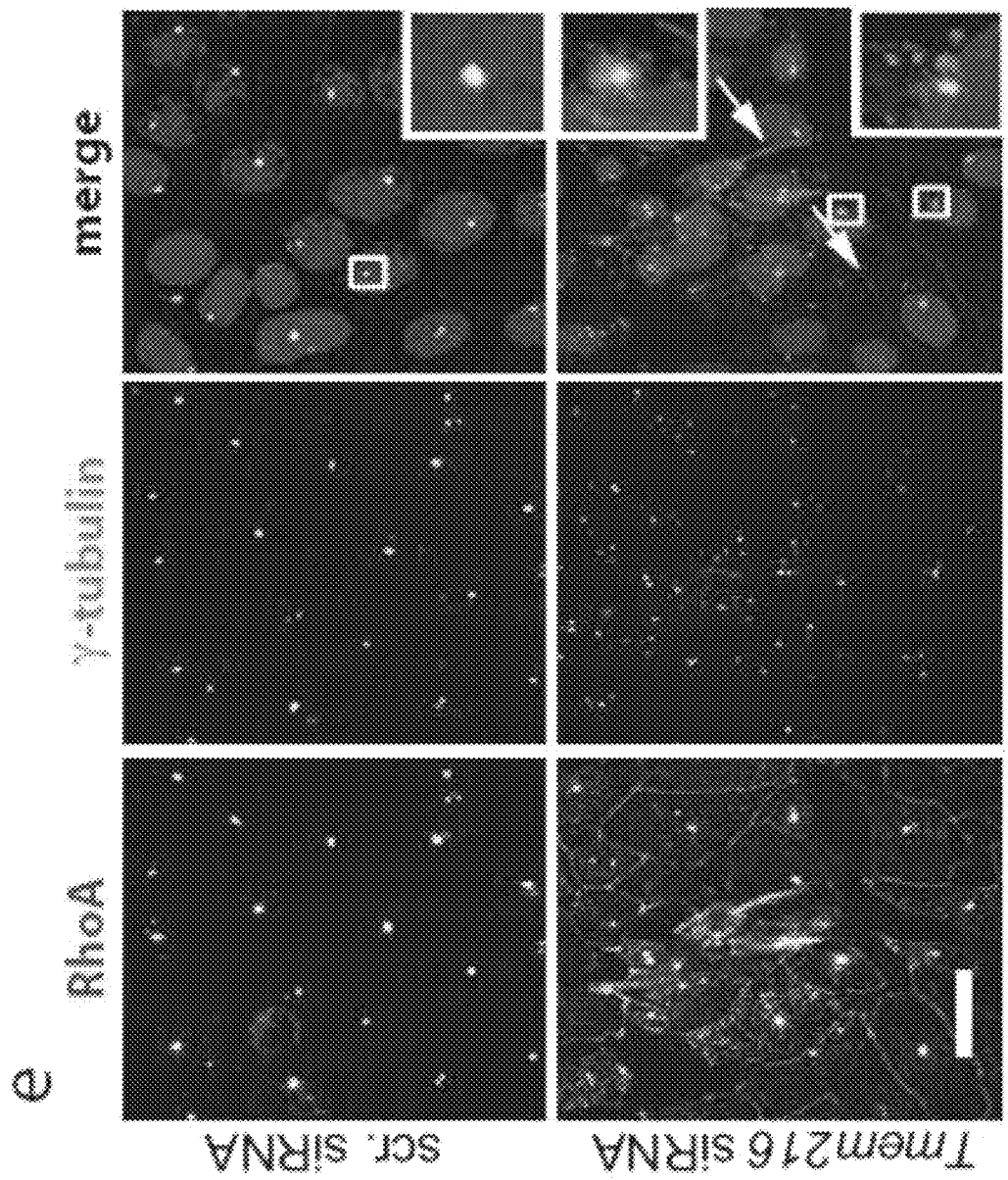

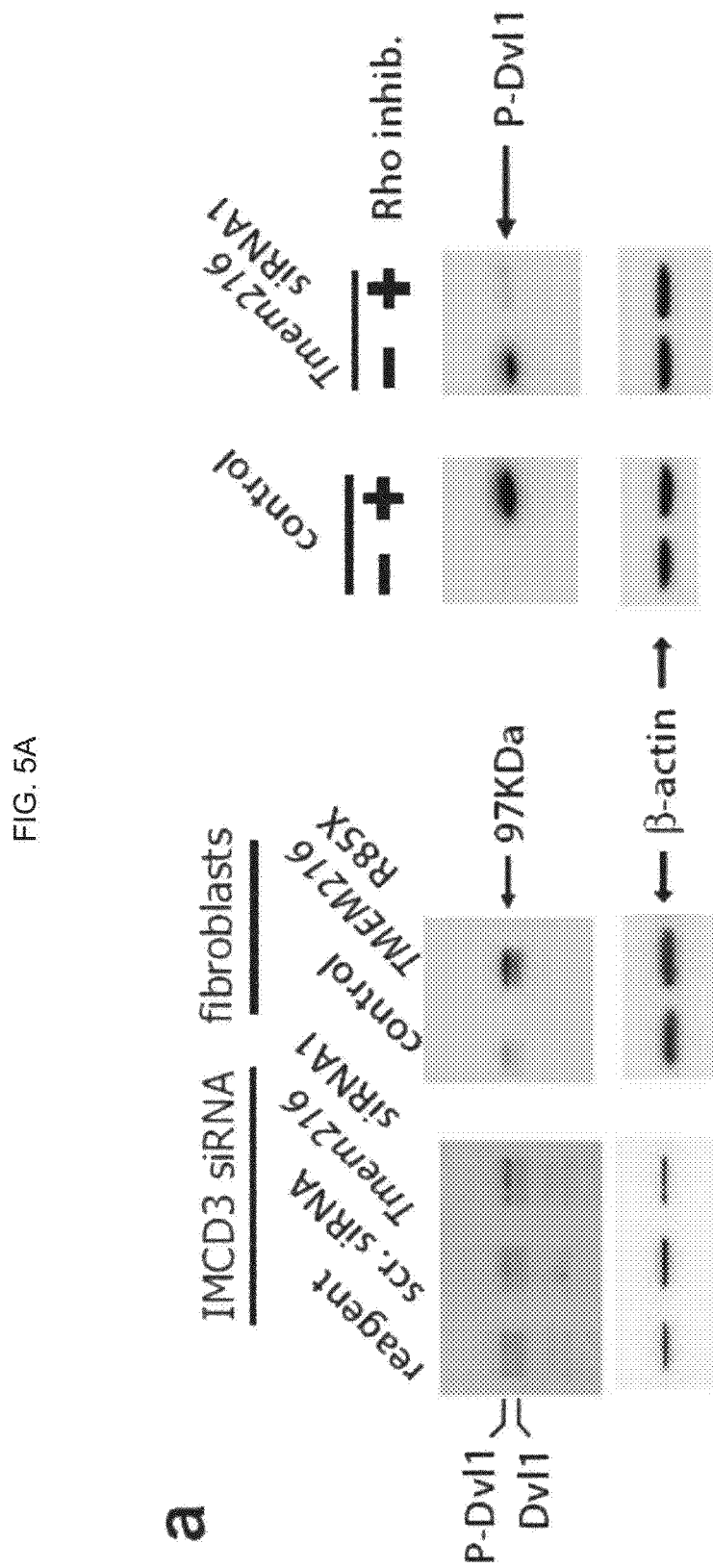

| | MKS15 | MKS16 | MKS74 | MKS860 | MKS350 | MKS492 | MKS512 |
|---|---|---|---|---|---|---|---|
| rs1113480 48.014 | AB | AB | BB | AA | AA | AA | AA |
| rs1503174 48.202 | BB | BB | BB | BB | AA | AA | BB |
| rs717897 48.332 | BB | BB | BB | BB | BB | BB | BB |
| rs2202632 48.704 | AA | AA | AA | BB | AA | BB | BB |
| rs1880438 49.327 | AA | AA | AA | AA | BB | AA | AA |
| rs847635 49.879 | BB | BB | BB | AA | AA | AA | AA |
| rs1817952 50.096 | AA | AA | AA | AA | BB | AA | AA |
| rs1390678 50.096 | AA | AA | AA | BB | BB | BB | BB |
| rs1546170 50.123 | AA | AA | AA | BB | BB | BB | BB |
| rs2204184 50.418 | BB | BB | BB | AA | BB | AA | AA |
| rs1916207 50.418 | BB | BB | BB | BB | BB | BB | BB |
| rs2216281 50.595 | BB | BB | BB | BB | AA | BB | BB |
| rs7478983 51.247 | BB | BB | BB | BB | BB | BB | BB |
| rs508823 51.302 | BB | BB | BB | AA | BB | AA | AA |
| rs507015 51.303 | BB | BB | BB | BB | BB | BB | BB |
| rs521874 51.319 | BB | BB | BB | AA | BB | AA | AA |
| rs1531762 55.544 | AA | AA | AA | AA | AA | AA | AA |
| rs1945222 55.923 | AA | AA | AA | AA | BB | AA | AA |
| rs594854 56.007 | AA | AA | AA | AA | BB | AA | AA |
| rs518385 56.301 | BB | BB | BB | AA | AA | AA | AA |
| rs1943625 56.349 | BB | BB | BB | AA | AA | AA | AA |
| rs544549 56.371 | AA | AA | AA | BB | BB | BB | BB |
| rs1938754 56.430 | AA | AA | AA | AA | AA | AA | AA |
| rs1793429 56.453 | BB | BB | BB | BB | BB | BB | BB |
| rs1792525 56.473 | BB | BB | BB | BB | BB | BB | BB |
| rs950120 56.547 | BB | BB | BB | BB | BB | BB | BB |
| rs3887125 56.906 | BB | BB | BB | BB | BB | BB | BB |
| rs1376486 57.713 | BB | BB | BB | BB | BB | BB | BB |
| rs1376485 57.713 | BB | BB | BB | BB | BB | BB | BB |
| rs2867404 57.713 | BB | BB | BB | BB | BB | BB | BB |
| rs1938653 57.769 | AA | AA | AA | AA | AA | AA | AA |
| rs1986404 57.951 | BB | BB | BB | AA | AA | AA | AA |
| rs1943280 58.368 | AA | AA | AA | AA | AA | AA | AA |
| rs1943281 58.368 | BB | BB | BB | BB | BB | BB | BB |
| rs1943282 58.368 | AA | AA | AA | AA | AA | AA | AA |
| rs1939546 59.505 | BB | BB | BB | AA | AA | BB | BB |
| rs525064 59.522 | BB | BB | BB | BB | AA | BB | BB |
| rs595014 59.734 | AA | AA | AA | BB | BB | BB | BB |
| rs603648 59.769 | BB | BB | BB | BB | BB | BB | BB |
| rs1593480 59.818 | BB | BB | BB | AA | BB | BB | BB |
| rs950803 59.909 | AA | AA | AA | BB | BB | BB | BB |
| rs1080719 60.179 | BB | BB | BB | BB | BB | BB | BB |
| rs522073 60.635 | BB | BB | BB | BB | BB | AA | AA |
| rs1377456 60.971 | BB | BB | BB | AA | AA | BB | BB |
| rs720868 60.971 | AA | AA | AA | BB | BB | AA | AA |
| rs720891 60.972 | BB | BB | BB | AA | AA | BB | BB |
| rs953169 61.840 | BB | BB | BB | BB | AA | AB | AB |
| rs953894 62.518 | AB | AB | BB | AA | BB | AA | AA |

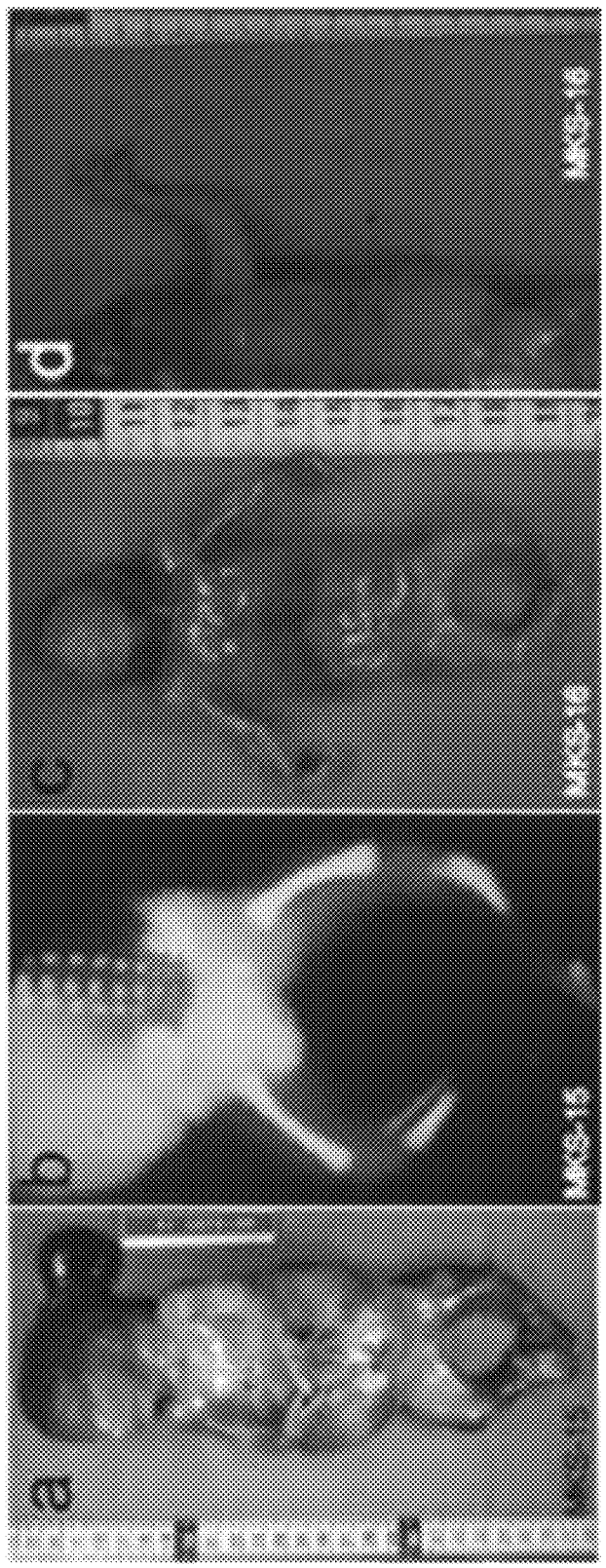

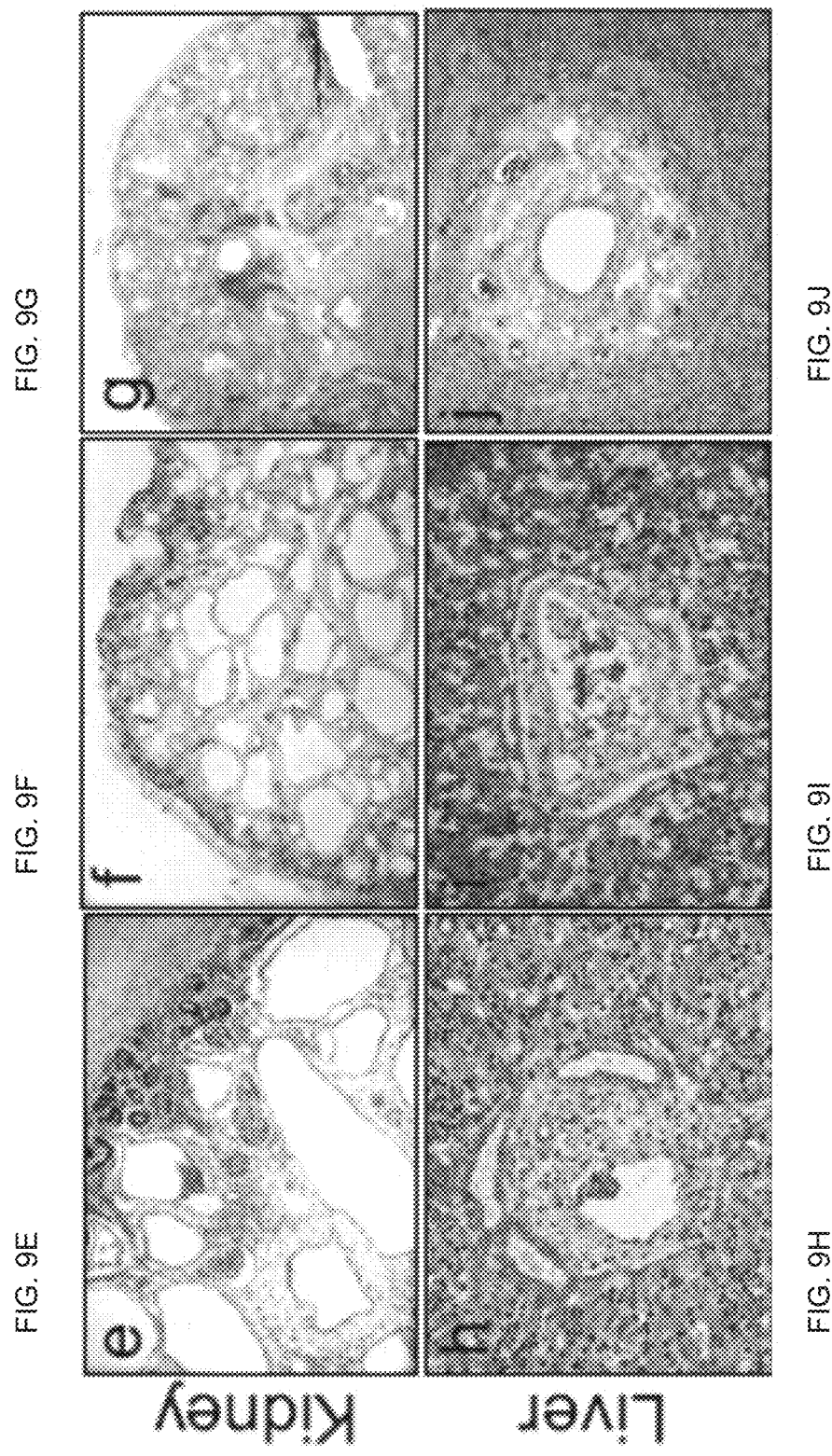

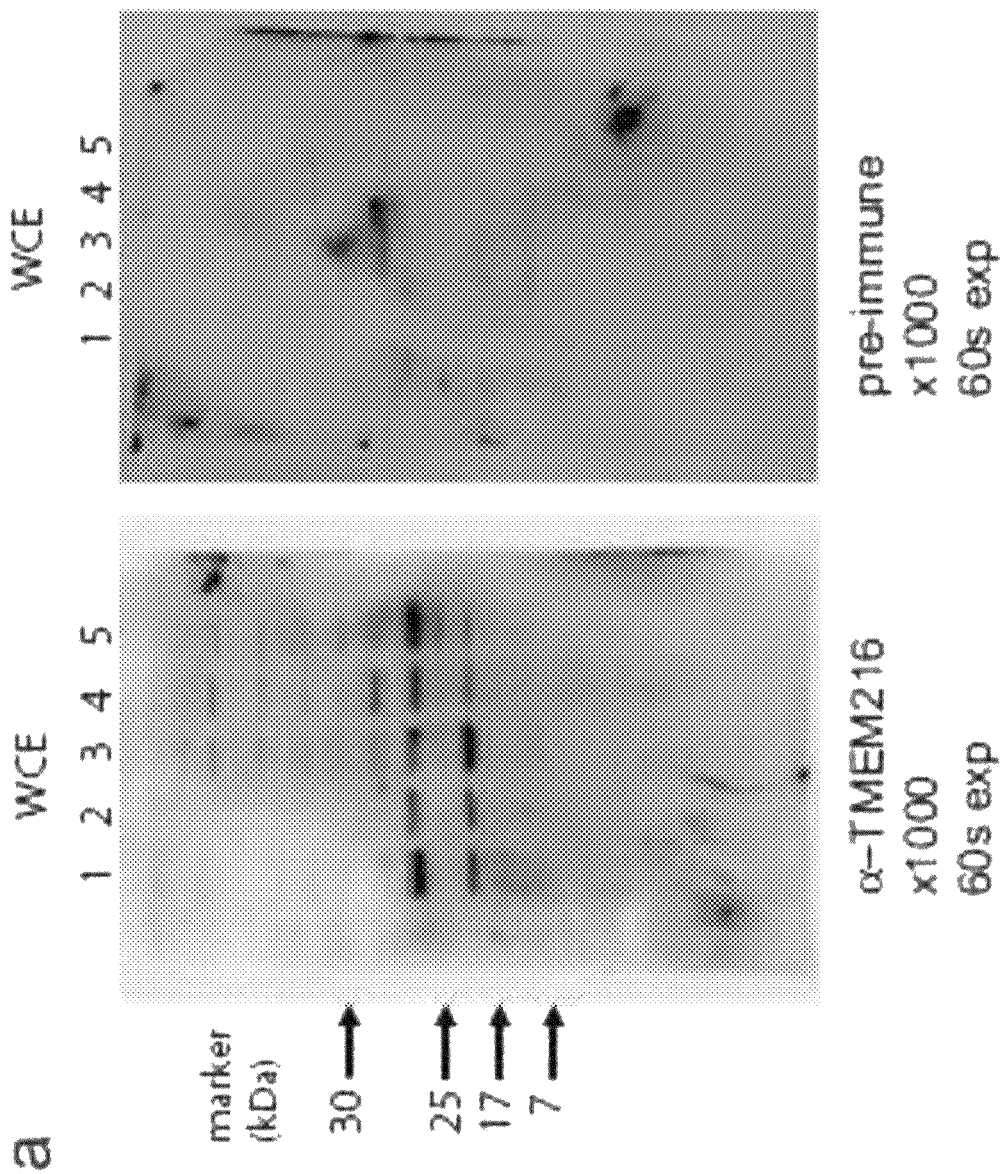

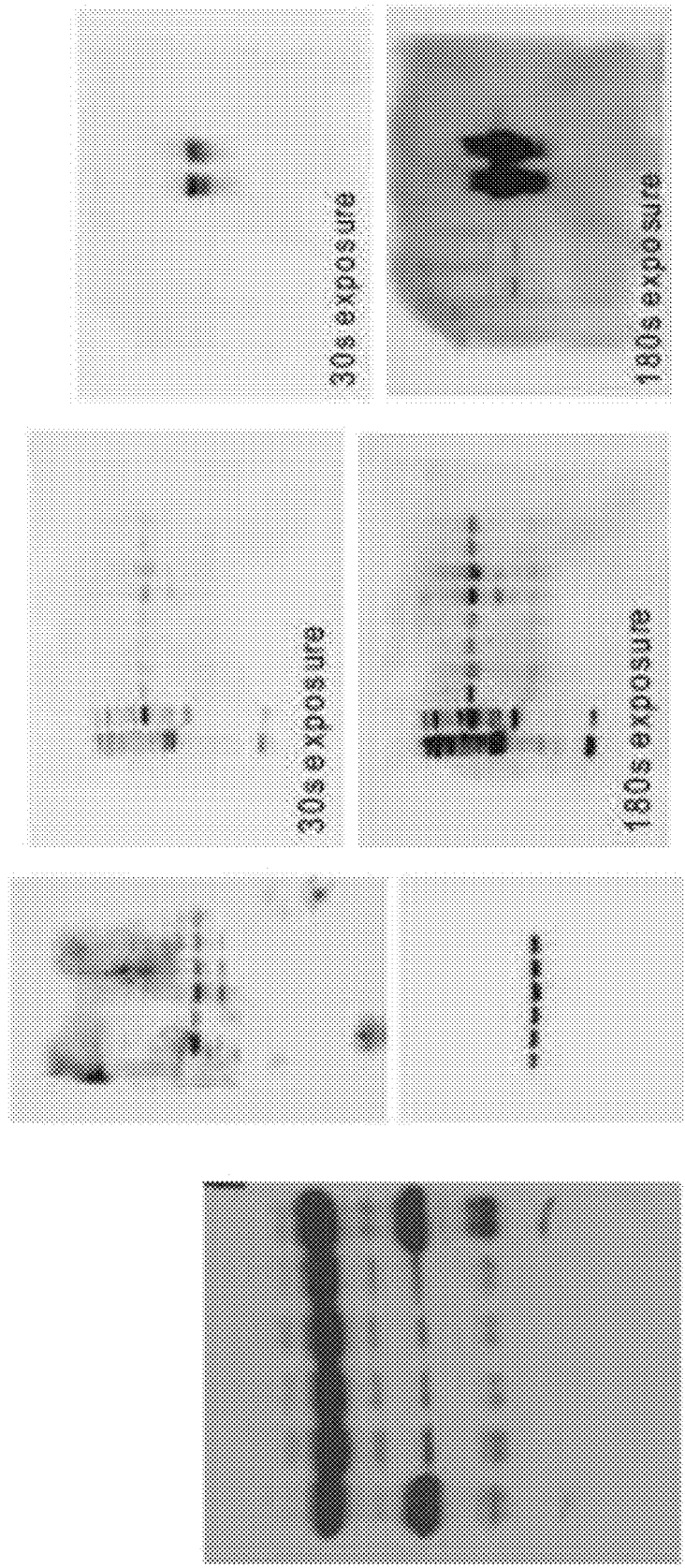

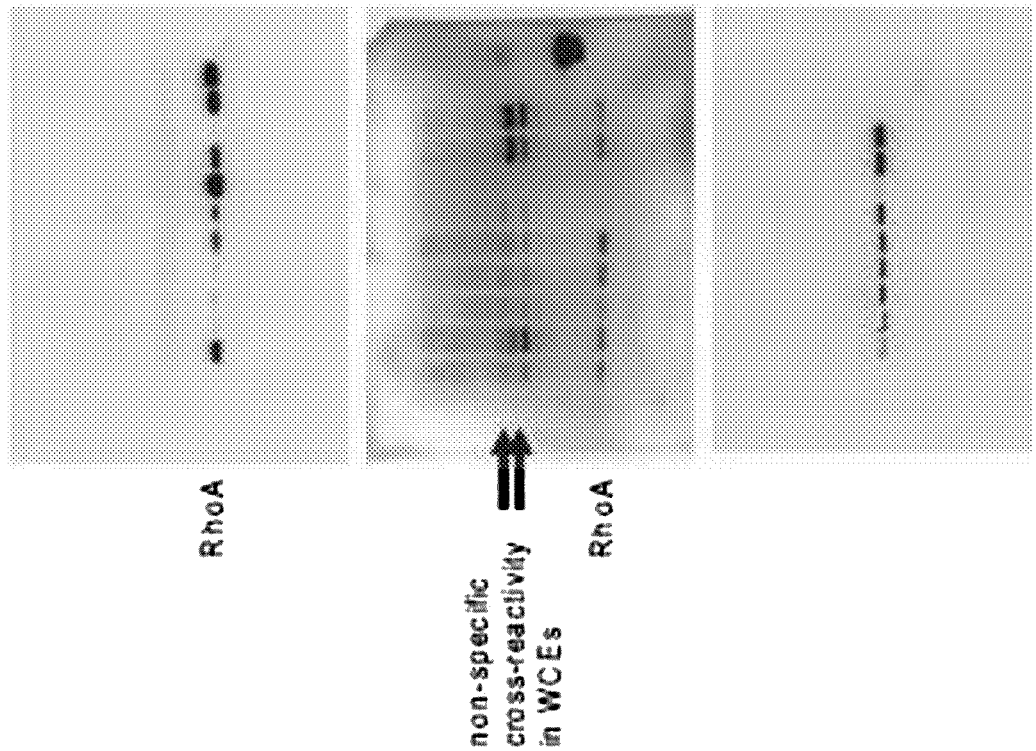
FIG. 15G
FIG. 15F
FIG. 15E
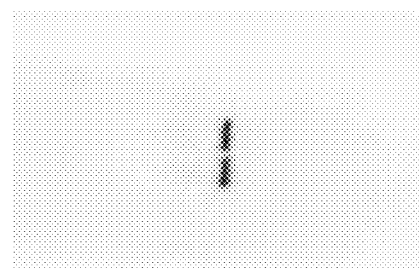
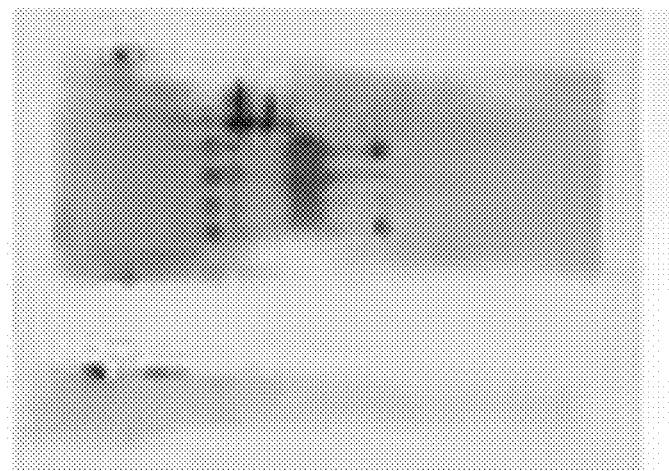

SEQUENCE LISTING

<160> NUMBER OF SEQ ID NOS: 47

<210> SEQ ID NO 1
<211> LENGTH: 148

<212> TYPE: PRT
<213> ORGANISM: Homo sapiens

<400> SEQUENCE: 1

Met Leu Pro Arg Gly Leu Lys Met Ala Pro Arg Gly Lys Arg Leu Ser
1               5                   10                  15

Ser Thr Pro Leu Glu Ile Leu Phe Phe Leu Asn Gly Trp Tyr Asn Ala
            20                  25                  30

Thr Tyr Phe Leu Leu Glu Leu Phe Ile Phe Leu Tyr Lys Gly Val Leu
        35                  40                  45

Leu Pro Tyr Pro Thr Ala Asn Leu Val Leu Asp Val Val Met Leu Leu
    50                  55                  60

Leu Tyr Leu Gly Ile Glu Val Ile Arg Leu Phe Phe Gly Thr Lys Gly
65                  70                  75                  80

Asn Leu Cys Gln Arg Lys Met Pro Leu Ser Ile Ser Val Ala Leu Thr
                85                  90                  95

Phe Pro Ser Ala Met Met Ala Ser Tyr Tyr Leu Leu Leu Gln Thr Tyr
            100                 105                 110

Val Leu Arg Leu Glu Ala Ile Met Asn Gly Ile Leu Leu Phe Phe Cys
        115                 120                 125

Gly Ser Glu Leu Leu Leu Glu Val Leu Thr Leu Ala Ala Phe Ser Ser
130                 135                 140

Met Asp Thr Ile
145

<210> SEQ ID NO 2
<211> LENGTH: 862
<212> TYPE: DNA
<213> ORGANISM: Homo sapiens

<400> SEQUENCE: 2
ctgcagacga cggcgtcgtg ggtggtcacc gttatcccct aggtctggag aggggacatc      60
cgagcgaggg ccacttgcgg ccaggcccga gctcgtccag ctccgggtga ccacagagtg     120
ccgcgggcgg gcagaggggc cggaaaccca ggccgcttcg tccctgtttc ggcagcgcc      180
gcgctgctcc gggagccgct gtggcagcgt atgctgccac ggggactgaa gatggcgccg     240
cgaggtaaac ggttgtcctc caccccgctg aaaatcctgt tctttctgaa cgggtggtat     300
aatgctacct atttcctgct ggaacttttc atatttctgt ataaaggtgt cctgctacca     360
tatccaacag ctaacctagt actggatgtg gtgatgctcc tcctttatct tggaattgaa     420
gtaattcgcc tgttttttgg tacaaaggga aacctctgcc agcgaaagat gccactcagt     480
attagcgtgg ccttgacctt cccatctgcc atgatggcct cctattacct gctgctgcag     540
acctacgtac tccgcctgga agccatcatg aatggcatct gctcttcttc ctgtggctca     600
gagcttttac ttgaggtgct caccttggct gctttctcca gtatggacac gatttgaagt     660
acagaatttc agccagcagc ccatcaggct gacaccacac atattgcttc tggtacttta     720
gccacaccag tgagaattgg tggggcaagt tgtcctgaga aaggctgtgt ggcttttctt     780
cagcacagac ctttgggcaa ggcaactcag cataaggccg tgggtaccat cttctaaaac     840
caggaccatc caggccaaga ga                                             862

<210> SEQ ID NO 3
<211> LENGTH: 447
<212> TYPE: DNA
<213> ORGANISM: Homo sapiens

<400> SEQUENCE: 3

```
atgctgccac ggggactgaa gatggcgccg cgaggtaaac ggttgtcctc cacccgctg      60
gaaatcctgt tctttctgaa cgggtggtat aatgctacct atttcctgct ggaacttttc   120
atatttctgt ataaaggtgt cctgctacca tatccaacag ctaacctagt actggatgtg   180
gtgatgctcc tcctttatct tggaattgaa gtaattcgcc tgttttttgg tacaaaggga   240
aacctctgcc agcgaaagat gccactcagt attagcgtgg ccttgacctt cccatctgcc   300
atgatggcct cctattacct gctgctgcag acctacgtac tccgcctgga agccatcatg   360
aatggcatct tgctcttctt ctgtggctca gagcttttac ttgaggtgct caccttggct   420
gctttctcca gtatggacac gatttga                                        447
```

<210> SEQ ID NO 4
<211> LENGTH: 1188
<212> TYPE: DNA
<213> ORGANISM: Homo sapiens

<400> SEQUENCE: 4

```
gtgggtggtc accgttatcc cttaggtctg gagaggggac atccgagcga gggccacttg    60
cggccaggcc cgagctcgtc cagctcccgg tgaccacaga gtgccgcggg cgggcagagg   120
ggccggaaac ccaggccgct tcgtccctgt ttccggcagc gccgcgctgc tccgggagcc   180
gctgtggcag cgtatgctgc cacggggact gaagatggcg ccgcgaggtg agattccgga   240
ggtaaacggt tgtcctccac cccgctggaa atcctgttct ttctgaacgg gtggtataat   300
gctacctatt tcctgctgga acttttcata tttctgtata aaggtgtcct gctaccatat   360
ccaacagcta acctagtact ggatgtggtg atgctcctcc tttatcttgg aattgaagta   420
attcgcctgt tttttggtac aaagggaaac ctctgccagc gaaagatgcc actcagtatt   480
agcgtggcct tgaccttccc atctgccatg atggcctcct attacctgct gctgcaaacc   540
tacgtactcc gcctggaagc catcatgaat ggcatcttgc tcttcttctg tggctcagag   600
cttttacttg aggtgctcac cttggctgct ttctccagta tggacacgat ttgaagtaca   660
gaatttcagc cagcagccca tcaggctgac accacacata tttgcttctg gtactttagc   720
cacaccagtg agaattggtg gggcaagttg tcctgagaaa ggctgtgtgg cttttcttca   780
gcacagacat ttgggcaagc aactcagcat aaggccagtg gtaccatctc tctaaaccag   840
gaccatcagc ccaagagact cttctacact ccagtatagg gaggggcaag gttattccca   900
tcctgcccct tctcagaacc agtcccctgc tgacctcaag ttctcctcct tgatcaccgt   960
ggccagagca tctcgtgtgg accatctagg ctccttgggc ttcaagcagg acctgagcca  1020
catgctccct gtacgagctg tgctatacct gtcccacatg agcacggaga gcctcatgtt  1080
ggtgggtttc cagagtgatg tgaaagcctc tcaccccaat cctcggagac tgagttccac  1140
aactttttta gtagctcata gtgttatttt tctactctct tcatgaaa                1188
```

<210> SEQ ID NO 5
<211> LENGTH: 93
<212> TYPE: DNA
<213> ORGANISM: Homo sapiens

<400> SEQUENCE: 5

```
atgctgccac ggggactgaa gatggcgccg cgaggtgaga ttccggaggt aaacggttgt    60
cctccacccc gctggaaatc ctgttctttc tga                                  93
```

<210> SEQ ID NO 6
<211> LENGTH: 30
<212> TYPE: PRT
<213> ORGANISM: Homo sapiens

<400> SEQUENCE: 6

Met Leu Pro Arg Gly Leu Lys Met Ala Pro Arg Gly Glu Ile Pro Glu
1               5                   10                  15

Val Asn Gly Cys Pro Pro Pro Arg Trp Lys Ser Cys Ser Phe
            20                  25                  30

<210> SEQ ID NO 7
<211> LENGTH: 1307
<212> TYPE: DNA
<213> ORGANISM: Homo sapiens

<400> SEQUENCE: 7
gtgggtggtc accgttatcc cttaggtctg gagaggggac atccgagcga gggccacttg      60
cggccaggcc cgagctcgtc cagctccggg tgaccacaga gtgccgcggg cgggcagagg     120
ggccggaaac ccaggccgct tcgtccctgt ttccggcagc gccgcgctgc tccgggagcc     180
gctgtggcag cgtatgctgc cacggggact gaagatggcg ccgcgagcgt tagggacgtc     240
gcgcctccct ggtccaaagc cggcttccgc ggtcccgccc accctgggtg cctgaaggtc     300
tcaaggtgca cagctcaaat aaacgcagat ccttggctgg ccacttcta ggctggctca     360 ggtaaacggt tgtcctccac cccgctggaa atcctgttct ttctgaacgg gtggtataat     420
gctacctatt tcctgctgga acttttcata tttctgtata aggtgtcct gctaccatat     480 ccaacagcta acctagtact ggatgtggtg atgctcctcc tttatcttgg aattgaagta     540
attcgcctgt tttttggtac aaagggaaac ctctgccagc gaaagatgcc actcagtatt     600
agcgtggcct tgaccttccc atctgccatg atggcctcct attacctgct gctgcagacc     660
tacgtactcc gcctggaagc catcatgaat ggcatcttgc tcttcttctg tggctcagag     720
cttttacttg aggtgctcac cttggctgct ttctccagta tggacacgat ttgaagtaca     780
gaatttcagc cagcagccca tcaggctgac accacacata ttgcttctgg tactttagcc     840
acaccagtga gaattggtgg ggcaagttgt cctgagaaag gctgtgtggc ttttcttcag     900
cacagacatt tgggcaagca actcagcata aggccagtgg gtaccatctt ctaaaccagg     960
accatcagcc caagagactc ttctacactc cagtataggg aggggcaagg ttattcccat    1020 cctgccccctt ctcagaacca gtccctgct gacctcaagt tctcctcctt gatcaccgtg    1080
gccagagcat ctcgtgtgga ccatctaggc tccttgggct tcaagcagga cctgagccac    1140
atgctccctg tacgagctgt gctatacctg tcccacatga gcacggagag cctcatgttg    1200
gtgggtttcc agagtgatgt gaaagcctct caccccaatc ctcggagact gagttccaca    1260
acttttttag tagctcatag tgttatttt ctactctctt catgaaa                   1307

<210> SEQ ID NO 8
<211> LENGTH: 102
<212> TYPE: DNA
<213> ORGANISM: Homo sapiens

<400> SEQUENCE: 8
atgctgccac ggggactgaa gatggcgccg cgagcgttag ggacgtcgcg cctccctggt      60
ccaaagccgg cttccgcggt cccgcccacc ctgggtgcct ga                        102

<210> SEQ ID NO 9
<211> LENGTH: 33
<212> TYPE: PRT
<213> ORGANISM: Homo sapiens

<400> SEQUENCE: 9

Met Leu Pro Arg Gly Leu Lys Met Ala Pro Arg Ala Leu Gly Thr Ser
1               5                   10                  15

Arg Leu Pro Gly Pro Lys Pro Ala Ser Ala Val Pro Pro Thr Leu Gly
            20                  25                  30

Ala

<210> SEQ ID NO 10
<211> LENGTH: 1094
<212> TYPE: DNA
<213> ORGANISM: Homo sapiens

<400> SEQUENCE: 10
gtgggtggtc accgttatcc cttcctgggt gcctgaaggt ctcaaggtgc acagctcaaa      60
taaacgcaga tccttggctg ggccacttct aggctggctc aggtaaacgg ttgtcctcca     120
ccccgctgga atcctgttc tttctgaacg ggtggtataa tgctacctat ttcctgctgg      180
aacttttcat atttctgtat aaaggtgtcc tgctaccata tccaacagct aacctagtac     240
tggatgtggt gatgctcctc ctttatcttg gaattgaagt aattcgcctg ttttttggaa     300
aagcagacca tttggagatg actccatggg ctgtgtctga caggtacaaa gggaaacctc     360
tgccagcgaa agatgccact cagtattagc gtggccttga ccttcccatc tgccatgatg     420
gcctcctatt acctgctgct gcagacctac gtactccgcc tggaagccat catgaatggc     480
atcttgctct tcttctgtgg ctcagagctt ttacttgagg tgctcacctt ggctgctttc     540
tccagtatgg acacgatttg aagtacagaa tttcagccag cagcccatca ggctgacacc     600
acacatattg cttctggtac tttagccaca ccagtgagaa ttggtggggc aagttgtcct     660
gagaaaggct gtgtggcttt tcttcagcac agacatttgg gcaagcaact cagcataagg     720
ccagtgggta ccatcttcta aaccaggacc atcagcccaa gagactcttc tacactccag     780
tatagggagg ggcaaggtta ttcccatcct gccccttctc agaaccagtc ccctgctgac     840
ctcaagttct cctccttgat caccgtggcc agagcatctc gtgtggacca tctaggctcc     900
ttgggcttca gcaggacct gagccacatg ctccctgtac gagctgtgct atacctgtcc     960
cacatgagca cggagagcct catgttggtg ggtttccaga gtgatgtgaa agcctctcac    1020
cccaatcctc ggagactgag ttccacaact tttttagtag ctcatagtgt tattttctca    1080
ctctcttcat gaaa                                                     1094

<210> SEQ ID NO 11
<211> LENGTH: 78
<212> TYPE: DNA
<213> ORGANISM: Homo sapiens

<400> SEQUENCE: 11
atgctaccta ttcctgctg gaacttttca tatttctgta taaaggtgtc ctgctaccat       60
atccaacagc taacctag                                                   78

<210> SEQ ID NO 12
<211> LENGTH: 25
<212> TYPE: PRT
<213> ORGANISM: Homo sapiens

<400> SEQUENCE: 12

Met Leu Pro Ile Ser Cys Trp Asn Phe Ser Tyr Phe Cys Ile Lys Val
1               5                   10                  15

Ser Cys Tyr His Ile Gln Gln Leu Thr
            20                  25

<210> SEQ ID NO 13
<211> LENGTH: 20
<212> TYPE: DNA
<213> ORGANISM: artificial sequence
<220> FEATURE:
<223> OTHER INFORMATION: oligonucleotide primer

<400> SEQUENCE: 13
gatgtggtga tgctcctcct                                          20

<210> SEQ ID NO 14
<211> LENGTH: 20
<212> TYPE: DNA
<213> ORGANISM: artificial sequence
<220> FEATURE:
<223> OTHER INFORMATION: oligonucleotide primer

<400> SEQUENCE: 14
ccaaggtgag cacctcaagt                                          20

<210> SEQ ID NO 15
<211> LENGTH: 62
<212> TYPE: DNA
<213> ORGANISM: Homo sapiens

<400> SEQUENCE: 15
gtacaaaggg aaacctctgc cagcgaaaga tgccactcag tattagcgtg gccttgacct    60
tc                                                                  62

<210> SEQ ID NO 16
<211> LENGTH: 62
<212> TYPE: DNA
<213> ORGANISM: Homo sapiens

<400> SEQUENCE: 16
gaaaagcaga ccatttggag atgactccat gggctgtgtc tgacagctac aaagggaaac    60
ct                                                                  62

<210> SEQ ID NO 17
<211> LENGTH: 20
<212> TYPE: DNA
<213> ORGANISM: artificial sequence
<220> FEATURE:
<223> OTHER INFORMATION: oligonucleotide PCR primer

<400> SEQUENCE: 17
caccgttatc ccttaggtct                                          20

<210> SEQ ID NO 18
<211> LENGTH: 19
<212> TYPE: DNA
<213> ORGANISM: artificial sequence
<220> FEATURE:
<223> OTHER INFORMATION: oligonucleotide PCR primer

<400> SEQUENCE: 18
taggtcaagc tctgggaca                                           19

```
<210> SEQ ID NO 19
<211> LENGTH: 20
<212> TYPE: DNA
<213> ORGANISM: artificial sequence
<220> FEATURE:
<223> OTHER INFORMATION: oligonucleotide PCR primer

<400> SEQUENCE: 19
tagacaccaa cccatacgag                                              20

<210> SEQ ID NO 20
<211> LENGTH: 19
<212> TYPE: DNA
<213> ORGANISM: artificial sequence
<220> FEATURE:
<223> OTHER INFORMATION: oligonucleotide PCR primer

<400> SEQUENCE: 20
ttggtaggaa ttggctctg                                               19

<210> SEQ ID NO 21
<211> LENGTH: 20
<212> TYPE: DNA
<213> ORGANISM: artificial sequence
<220> FEATURE:
<223> OTHER INFORMATION: oligonucleotide PCR primer

<400> SEQUENCE: 21
tggaaagctg agactgatgt                                              20

<210> SEQ ID NO 22
<211> LENGTH: 21
<212> TYPE: DNA
<213> ORGANISM: artificial sequence
<220> FEATURE:
<223> OTHER INFORMATION: oligonucleotide PCR primer

<400> SEQUENCE: 22
taccagcttg tctcataagg a                                            21

<210> SEQ ID NO 23
<211> LENGTH: 20
<212> TYPE: DNA
<213> ORGANISM: artificial sequence
<220> FEATURE:
<223> OTHER INFORMATION: oligonucleotide PCR primer

<400> SEQUENCE: 23
cattccatca catctcccac                                              20

<210> SEQ ID NO 24
<211> LENGTH: 20
<212> TYPE: DNA
<213> ORGANISM: artificial sequence
<220> FEATURE:
<223> OTHER INFORMATION: oligonucleotide PCR primer

<400> SEQUENCE: 24
atgagaaatg gtccctcagc                                              20

<210> SEQ ID NO 25
<211> LENGTH: 20
<212> TYPE: DNA
<213> ORGANISM: artificial sequence
<220> FEATURE:
<223> OTHER INFORMATION: oligonucleotide PCR primer
```

```
<400> SEQUENCE: 25
gctgctctca ttcactggtc                                              20

<210> SEQ ID NO 26
<211> LENGTH: 20
<212> TYPE: DNA
<213> ORGANISM: artificial sequence
<220> FEATURE:
<223> OTHER INFORMATION: oligonucleotide PCR primer

<400> SEQUENCE: 26
acagcctttc tcaggacaac                                              20

<210> SEQ ID NO 27
<211> LENGTH: 10
<212> TYPE: PRT
<213> ORGANISM: artificial sequence
<220> FEATURE:
<223> OTHER INFORMATION: synthetic peptide

<400> SEQUENCE: 27

Asn Leu Cys Gln Arg Lys Met Pro Leu Ser
1               5                   10

<210> SEQ ID NO 28
<211> LENGTH: 11
<212> TYPE: PRT
<213> ORGANISM: artificial sequence
<220> FEATURE:
<223> OTHER INFORMATION: synthetic peptide

<400> SEQUENCE: 28

Asn Leu Cys Gln Arg Lys Met Pro Leu Ser Cys
1               5                   10

<210> SEQ ID NO 29
<211> LENGTH: 22
<212> TYPE: DNA
<213> ORGANISM: artificial sequence
<220> FEATURE:
<223> OTHER INFORMATION: oligonucleotide PCR primer

<400> SEQUENCE: 29
ggtgagattc cggaggtaaa cg                                           22

<210> SEQ ID NO 30
<211> LENGTH: 20
<212> TYPE: DNA
<213> ORGANISM: artificial sequence
<220> FEATURE:
<223> OTHER INFORMATION: oligonucleotide PCR primer

<400> SEQUENCE: 30
ccaaggtgag cacctcaagt                                              20

<210> SEQ ID NO 31
<211> LENGTH: 25
<212> TYPE: RNA
<213> ORGANISM: Homo sapiens

<400> SEQUENCE: 31
gcugcugcuc uaucuuggca uugaa                                        25
```

```
<210> SEQ ID NO 32
<211> LENGTH: 25
<212> TYPE: RNA
<213> ORGANISM: Homo sapiens

<400> SEQUENCE: 32
cccuuggcau uaguguggcc uugac                                          25

<210> SEQ ID NO 33
<211> LENGTH: 25
<212> TYPE: RNA
<213> ORGANISM: Homo sapiens

<400> SEQUENCE: 33
cccauccgcu augauggcuu ccuau                                          25

<210> SEQ ID NO 34
<211> LENGTH: 25
<212> TYPE: DNA
<213> ORGANISM: artificial sequence
<220> FEATURE:
<223> OTHER INFORMATION: synthetic polynucleotide

<400> SEQUENCE: 34
ggttgtcttc cgtgggcagc catgt                                          25

<210> SEQ ID NO 35
<211> LENGTH: 17
<212> TYPE: DNA
<213> ORGANISM: Artificial Sequence
<220> FEATURE:
<223> OTHER INFORMATION: Synthetic

<400> SEQUENCE: 35
agtaattctc ctgtttt                                                   17

<210> SEQ ID NO 36
<211> LENGTH: 16
<212> TYPE: DNA
<213> ORGANISM: Artificial Sequence
<220> FEATURE:
<223> OTHER INFORMATION: Synthetic

<400> SEQUENCE: 36
gtaattcacc tgtttt                                                    16

<210> SEQ ID NO 37
<211> LENGTH: 15
<212> TYPE: DNA
<213> ORGANISM: Artificial Sequence
<220> FEATURE:
<223> OTHER INFORMATION: Synthetic

<400> SEQUENCE: 37
agtaattcgc ctgtt                                                     15

<210> SEQ ID NO 38
<211> LENGTH: 15
<212> TYPE: DNA
<213> ORGANISM: Artificial Sequence
<220> FEATURE:
<223> OTHER INFORMATION: Synthetic

<400> SEQUENCE: 38
gagctttgac ttgag                                                     15
```

```
<210> SEQ ID NO 39
<211> LENGTH: 15
<212> TYPE: DNA
<213> ORGANISM: Artificial Sequence
<220> FEATURE:
<223> OTHER INFORMATION: Synthetic

<400> SEQUENCE: 39
gtaattcgcc tgttt                                                    15

<210> SEQ ID NO 40
<211> LENGTH: 15
<212> TYPE: DNA
<213> ORGANISM: Artificial Sequence
<220> FEATURE:
<223> OTHER INFORMATION: Synthetic

<400> SEQUENCE: 40
agtaattcgc ctgtt                                                    15

<210> SEQ ID NO 41
<211> LENGTH: 15
<212> TYPE: DNA
<213> ORGANISM: Artificial Sequence
<220> FEATURE:
<223> OTHER INFORMATION: Synthetic

<400> SEQUENCE: 41
gagcttttac ttgag                                                    15

<210> SEQ ID NO 42
<211> LENGTH: 15
<212> TYPE: DNA
<213> ORGANISM: Artificial Sequence
<220> FEATURE:
<223> OTHER INFORMATION: Synthetic

<400> SEQUENCE: 42
tacgtacgcc gcctg                                                    15

<210> SEQ ID NO 43
<211> LENGTH: 14
<212> TYPE: DNA
<213> ORGANISM: Artificial Sequence
<220> FEATURE:
<223> OTHER INFORMATION: Synthetic

<400> SEQUENCE: 43
acagctacaa aggg                                                     14

<210> SEQ ID NO 44
<211> LENGTH: 18
<212> TYPE: DNA
<213> ORGANISM: Artificial Sequence
<220> FEATURE:
<223> OTHER INFORMATION: Synthetic

<400> SEQUENCE: 44
ctctgccagt gaaagatg                                                 18

<210> SEQ ID NO 45
<211> LENGTH: 15
<212> TYPE: DNA
<213> ORGANISM: Artificial Sequence
<220> FEATURE:
<223> OTHER INFORMATION: Synthetic
```

```
<400> SEQUENCE: 45
tacgtactcc gcctg                                                    15

<210> SEQ ID NO 46
<211> LENGTH: 14
<212> TYPE: DNA
<213> ORGANISM: Artificial Sequence
<220> FEATURE:
<223> OTHER INFORMATION: Synthetic

<400> SEQUENCE: 46
acaggtacaa aggg                                                     14

<210> SEQ ID NO 47
<211> LENGTH: 18
<212> TYPE: DNA
<213> ORGANISM: Artificial Sequence
<220> FEATURE:
<223> OTHER INFORMATION: Synthetic

<400> SEQUENCE: 47
ctctgccagc gaaagatg                                                 18
```

COMPOSITIONS AND METHODS FOR DETERMINING GENETIC POLYMORPHISMS IN THE TMEM216 GENE

RELATED APPLICATIONS

This application is a continuation of U.S. patent application Ser. No. 14/079,397, filed Nov. 13, 2013, now pending, which is a continuation of Ser. No. 13/098,345 filed Apr. 29, 2011, now U.S. Pat. No. 8,614,094. The aforementioned applications are expressly incorporated herein by reference in their entirety and for all purposes.

STATEMENT REGARDING FEDERALLY SPONSORED RESEARCH OR DEVELOPMENT

This invention was made with Government support under NS048453 awarded by the National Institutes of Health. The Government has certain rights in the invention.

FIELD OF THE INVENTION

This invention generally relates to human genetics and diagnostics, and medicine. In alternative embodiments, the invention provides nucleic acid sequences that are genetic polymorphic variations of the human TMEM216 gene, and TMEM216 polypeptide encoded by these variant alleles. In alternative embodiments, the invention provides methods of determining or predicting a predisposition to, or the presence of, a ciliopathy (or any genetic disorder of a cellular cilia or cilia anchoring structure, basal body or ciliary function) in an individual, such as a Joubert Syndrome (JS), a Joubert Syndrome Related Disorder (JSRD) or a Meckel Syndrome (MKS). In alternative embodiments, the invention provides compositions and methods for the identification of genetic polymorphic variations in the human TMEM216 gene, and methods of using the identified genetic polymorphisms and the proteins they encode, e.g., to screen for compounds that can modulate the human TMEM216 gene product, and possibly treat JS, JSRD or MKS. In alternative embodiments, the invention provides cells, cell lines and/or non-human transgenic animals that can be used as screening or model systems for studying ciliopathies and testing various therapeutic approaches in treating ciliopathies, e.g., JS, JSRD or MKS.

INTRODUCTION

Joubert syndrome is characterized by a distinctive cerebellar and brainstem malformation, hypotonia, developmental delays, and either episodic hyperpnea or apnea or atypical eye movements or both. Most children with Joubert syndrome develop truncal ataxia and delayed acquisition of gross motor milestones is common. Cognitive abilities are variable, ranging from severe mental retardation to normal. The delineation of the phenotypic spectrum of Joubert syndrome remains unresolved, and both intra- and interfamilial variation are seen. Other features sometimes identified in Joubert syndrome include retinal dystrophy, renal disease, ocular colobomas, occipital encephalocele, hepatic fibrosis, polydactyly, oral hamartomas, and endocrine abnormalities.

The current diagnosis of Joubert syndrome is based on the presence of characteristic clinical features and the "molar tooth sign" on cranial magnetic resonance imaging (MRI), resulting from hypoplasia of the cerebellar vermis and accompanying brainstem abnormalities on axial imaging through the junction of the midbrain and pons (isthmus region). The resulting images resemble the section of a tooth. Currently, four causative genes have been identified in which mutations appear to account for no more than 10% of cases of Joubert syndrome each are NPHP1, CEP290, AHI1, and TMEM67 (MKS3); other causative genes to this date were unknown. Molecular genetic testing is clinically available for all four genes.

Joubert syndrome is inherited in an autosomal recessive manner. At conception, each sibling of an affected individual has a 25% chance of being affected, a 50% chance of being an asymptomatic carrier, and a 25% chance of being unaffected and not a carrier. Once an at-risk sib is known to be unaffected, the chance of his/her being a carrier is 2/3. Carrier testing for at-risk family members is available if the mutations have been identified in the proband. Prenatal diagnosis for mutations in AHI1, CEP290, TMEM67, and NPHP1 mutations is available if the mutations have been identified in the proband or carrier parents. Prenatal diagnosis using ultrasound examination with or without fetal MRI has been successful.

Although diagnostics are available for Joubert syndrome, the current lack of specificity is unsatisfactory. Therefore, what is needed are new genes that are identified on the basis of their genetic linkage to Joubert Syndrome and Related Disorders (JSRD) and other ciliopathies, including Meckel Syndrome (MKS), particularly in the Ashkenazi Jewish population. It is desirable to identify naturally existing deleterious mutations in the genes which may serve as valuable diagnostic markers.

TMEM216 localizes prominently around the primary cilium, and patient fibroblasts show defective ciliogenesis and centrosomal docking, with concomitant hyperactivation of RhoA and Dishevelled. TMEM216 complexed with Meckelin, encoded by a gene also mutated in JSRD and MKS, and abrogation of tmem216 expression in zebrafish led to gastrulation defects that overlap with other ciliary morphants. The data implicate a new family of proteins in the ciliopathies, and further support allelism between ciliopathy disorders.

The "ciliopathies" are a newly emerging group of diseases due to defects in the function or structure of cellular primary cilia, which are small cellular appendages previously of unknown function. Recent discoveries have identified that a host of genes of previously unknown function play essential roles at primary cilia, which are mutated in diseases including but not limited to obesity, polycystic kidney disease, mental retardation, retinal blindness, ataxia, liver fibrosis, and some forms of cancer.

SUMMARY

In alternative embodiments, the invention provides compositions and methods for the identification of genetic polymorphic variations in the human TMEM216 gene, and methods of using the identified genetic polymorphisms.

In alternative embodiments, the invention provides methods of determining or predicting a predisposition to, or the presence of, a ciliopathy (or any genetic disorder of a cellular cilia or cilia anchoring structure, basal body or ciliary function) in an individual, comprising:

(a) (i) determining the presence or absence of at least one Transmembrane Protein 216 (TMEM216) genetic variant in the individual, wherein the at least one TMEM216 genetic variant comprises an amino acid variation (from wild type) selected from the group consisting of R73L, R73H, R73C, L133X, L114R, G77A and R85X, (ii) determining or predicting a predisposition to, or the presence of, a Joubert Syndrome (JS), a Joubert Syndrome Related Disorder (JSRD), a ciliopathy (or a genetic disorder of a cellular cilia or cilia anchoring structure, basal body or ciliary function), and/or a Meckel Syndrome (MKS)

wherein the presence of at least one of the TMEM216 amino acid variants indicates a predisposition to, or the presence of, a Joubert Syndrome (JS), a Joubert Syndrome Related Disorder (JSRD), a ciliopathy (or a genetic disorder of a cellular cilia or cilia anchoring structure, basal body or ciliary function), and/or a Meckel Syndrome (MKS).

(b) the method of (a), comprising obtaining or isolating a TMEM216-comprising nucleic acid from the individual, wherein optionally the TMEM216 nucleic acid is an RNA, a DNA, a cDNA or a genomic DNA; or (c) the method of (a) or (b), further comprising embodying the determining or predicting a predisposition to, or the presence of, step in a communicable form for communication to the individual and/or physician; wherein optionally the communicable form comprises a computer program product for communication to the individual and/or physician; and optionally the computer program product enables internet or telecommunications to the individual and/or physician.

In alternative embodiments of the methods, the amino acid variation comprises or consists of a R73L amino acid variation; or the amino acid variation comprises or consists of a R73H amino acid variation; or the amino acid variation comprises or consists of a R73C amino acid variation; or the amino acid variation comprises or consists of: a R73L and a R73C amino acid variation; a R73L and a R73H amino acid variation; a R73H and a R73C amino acid variation, or a R73L, R73H and a R73C amino acid variation; or any combination thereof.

In alternative embodiments of the methods, the ciliopathy is a Joubert Syndrome Related Disorder (JSRD) amino acid variation, a Joubert Syndrome or a Meckel Syndrome (MKS).

In alternative embodiments of the methods, the step of determining the presence or absence of at least one tmem216 genetic variant in the individual, or determining one or more or all of the tmem216 genetic variants in the individual, comprises:

(a) a sequencing, or a determining the sequence of, a TMEM216 nucleic acid obtained from the individual, optionally comprising a Maxim-Gilbert sequencing procedure (method, assay);

(b) a nucleic acid hybridization to a TMEM216 nucleic acid obtained from the individual;

(c) a polymerase chain reaction (PCR) assay, or a chain-terminator method (procedure, assay) (or Sanger method), or an emulsion PCR assay;

(d) amplifying a portion of a TMEM216 nucleic acid obtained from said patient and determining the presence of a genetic variation;

(e) a SOLiD (Sequencing by Oligonucleotide Ligation and Detection) method (Life Technologies, Carlsbad, Calif.);

(f) a high-throughput sequencing technology, or a DNA nanoball sequencing method;

(g) a Massive Parallel Signature Sequencing (MPSS);

(g) a dye-terminator sequencing procedure, a reversible dye-terminator sequencing procedure, or an Illumina (Solexa) sequencing process:

(h) an ion semiconductor sequencing (e.g., by Ion Torrent Systems Inc.); or (i) a parallelized version of pyrosequencing (454 Life Sciences. Branford, Connecticut).

In alternative embodiments, the invention provides isolated, synthetic or recombinant nucleic acids comprising or consisting of:

(a) a sequence selected from the group consisting of SEQ ID NO:3, SEQ ID NO:5, SEQ ID NO:8, SEQ ID NO: 11, and sequences completely complementary thereof: or (b) a nucleic acid encoding a polypeptide having an amino acid sequence of SEQ ID NO: 1, SEQ ID NO:6, SEQ ID NO:9 or SEQ ID NO: 12, and sequences completely complementary thereof;

(c) a nucleic acid encoding a human Transmembrane Protein 216 (TMEM216) amino acid variant having an amino acid sequence of SEQ ID NO: 1, and an amino acid variation selected from the group consisting of R73L, R73H, R73C, L133X, L114R, G77A and R85X; or any combination of R73L, R73H, R73C, L133X, L114R, G77A and R85X; or all of R73L, R73H, R73C, L133X, L114R. G77A and R85X;

(d) a nucleic acid encoding the polypeptide of any of (a) to (c), wherein the amino acid variation comprising or consisting of R73L;

(e) a nucleic acid encoding the polypeptide of any of (a) to (c), wherein the amino acid variation comprising or consisting of R73H;

(f) a nucleic acid encoding the polypeptide of any of (a) to (c), wherein the amino acid variation comprising or consisting of R73C;

(g) a nucleic acid encoding the polypeptide of any of (a) to (c), wherein the amino acid variation comprising or consisting of L133X;

(h) a nucleic acid encoding the polypeptide of any of (a) to (c), wherein the amino acid variation comprising or consisting of L114R;

(i) a nucleic acid encoding the polypeptide of any of (a) to (c), wherein the amino acid variation comprising or consisting of G77A; or (j) a nucleic acid encoding the polypeptide of any of (a) to (c), wherein the amino acid variation comprising or consisting of R85X.

In alternative embodiments, the invention provides isolated, synthetic or recombinant polypeptides (or proteins or peptides) comprising or consisting of:

(a) an amino acid sequence of SEQ ID NO:1, SEQ ID NO:6, SEQ ID NO:9 or SEQ ID NO:12;

(b) a human TMEM216 amino acid variant having an amino acid sequence of SEQ ID NO: 1, and an amino acid variation selected from the group consisting of R73L, R73H, R73C, L133X, L14R, G77A and R85X; or any combination of R73L, R73H. R73C, L133X, L114R, G77A and R85X; or all of R73L, R73H, R73C, L133X, L114R, G77A and R85X:

(c) the polypeptide of (a) or (b), wherein the amino acid variation comprises or consists of a R73L;

(d) the polypeptide of (a) or (b), wherein the amino acid variation comprises or consists of a R73H;

(e) the polypeptide of (a) or (b), wherein the amino acid variation comprises or consists of a R73C:

(f) the polypeptide of (a) or (b), wherein the amino acid variation comprises or consists of a L133X:

(g) the polypeptide of (a) or (b), wherein the amino acid variation comprises or consists of a L114R;

(h) the polypeptide of (a) or (b), wherein the amino acid variation comprises or consists of a G77A; or (i) the polypeptide of (a) or (b), wherein the amino acid variation comprises or consists of a R85X.

In alternative embodiments, the invention provides isolated, synthetic or recombinant, or hybridoma-generated, antibodies (or antigen binding fragments thereof) selectively immunoreactive (that selectively binds to) an isolated, synthetic or recombinant polypeptide of the invention (or encoded by a nucleic acid of the invention), wherein optionally the antibody is a monoclonal or a polyclonal antibody, or an IgG. IgM, IgA antibody, or a partially or fully humanized antibody.

In alternative embodiments, the invention provides arrays, or microarrays, or chips, or microchips, or any solid or semisolid surface, comprising at least one antibody of the invention; or one isolated, synthetic or recombinant nucleic acid of the invention; or at least one isolated, synthetic or recombinant polypeptide of the invention; or any combination thereof.

In alternative embodiments, the invention provides vectors, plasmids or expression systems (or equivalents) comprising at least one isolated, synthetic or recombinant nucleic acid of the invention (which includes any nucleic acid that encodes a polypeptide of the invention).

In alternative embodiments, the invention provides cells, e.g., transformed or transfected cells, e.g., mammalian cells, e.g., human cultured or isolated cells, comprising at least one isolated, synthetic or recombinant nucleic acid of the invention, or at least one vector, plasmid or expression system (or equivalents) of the invention.

In alternative embodiments, the invention provides non-human transgenic animals comprising a heterologous nucleic acid comprising at least one isolated, synthetic or recombinant nucleic acid of the invention, or at least one vector, plasmid or expression system (or equivalents) of the invention.

In alternative embodiments, the invention provides methods for screening for a compound that modulates (modifies) the activity or expression of a TMEM216 gene product, or a TMEM216 protein, comprising:

(a) (i) providing at least one isolated, synthetic or recombinant polypeptide of claim 9;

(ii) providing a test compound; and (iii) contacting the test compound with the at least one isolated, synthetic or recombinant polypeptide, and determining whether the test compound modulates (modifies) the expression or activity of the at least one isolated, synthetic or recombinant polypeptide, wherein determining that the test compound modulates or modifies the expression or activity of the at least one isolated, synthetic or recombinant polypeptide identifies the test compound as a modulator or modifier of) the activity or expression of a TMEM216 gene product, or a TMEM216 protein:

(b) the method of (a), wherein the test compound comprises a protein, a small peptide or a derivative or mimetic thereof; a non-peptide small molecule; a carbohydrate; a nucleic acid; a lipid or a fat; or an analog thereof;

(c) the method of (a), wherein determining that the test compound modulates or modifies the expression or activity of the at least one isolated, synthetic or recombinant polypeptide is based on a binding affinity of a test compound capable of interacting with or binding to a TMEM216 protein variant; or (d) the method of (a), wherein the at least one isolated, synthetic or recombinant polypeptide of the invention is immobilized, optionally immobilized on an array or microarray.

In alternative embodiments, the invention provides computer program products for communication to an individual and/or physician conveying the results of the method of claim 1; and optionally the computer program product enables internet or telecommunications to the individual and/or physician. In alternative embodiments, the invention provides computers having a computer program product of the invention.

The details of one or more embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

BRIEF DESCRIPTION OF DRAWINGS

The patent or application file contains at least one drawing executed in color. Copies of this patent or patent application publication with color drawing(s) will be provided by the Office upon request and payment of the necessary fee.

Those of skill in the art will understand that the drawings, described below, are for illustrative purposes only. The drawings are not intended to limit the scope of the present teachings in any way.

FIG. 1A-E illustrate Mutations in the TMEM216 gene in patients linked to the JBTS2 and MKS2 loci: FIG. 1(*a*) schematically illustrates the chromosomal location of the JBTS2 and MKS2 loci on Chr. 11cent. FIG. 1(*b*) schematically illustrates TMEM216 genomic organization, depicting start and stop codon, and location of identified base changes. FIG. 1(*c*) schematically illustrates the longest splice isoform, which encodes for a 148 amino acid (aa) tetraspan membrane protein (SEQ ID NO: 1). Patient mutations predominate towards the middle of the gene, with R73 changes including R73L, R73H, R73C, and with one prevalent R73 change occurring repeatedly. Missense, nonsense and splice mutations were identified.

FIG. 1(*d*) illustrates evolutionary conservation of mutated amino acids. FIG. 1(*e*) illustrates a Western blot of whole lysate of cells transfected with a cDNA encoding wild type (WT) versus (vs.) patient missense mutations, compared with control (V71L). Each mutation resulted in the production of 40-50% of WT protein levels, compared with α-tubulin loading control. Patient mutations lead to unstable protein products.

FIG. 2A-J illustrate expression analysis, cDNA representation, and ciliary localization of TMEM216: FIG. 2(*a*) illustrates a Northern blot (20 weeks (w) gestation human fetal tissues) using full-length TMEM216 with 1.4 kb band in all tissues tested. FIG. 2(*b*) schematically illustrates a representation of recovered TMEM216 splice isoform clones (n=48) from 20 w gestation human fetal brain cDNA. No single majority isoform was identified, but the longest and most prevalent encoded a predicted protein of 148 aa, which corresponds to EST BI910875. FIG. 2(*c-h*) illustrate expression of TMEM216 based upon in situ hybridization in human embryonic tissue (FIG. 2*c* to FIG. 2*h*) antisense, (c'-g') sense control probes. FIG. 2(*c*) illustrates Carnegie stage (CS)12, i.e. 4 gestational weeks (gw), TMEM216 is ubiquitously expressed within embryonic tissues in transverse section: neural tube (nt), heart primordium (h). Fig. (d-f) illustrate CS15 (5gw) expression is more intense particularly in nt, dorsal root ganglia (drg), mesonephros (mn), gonadal ridge (go) and limb bud. FIG. 2(*g*) illustrates 8gw strong signal in kidney, gonad and adrenal. FIG. 2(*h*) illustrates 8gw with specific expression in CNS in particular in cerebellar bud (cb), cranial nerve ganglia (trigeminal V, facioacoustic VII+VIII) and cartilage anlages (csc), with lower expression in telencephalon. (tel). FIG. 2i and FIG. 2j) (FIG. 2i is the top row three panels, and FIG. 2j is the bottom row three panels) illustrate indicated cell types (IMCD3 and hRPE, respectively) showing overlapping localization of some endogenous TMEM216 (green) and Ac-tubulin or GT335 (glutamylated tubulin) (red) at or near the primary cilium. Scale bar 5 um.

FIG. 3 A-E illustrate TMEM216 mutation or knockdown results in impaired ciliogenesis and centrosome docking: FIG. 3(e) illustrates cell staining showing a method of quantification at 72 hrs. Scale bars: white, most apical 1.0 um; grey, basal 1.5 um.

FIG. 4A-F illustrate TMEM216 is part of a complex with Meckelin and its loss results in Rho hyperactivation, with resultant alteration in actin cytoskeleton: FIG. 4(a) illustrates an immunoblotting of whole cell extract (input WCE) from TMEM216-GFP transfected HEK293 cells confirmed expression of tagged TMEM216 at approximately 37 kD (arrow). Immunoprecipitation (IP) of WCE with anti-Meckelin antisera against either the N or C-termini confirmed a complex with GFP-tagged TMEM216 (arrowhead), which was absent in control IPs with an irrelevant antibody (irr. Ab; anti-Efe4) or the preimmune antiserum. Arrow is IgG heavy chain. FIG. 4(b) illustrates an immunoblotting of a reciprocal IP of a 60 kD C-terminal containing isoform of endogenous Meckelin from WCE of TMEM216-GFP transfected HEK293 cells with anti-meckelin C-terminus (arrowhead), but not by either a no Mab control or an irrelevant antibody (anti-c myc). Arrow is IgG heavy chain. FIG. 4(c) illustrates an immunoblotting of MKS2 fibroblast WCE shows a 6.8-fold increase in levels of activated RhoA-GTP compared to normal control. FIG. 4(d) illustrates an immunoblotting of an siRNA knockdown of Tmem216 in IMCD3 cells, which caused a 7.6-fold increase in RhoA activation, compared with control. Mks3 positive control siRNA also induced a comparable increase (7.7-fold) as reported previously (23). Total RhoA and 3-actin are shown as loading controls. Positive controls for the assays (+; loading with non-hydrolyzable GTPγS) and a negative control (−; loading with GDP) are also shown. FIG. 4(e) illustrates cell staining showing that RhoA (red) localizes to the basal bodies (γ-tubulin, green) in IMCD3 cells following 24 hr treatment with scrambled siRNA, but mislocalizes to regions adjacent to the basal bodies (arrows and inset) and at basolateral surfaces (arrowheads) following Tmem216 knockdown. Mislocalization of γ-tubulin is also apparent (bottom inset). FIG. 4(f) illustrates cell staining showing subcellular phenotypes of fibroblasts cultured from undiseased control and two individuals (162 and 186) with MKS, homozygous for the TMEM216 nonsense mutation p.R85X and compound heterozygous for the MKS3 mutations [p.M261T]+[p.R217X], as indicated. Note prominent actin stress fibers in both mutated cells (arrowheads) as detected by phalloidin staining, with mislocalization of Meckelin and filamin-A to these fibers. Bar: 10 um.

FIG. 5A-G illustrate TMEM216 disruption results in Dvl1 phosphorylation, and planar cell polarity-like phenotypes in zebrafish: FIG. 5(a) illustrates an IP showing that siRNA knockdown of Tmem216 in IMCD3 cells and TMEM216 p.R85X patient fibroblasts causes an increase in the upper (phosphorylated) isoform (P-Dvl1) (left panel). Treatment with the cell permeable Rho inhibitor exoenzyme-C3-transferase (2 ug/ml) in IMCD3 cells caused constitutive Dvl1 phosphorylation. The stimulatory effect of TMEM216 loss on Dvl1 phosphorylation was reversed by Rho inhibition (right panel) FIG. 5(b) illustrates a coimmunoprecipitation of both Dvl1 and RhoA with TMEM216 in TMEM216-GFP transfected cells. Arrowhead indicates Ig fragment. FIG. 5(c) graphically illustrates data showing a dose-dependent rescue of centrosome/basal body docking phenotype in Tmem216 siRNA-treated cells following Rho inhibition. * p<0.01; ** p<0.001, for chi-squared test. FIG. 5(d) schematically illustrates injection of translation-blocking morpholino (MO) to tmem216 vs. scrambled MO in zebrafish results in a ciliary defect phenotype (curved tail, small brain) in the majority of injected embryos (>50 each condition). Injection of human TMEM216 RNA shows no phenotype in wt embryos, but can at least partially rescue the MO phenotype in a dose-dependent fashion (quantified below). FIG. 5(e) schematically illustrates Lateral (top) and dorsal (bottom) views of zebrafish embryos injected with tmem216 or mks3 MO at 8-somite stage demonstrating common ciliopathy features including shortened body axis, wide undulating notochord, thin and elongated somites and small anterior structures. FIG. 5(f) schematically and graphically (bottom two panels) illustrates representative 11-somite stage embryos hybridized with krox20. pax2, and myoD riboprobes. Arrows indicate measurement points at the fifth rhombomere (horizontal arrow) and length of the notochord as indicated by adaxial cell labeling (vertical arrow). FIG. 5(g) illustrates a Graphic quantification showing the severity of gastrulation defect in tmem216 and mks3 morphants, measured along two different axes (convergence to the midline as indicated by the width at the fifth rhombomere, and extension along the AP axis as indicated by notochord length: n=12-15 embryos/injection). Suppression of tmem216 or mks3 resulted in significantly different width and length measurements compared to controls (* p<0.005); the AP extension defect is more pronounced in the mks3 compared with tmem216 morphant (* p<0.005).

FIG. 6A-C illustrate MKS2 fine-mapping: FIG. 6(a) graphically illustrates results of the multipoint linkage analysis in 9 consanguineous families with Affymetrix 10K SNP chips using MERLIN software assuming a fully penetrant recessive model with a disease allele of frequency 0.0001 and allowing for heterogeneity between families. The highest heterogeneity lodscore (Hlod 9.179) was found at rs522073 on chromosome 11, at position 60.635. FIG. 6(b) illustrates in table form results of the Affymetrix 10K SNP: seven affected cases from 6 families showed homozygosity at the refined MKS2 locus. F002 delineated the interval between rs1113480 and rs953894 (48.014-62.518 Mb). FIG. 6(c) illustrates in graphic and in table form that Homozygosity was further confirmed by microsatellite markers analysis and suggested a founder effect by haplotype identity in 2 out of the 3 Tunisian families (F2 and F5) and the 2 Palestinian families (F56 and F58) respectively. MKS15, MKS16 and MKS74 share the same haplotype and were found to carry the same L114R TMEM216 mutation. No mutation was found in MKS860. MKS492 and MKS512 are also haploidentical and carry the same G77A/T78KfsX30. Four heterozygous markers (white boxes) within the homozygous region are probable allelic mutations.

FIG. 7A illustrates chromatograms of TMEM216 mutations found in probands (upper panels). Lower panel shows normal controls. FIG. 7B illustrates analysis of the c.230G>C mutation at the cDNA level. The mutation is located at the first base of exon 5 and was suspected to alter splicing. RT-PCR was performed with primers located in TMEM216 exon 4 (forward: GATGTG-GTGATGCTCCTCCT) (SEQ ID NO:13) and 5 (reverse: CCAAGGTGAGCACCTCAAGT (SEQ ID NO: 14)) on RNA extracted from lymphocytes cell lines in parents of fetus MKS492 and a control (C). Expected wild type size is seen in control (244 bp) while in both heterozygous parents, 2 bands are observed: one corresponding to the wild type allele, and another, corresponding to a larger transcript. Sequence of the father showed an abnormal transcript containing the last 46 bases of intron 4 (boxed in blue, or the shaded box in the lower of the two schematics of the spliced gene), by the use of an alternative splice site (r.230G>C; 229_230ins230-46_230-1). The mutation is indicated in red on the sequence (i.e., is the 5' most "C" residue in the box of the "Mut" sequence. The effect of the c.230G>C on the transcript is shown on the lower panel, on the major and biggest isoform of TMEM216. The mutant transcript predicts a truncated protein with a stop codon 30 amino acids downstream. The predicted effect on protein is p.T79Kfs30.

Figure 7A:
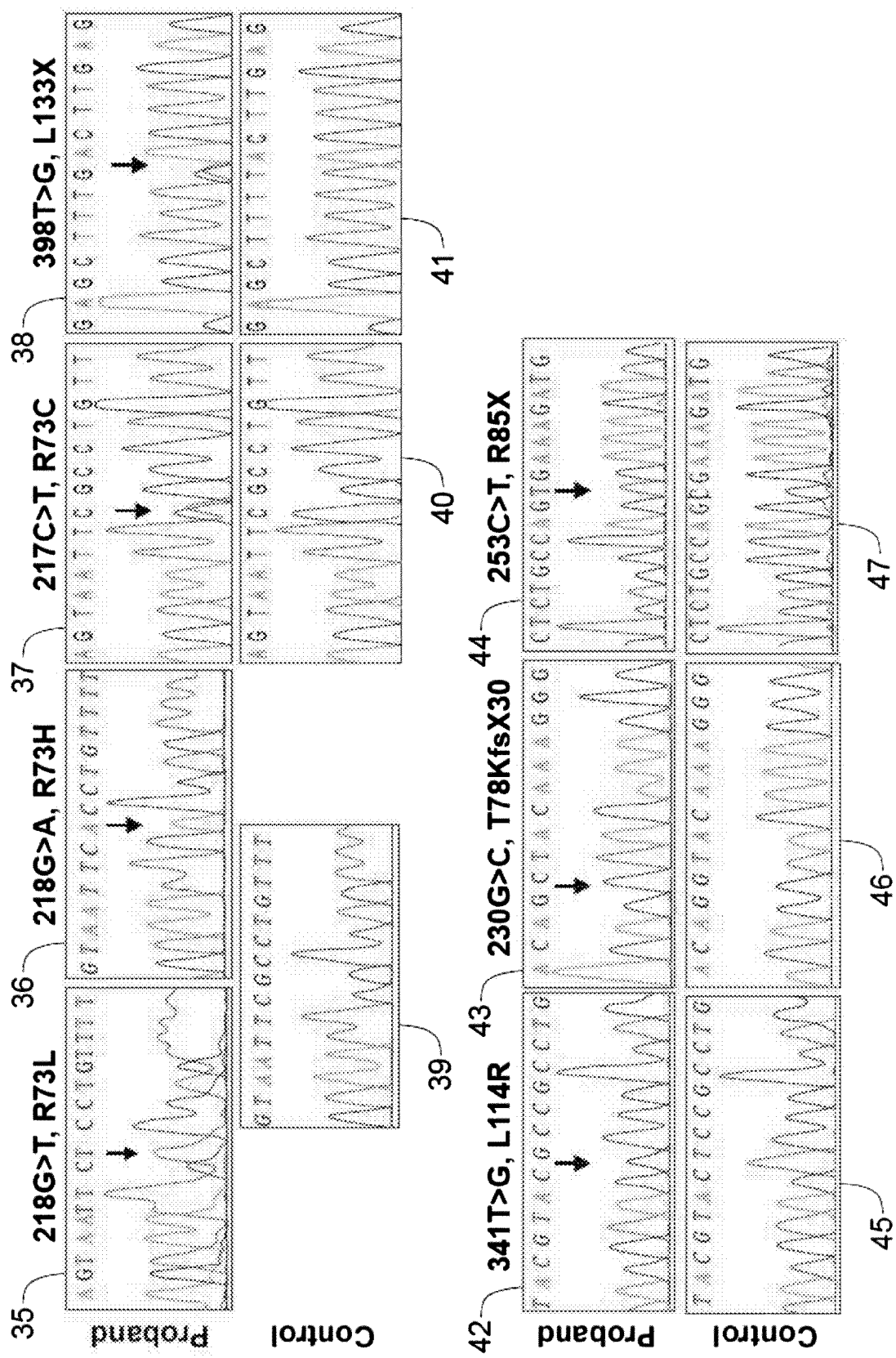
FIG. 7A-B illustrate Chromatograms and RT-PCR analysis of the c.230G>C mutation.

TMEM216 WT sequence is SEQ ID NO:15: GTACAAA GGGAAACCTC TGCCAGCGAA AGATGCCACT CAG-TATTAGC GTGGCCTTGA CCTTC TMEM216 Mut sequence is SEQ ID NO:16: GAAAA GCAGA CCATT TGGAG ATGAC TCCAT GGGCT GTGTC TGACA GCTAC AAAGG GAAAC CT The sequences illustrated in FIG. 7A are:
SEQ ID NO:35: is AGTAATTCTCCTGTTTT
SEQ ID NO:36: is GTAATTCACCTGTTTT
SEQ ID NO:37: is AGTAATTCGCCTGTT
SEQ ID NO:38: is GAGCTTGACTTGAG
SEQ ID NO:39: is GTAATTCGCCTGTTT
SEQ ID NO:40: is AGTAATTCGCCTGTT
SEQ ID NO:41: is GAGCTTTTACTTGAG
SEQ ID NO:42: is TACGTACGCCGCCTG
SEQ ID NO:43: is ACAGCTACAAAGGG
SEQ ID NO:44: is CTCTGCCAGTGAAAGATG
SEQ ID NO:45: is TACGTACTCCGCCTG
SEQ ID NO:46: is ACAGGTACAAAGGG
SEQ ID NO:35: is CTCTGCCAGCGAAAGATG.

Figure 8:
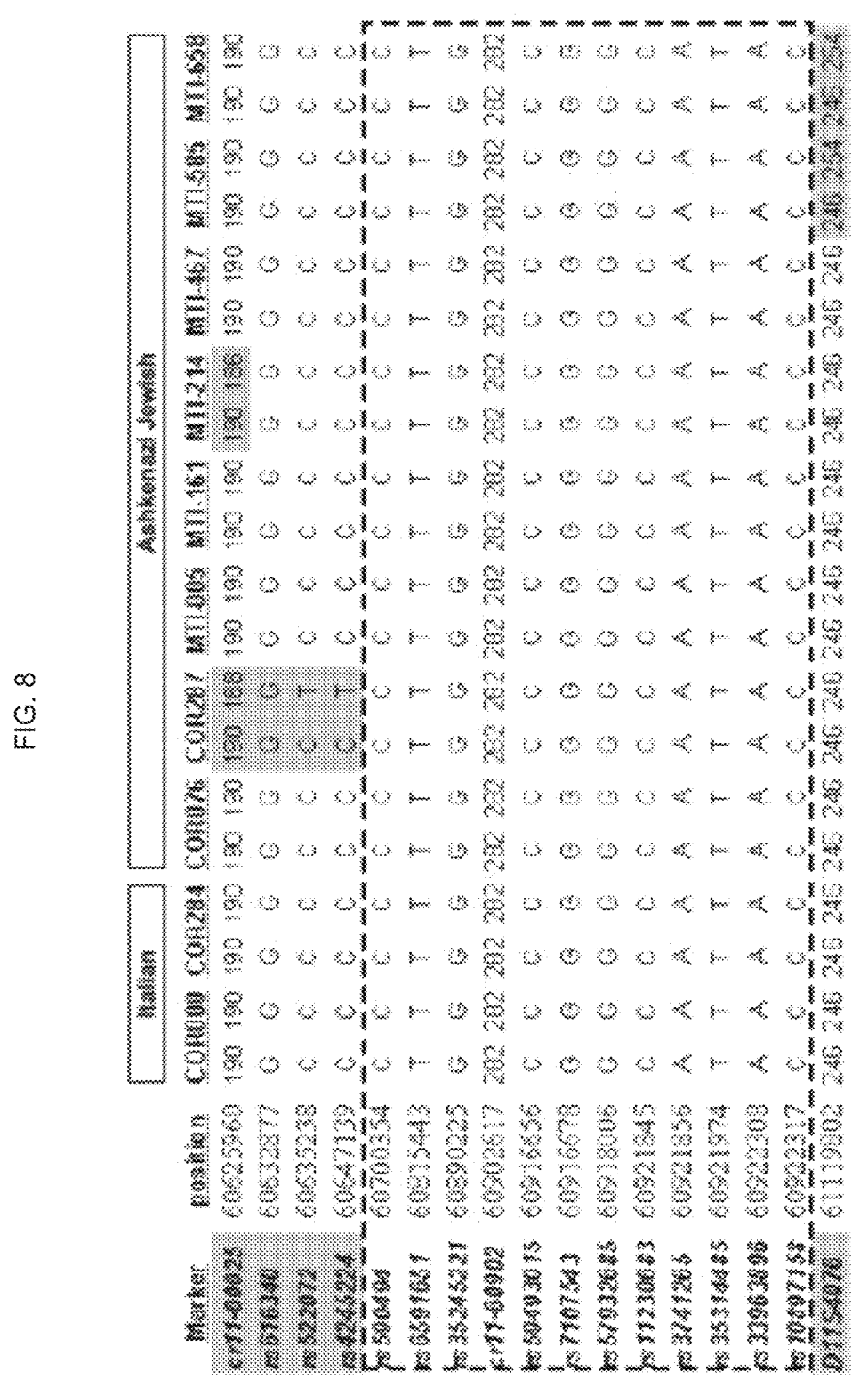

FIG. 8 in table form illustrates Haplotypes of 10 of 12 JSRD families harboring the identical R73L mutation: Alleles (and markers) showing recombination (gray) and homozygous (black) intervals, highlighting the shared homozygous region flanked by rs4245224 (centromeric) and D11S4076 (telomeric).

Figure 9K:
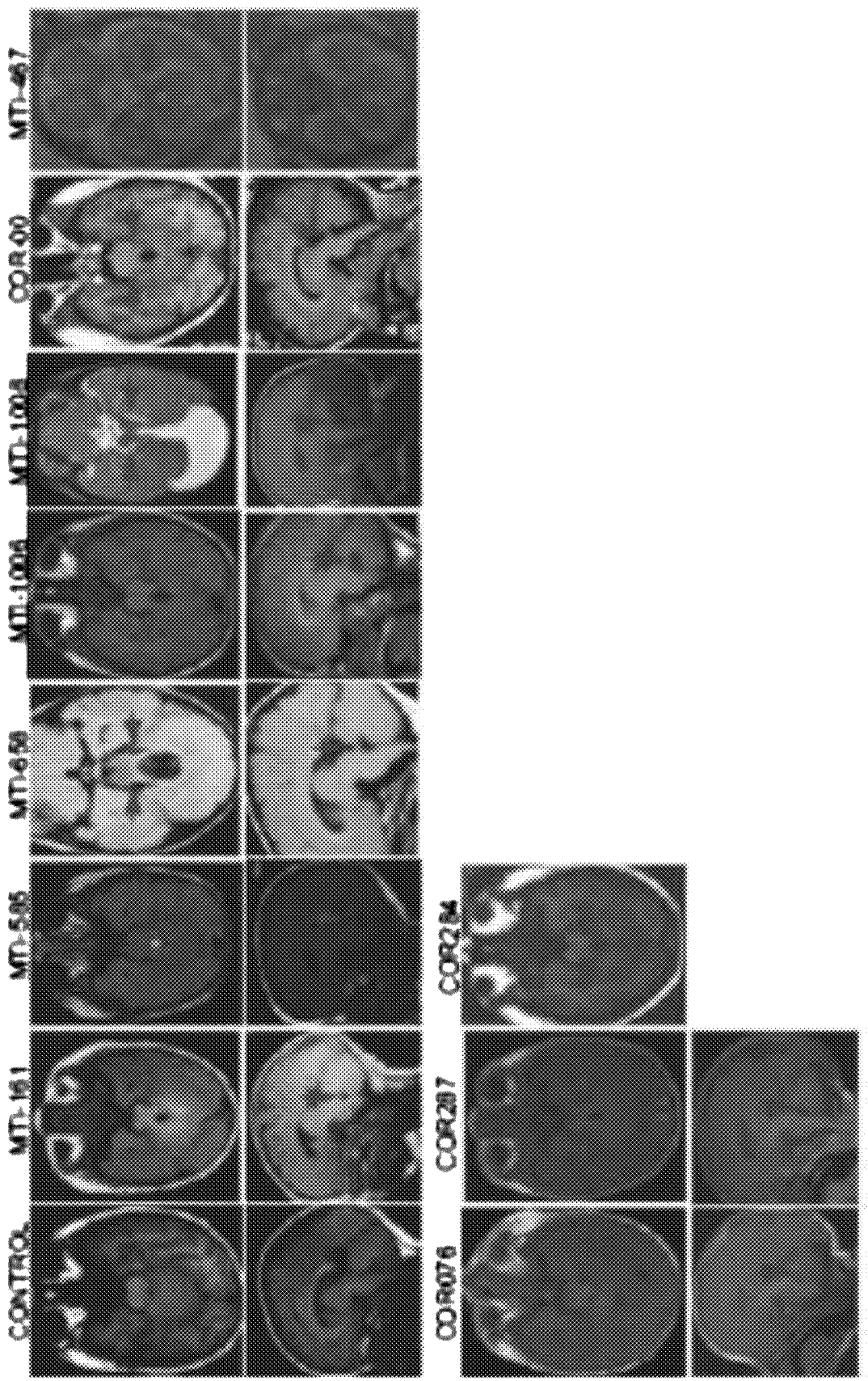

FIG. 9A-K illustrate Clinical data of MKS and JS patients with TMEM216 mutations: FIG. 9(a,b,e,h) illustrates case MKS-15 (21 w), FIG. 9(c,d,f,i) illustrates case MKS-16 (14 w); FIG. 9 (g,j) illustrates MKS-512 (1 day). The picture illustrated as FIG. 9(a) shows the occipital encephalocele, postaxial polydactyly, and distended abdomen due to polycystic kidneys; FIG. 9(b) illustrates X rays shows femoral and tibial bowing. FIG. 9(c) illustrates MKS-16 presents an anencephalic phenotype, FIG. 9(d) illustrates craniorachischisis and postaxial polydactyly. FIG. 9(e-j) illustrate histological sections of kidneys and liver show the cystic kidney dysplasia characteristic of MKS with large cysts both in cortex and medulla, growing in size from periphery to center. Histological sections of liver show the typical ductal plate anomaly in three cases with bile duct proliferation. FIG. 9(k) illustrates MRIs of control and JBTS2 patients. Top shows axial images at the level of the midbrain-hindbrain junction and the apparent "molar tooth sign" (red arrows). Bottom shows midline sagittal sections and the horizontally-oriented an thickened superior cerebellar peduncle (red arrow). Note that MTI-1008 has a large retrocerebellar cyst, with reduced cerebellar parenchymal volume. For MTI-467 (fetal MRI from an affected and terminated pregnancy), and COR284, no sagittal images were available.

Figure 10A:
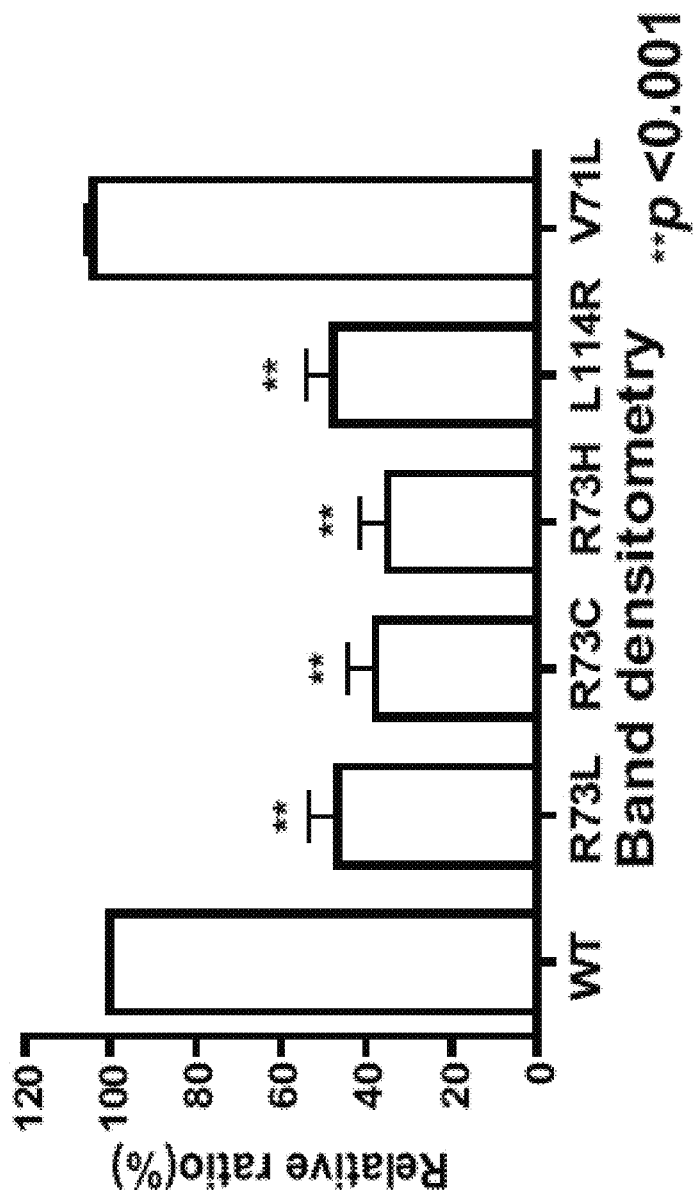
Figure 10B:
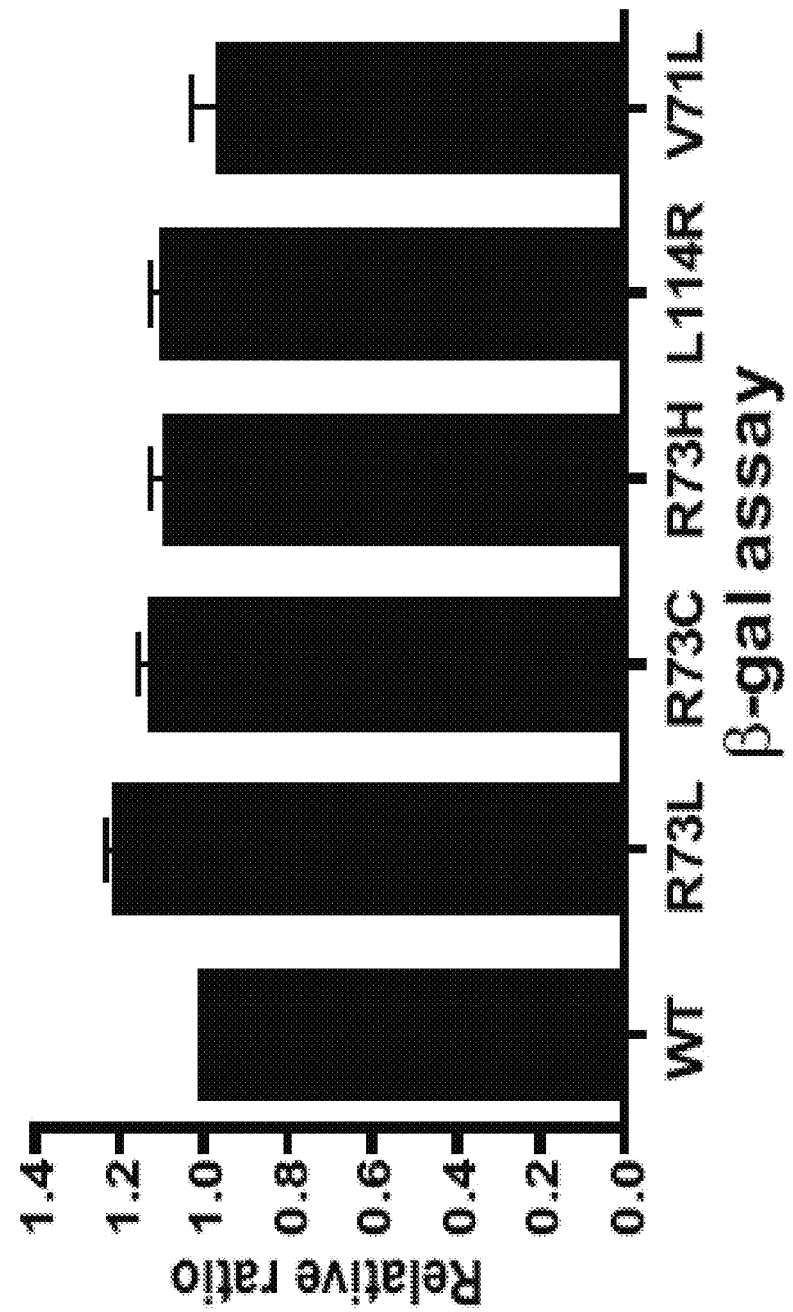

FIG. 10A-B illustrate FIG. 10A graphically illustrates Band densitometry of Western analysis of FIG. 1e, showing reduced levels of TMEM216 carrying any of the patient mutations, whereas a negative control amino acid transversion (V71L) shows levels comparable to WT control. Cells were co-transfected with a vector encoding β-gal; FIG. 10B graphically illustrates similar levels of 3-gal activity across samples, as a control for transfection efficiency.

Figures 1A, 1B:
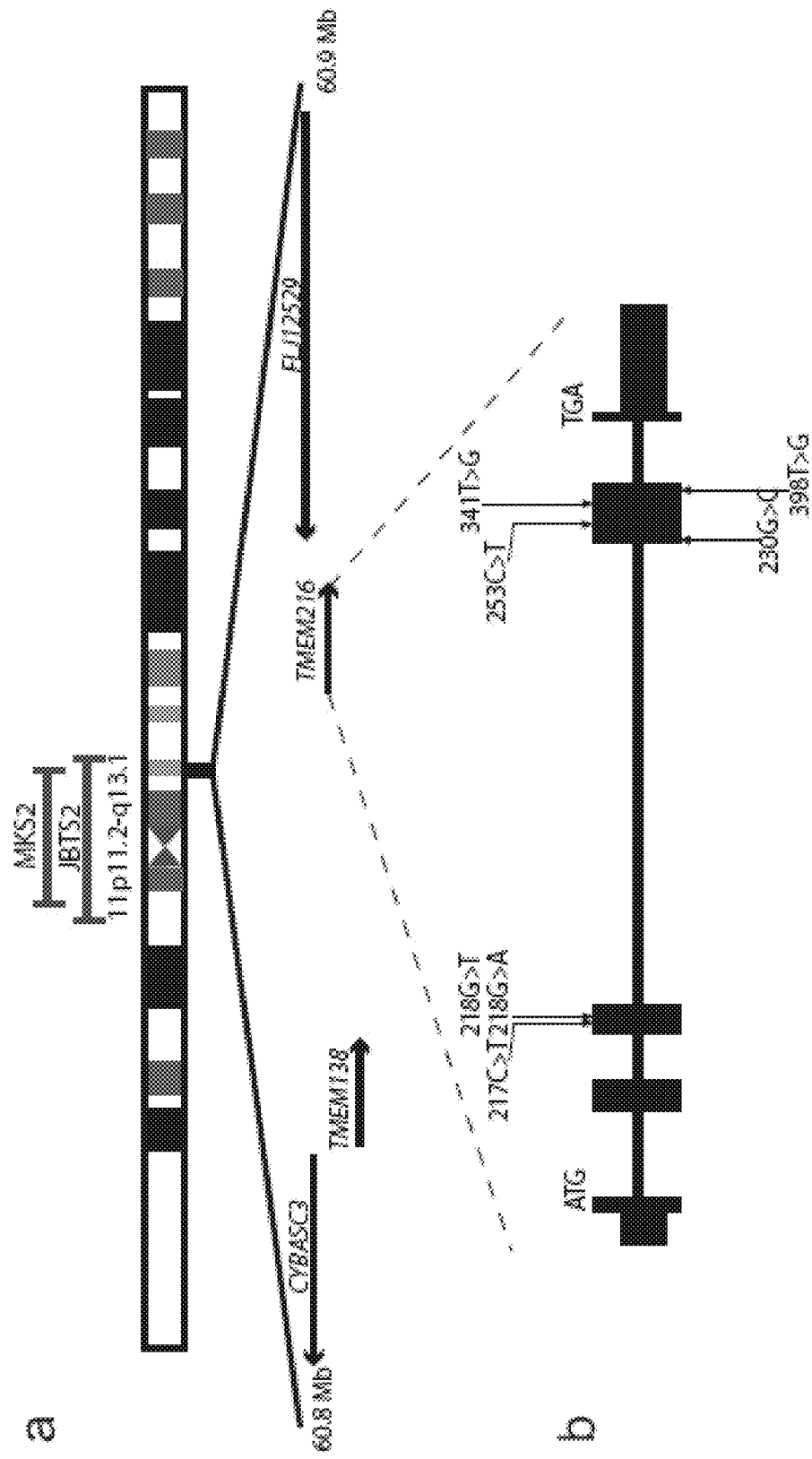
Figure 11B:
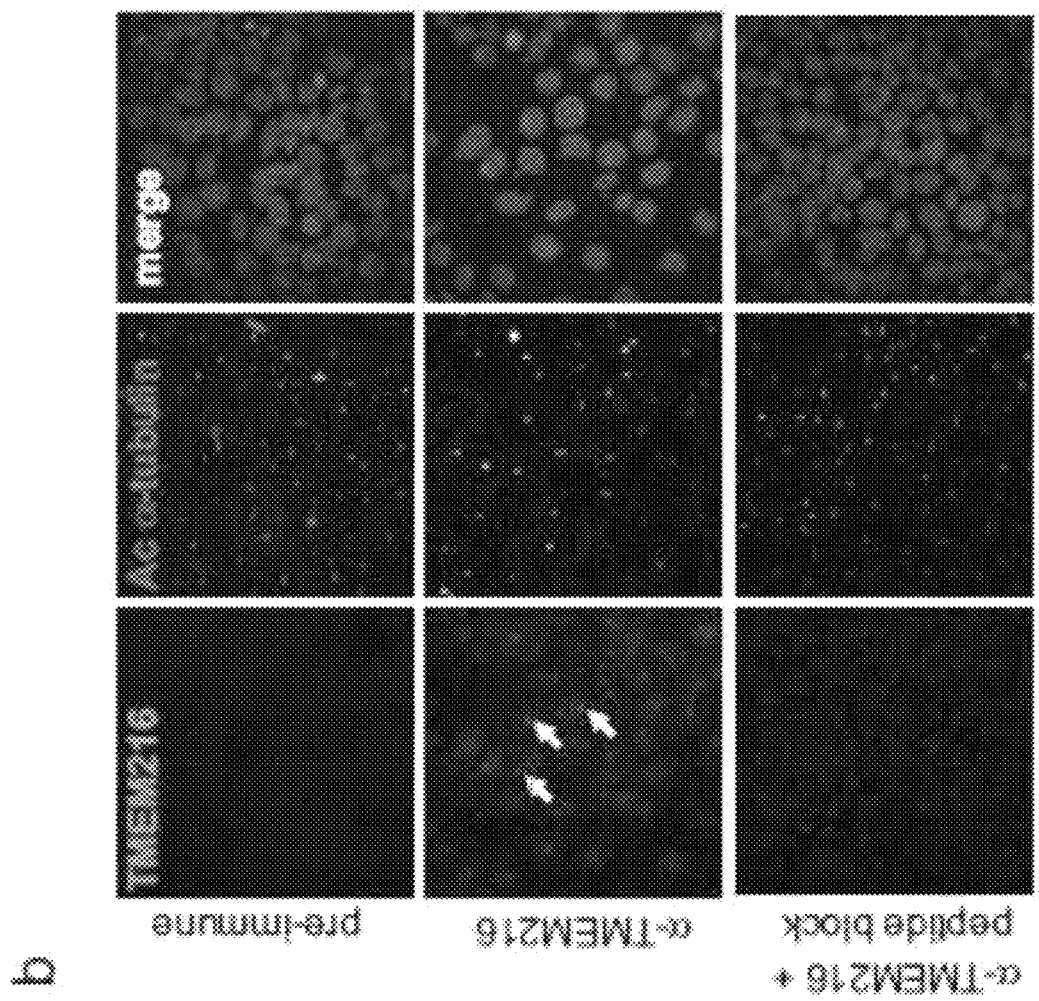
Figure 11C:
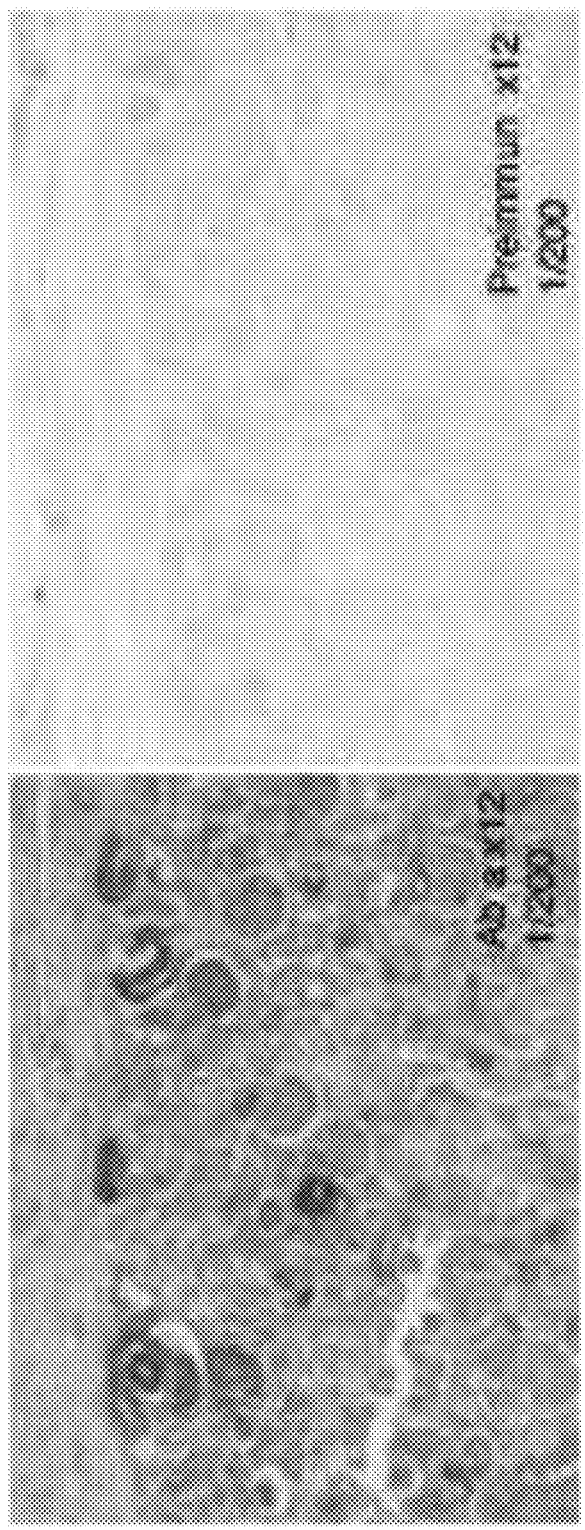

FIG. 11 A-C illustrate Characterization of the anti-TMEM216 rabbit polyclonal antiserum: FIG. 11(a) illustrates an Immunoblotting of ca. 10 µg whole cell extracts (WCEs) with affinity-purified anti-TMEM216 (left panel) and the corresponding pre-immune (right panel), both at ×1000 titers. Immunodetection revealed two major protein isoforms of sizes 27 and 19 kD with anti-TMEM216 but not the preimmune (60 s exposure time). WCEs: 1 & 2, normal control fibroblasts; 3, HEK293; 4 & 5 IMCD3 (early and late passage). FIG. 1(b) illustrates Co-immunostaining and epifluorescence microscopy of post-confluent, ciliated IMCD3 cell monolayers with pre-immune and anti-TMEM216 sera (green, as indicated). Primary cilia were co-stained for acetylated-a-tubulin (red) and nuclei were stained with DAPI (blue). Endogenous TMEM216 co-localizes with primary cilia (middle panels; arrows), which is a staining pattern partially abrogated by treatment of affinity-purified TMEM216 with 50 mg/ml cognate peptide (peptide block control; bottom panels). FIG. 11(c) illustrates Immunostaining of human kidney with TMEM216 ab (left) compared with preimmune serum, both at 1:200 dilution. Visible are dark-stained developing glomerular capsules in the renal cortex.

Figure 12:
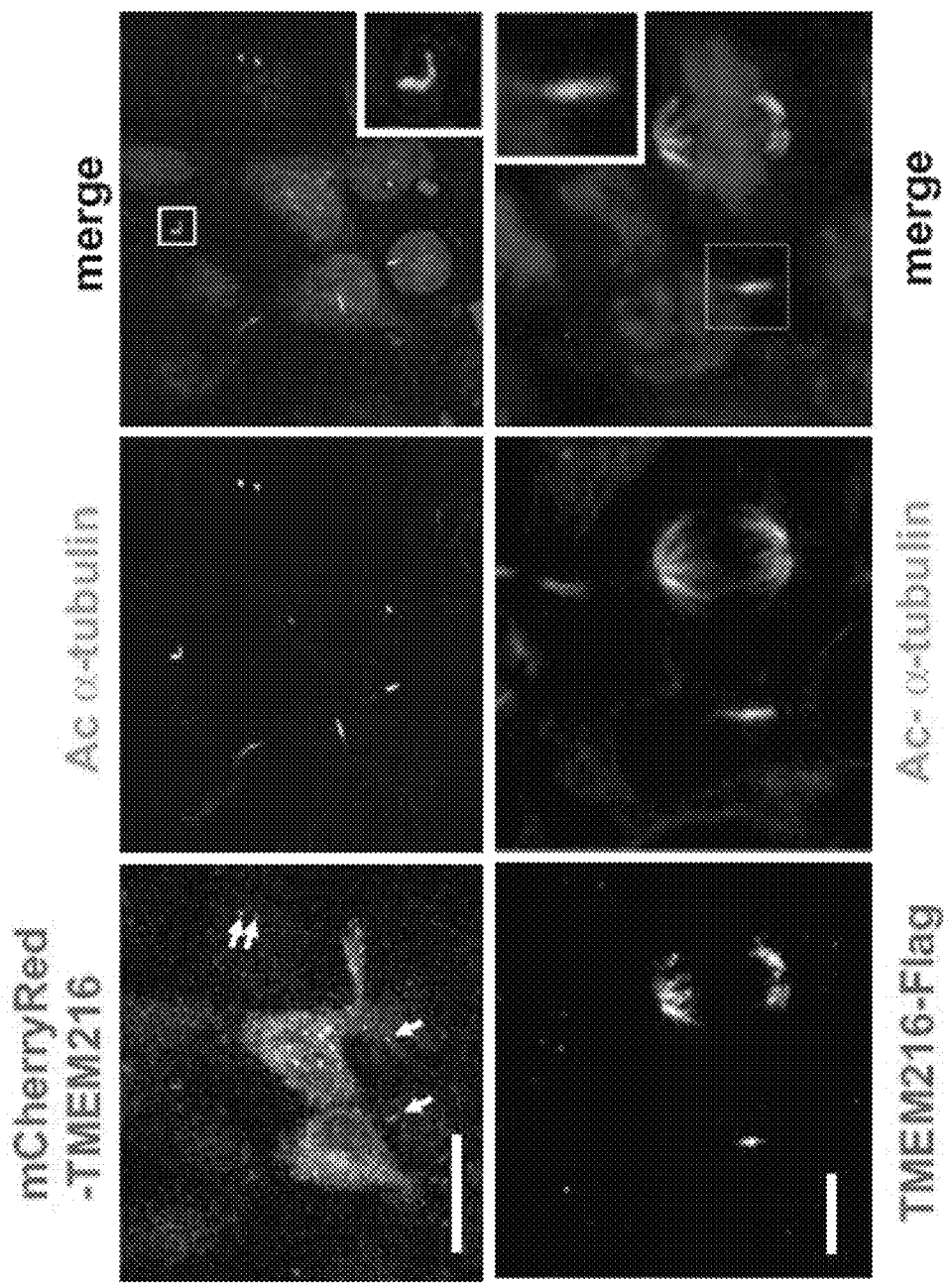

FIG. 12 illustrates Localization of epitope-tagged TMEM126: illustrates Co-immunostaining and confocal microscopy of post-confluent, ciliated IMCD3 cell monolayers transfected with mCherryRed-TMEM216 (red; top panels) and TMEM216-FLAG (red; bottom panels). Primary cilia were co-stained for acetylated-a-tubulin (green). DAPI staining of nuclei is shown in blue. Epitope-tagged TMEM216 co-localizes with primary cilia (arrows), shown in detail in the insets, and the mitotic spindle of a cell in late telophase (bottom panel). Bars=5 um.

Figure 13:
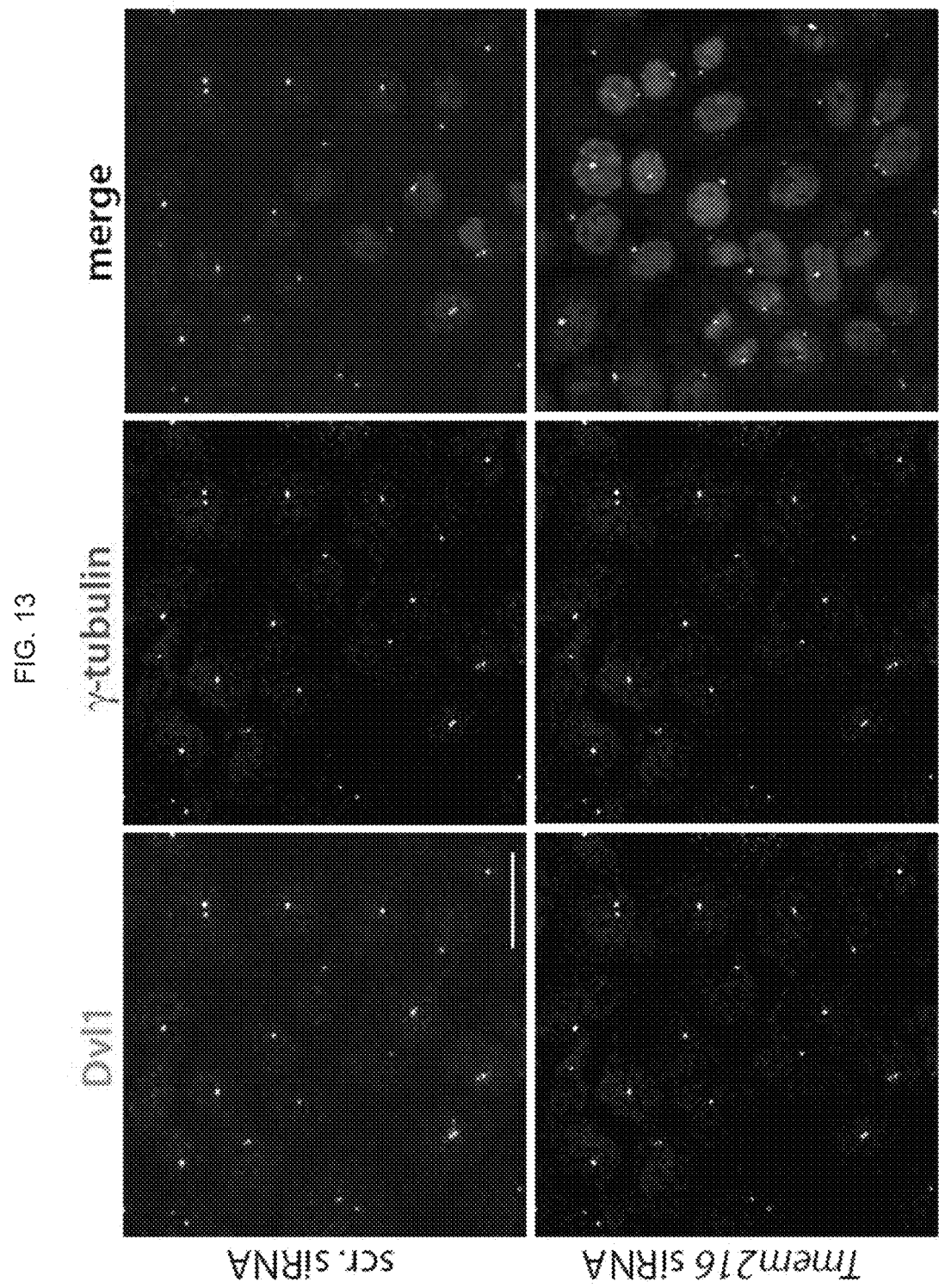

FIG. 13 illustrates Localization of Dvl1 following Tmem216 knockdown. IMCD3 cells were fixed at subconfluence and stained for γ-tubulin and Dvl1. There was no notable difference in localization of Dvl1 in the presence or absence of Tmem216 siRNAs. Scale bar 10 um.

Figure 14:
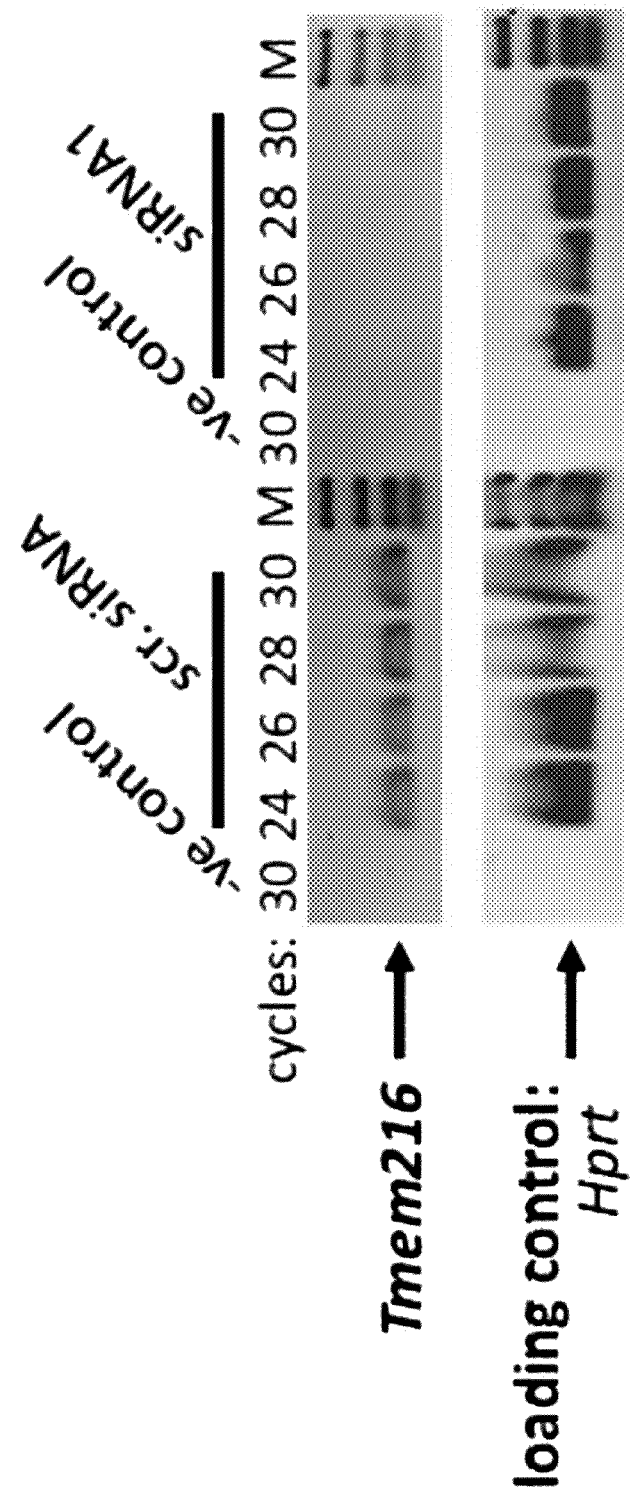
Figure 15I:
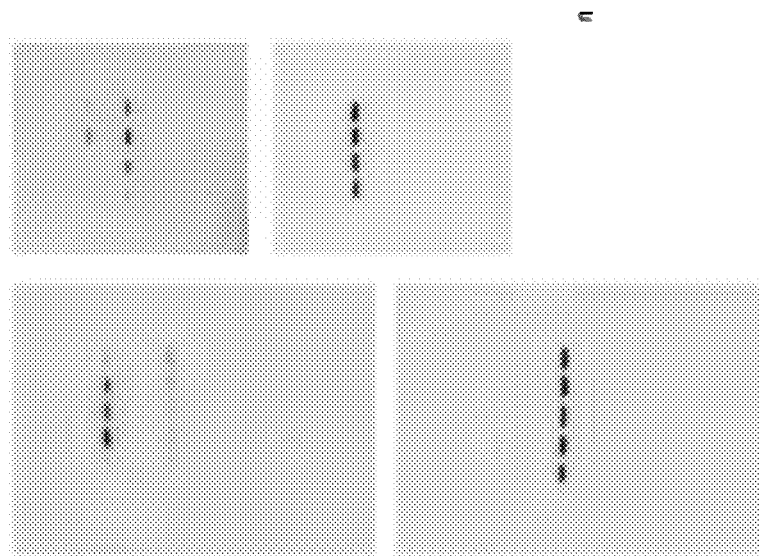
Figure 15H:
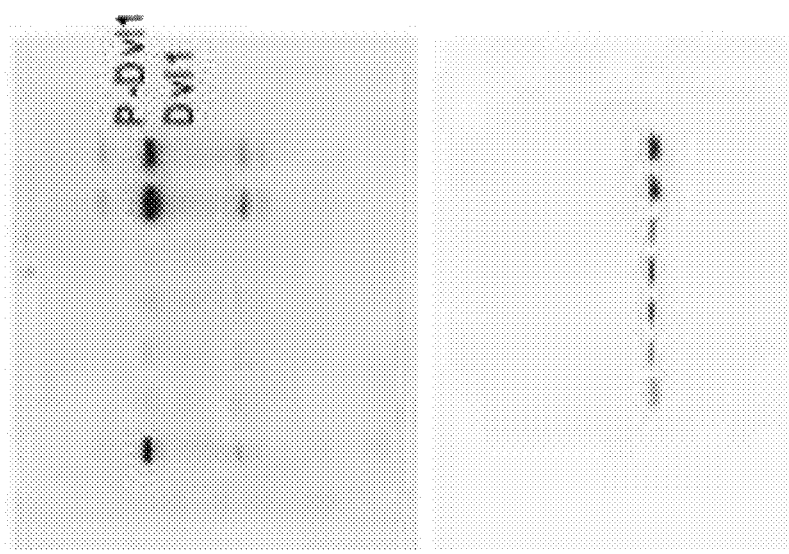
Figure 15J:
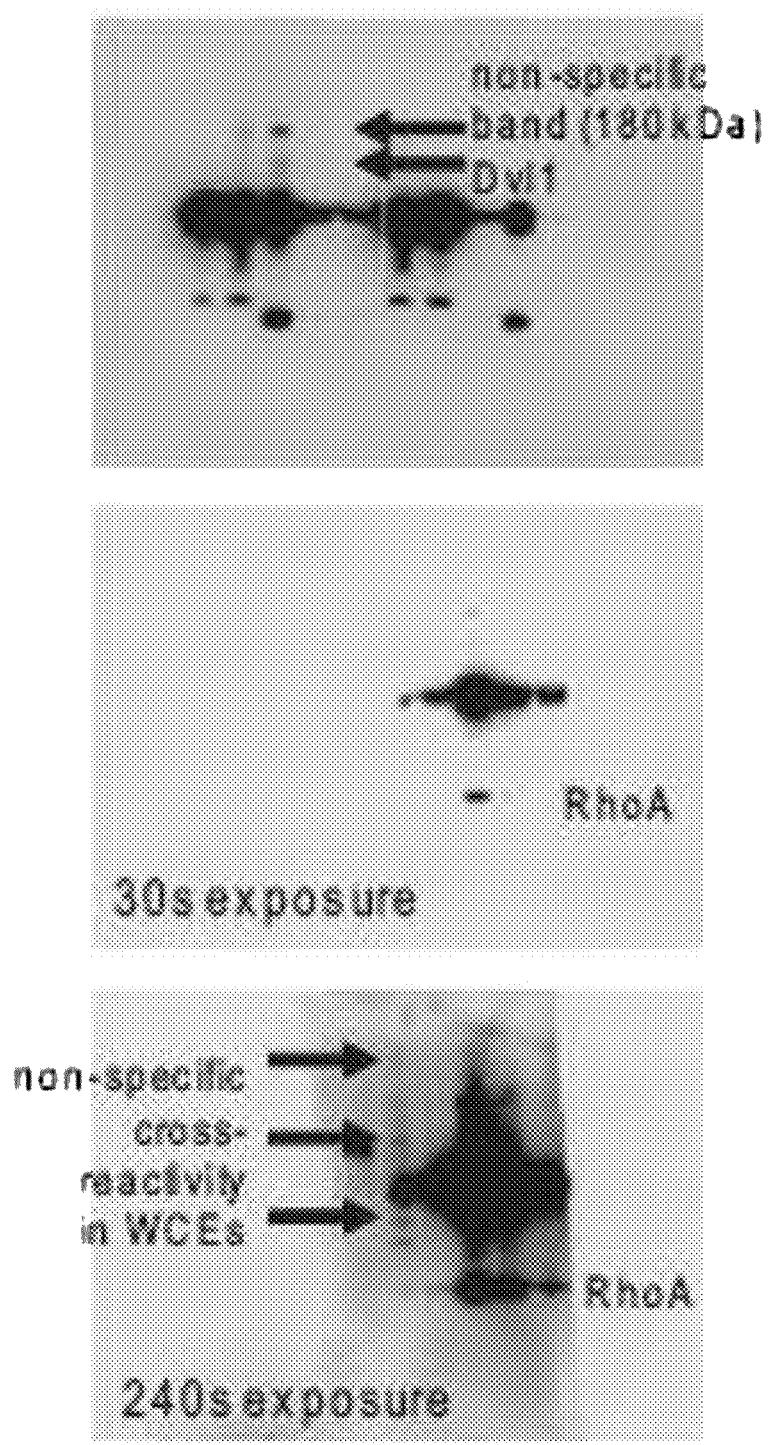

FIG. 14 illustrates RT-PCR analysis of effectiveness of Tmem216 siRNA. Tmem216 was amplified for various cycles from IMCD3 cells (–ve: absent reverse transcriptase). Tmem216 was detectable following scrambled siRNA, but not readily detectable following Tmem216 siRNA1. M=ladder marker, Hprt gene was used as a positive amplification control.

FIG. 15A-J illustrate full scans of Western blot data generated as discussed above.

The drawings set forth herein are illustrative of embodiments of the invention and are not meant to limit the scope of the invention as encompassed by the claims. Like reference symbols in the various drawings indicate like elements.

Reference will now be made in detail to various exemplary embodiments of the invention, examples of which are illustrated in the accompanying drawings. The following detailed description is provided to give the reader a better understanding of certain details of aspects and embodiments of the invention, and should not be interpreted as a limitation on the scope of the invention.

DETAILED DESCRIPTION

In alternative embodiments, the invention provides compositions and methods for the identification of genetic polymorphic variations in the human TMEM216 gene, and methods of using the identified genetic polymorphisms. In alternative embodiments, the invention provides isolated, synthetic or recombinant polypeptides that are human TMEM216 variants, and nucleic acids encoding these human TMEM216 variant proteins.

Abbreviations and Definitions

To facilitate understanding of the invention, a number of terms and abbreviations as used in alternative embodiments are defined as follows:

In alternative embodiments, the terms "genetic variant," "mutation," and "nucleotide variant" are used herein interchangeably to refer to changes or alterations to a reference TMEM216 gene sequence at a particular locus, including, but not limited to, nucleotide base deletions, insertions, inversions, and substitutions in the coding and noncoding regions. Deletions may be of a single nucleotide, a portion or a region of the nucleotide sequence of the gene, or of the entire gene sequence. Insertions may be of one or more nucleotides. The genetic variants may occur in transcriptional regulatory regions, untranslated regions of mRNA, exons, introns, or exon/intron junctions. The genetic variants may or may not result in stop codons, frame shifts, deletion of amino acids, altered amino acid sequence, or altered protein expression level. The mutations or genetic variants can be somatic, i.e., occur only in certain tissues of the body and are not inherited in the germline, or germline mutations, i.e., inherited mutations found in all tissues.

In alternative embodiments, "Genetic polymorphism" as used herein refers to the phenomena that two or more genetic variants in a particular locus of a gene are found in a population.

In alternative embodiments, the term "allele" or "gene allele" is used herein to refer generally to a naturally occurring gene having the reference sequence or a gene containing a specific genetic variant.

In alternative embodiments, the term "TMEM216 nucleic acid" means a nucleic acid molecule the nucleotide sequence of which is found uniquely in a TMEM216 gene or a substantially equivalent form thereof. That is, the nucleotide sequence of a "TMEM216 nucleic acid" can be a full-length sequence of, or a portion found in, either TMEM216 genomic DNA or mRNA/cDNA, either wild-type or naturally existing variant TMEM216 gene, or an artificial nucleotide sequence encoding a wild-type TMEM216 protein or naturally existing polymorphic variant TMEM216 protein.

In alternative embodiments, the term "TMEM216 nucleic acid variant" refers to a naturally occurring TMEM216 nucleic acid.

In alternative embodiments, the term "amino acid variant" refers to amino acid changes to a reference TMEM216 protein sequence resulting from nucleotide variants or mutations to the reference gene encoding the reference TMEM216 protein. The term "amino acid variant" is intended to encompass not only single amino acid substitutions, but also amino acid deletions, insertions, and other changes of amino acid sequence in a TMEM216 protein that can indicate a susceptibility to Joubert Syndrome or other ciliopathies.

In alternative embodiments, the term "TMEM216 protein variant" is used herein relative to a reference TMEM216 protein to mean a TMEM216 protein found in a population that is the coding product of a TMEM216 gene allele containing genetic variants such as single nucleotide substitutions, insertions, deletions, and DNA rearrangements, which lead to alterations in the protein sequence of the protein variant.

In alternative embodiments, the term "locus" refers to a specific position or site in a nucleotide sequence of a gene, or amino acid sequence of a protein. Thus, there may be one or more contiguous nucleotides in a particular gene locus, or one or more amino acids at a particular locus in a polypeptide. Moreover, "locus" may also be used to refer to a particular position in a gene sequence where one or more nucleotides have been deleted, inserted, or inverted.

In alternative embodiments, the terms "polypeptide," "protein," and "peptide" are used herein interchangeably to refer to amino acid chains in which the amino acid residues are linked by peptide bonds or modified peptide bonds. The amino acid chains can be of any length of greater than two amino acids. Unless otherwise specified, the terms "polypeptide," "protein," and "peptide" also encompass various modified forms thereof. Such modified forms may be naturally occurring modified forms or chemically modified forms. Examples of modified forms include, but are not limited to, glycosylated forms, phosphorylated forms, myristoylated forms, palmitoylated forms, ribosylated forms, acetylated forms, and the like. Modifications also include intra-molecular crosslinking and covalent attachment of various moieties such as lipids, flavin, biotin, polyethylene glycol or derivatives thereof, and the like. In addition, modifications may also include cyclization, branching and cross-linking. Further, amino acids other than the conventional twenty amino acids encoded by genes may also be included in a polypeptide.

In alternative embodiments, the terms "primer," "probe," and "oligonucleotide" may be used herein interchangeably to refer to a relatively short nucleic acid fragment or sequence. They can be DNA, RNA, or a hybrid thereof, or chemically modified analogs or derivatives thereof. Typically, they are single-stranded. However, they can also be double-stranded having two complementing strands that can be separated apart by denaturation. In certain aspects, they are of a length of from about 8 nucleotides to about 200 nucleotides, preferably from about 12 nucleotides to about 100 nucleotides, and more preferably about 18 to about 50 nucleotides. They can be labeled with detectable markers or modified in any conventional manners for various molecular biological applications.

In alternative embodiments, the term "isolated," when used in reference to nucleic acids (which include gene sequences or fragments) of this invention, is intended to mean that a nucleic acid molecule is present in a form other than found in nature in its original environment with respect to its association with other molecules. For example, since a naturally existing chromosome includes a long nucleic acid sequence, an "isolated nucleic acid" as used herein means a nucleic acid molecule having only a portion of the nucleic acid sequence in the chromosome but not one or more other portions present on the same chromosome. Thus, for example, an isolated gene typically includes no more than 25 kb of naturally occurring nucleic acid sequence which immediately flanks the gene in the naturally existing chromosome or genomic DNA. However, it is noted that an "isolated nucleic acid" as used herein is distinct from a clone in a conventional library such as genomic DNA library and cDNA library in that the clones in a library are still in admixture with almost all the other nucleic acids in a chromosome or a cell. In alternative embodiments, a nucleic acid of the invention can be in a vector, a plasmid, an expression vector and the like.

In alternative embodiments, the term "isolated nucleic acid" comprises "purified nucleic acid" which means a specified nucleic acid is in a substantially homogenous preparation of nucleic acid substantially free of other cellular components, other nucleic acids, viral materials, or culture medium, or chemical precursors or by-products associated with chemical reactions for chemical synthesis of nucleic acids. A "purified nucleic acid" can be obtained by standard nucleic acid purification methods. In alternative embodiments, for a purified nucleic acid, the specified nucleic acid molecule constitutes at least 15 percent of the total nucleic acids in the preparation. The term "purified nucleic acid" also means nucleic acids prepared from a recombinant host cell (in which the nucleic acids have been recombinantly amplified and/or expressed), or chemically synthesized nucleic acids.

In alternative embodiments, the term "isolated nucleic acid" also encompasses a "recombinant nucleic acid" which is used herein to mean a hybrid nucleic acid produced by recombinant DNA technology having the specified nucleic acid molecule covalently linked to one or more nucleic acid molecules that are not the nucleic acids naturally flanking the specified nucleic acid. Typically, such nucleic acid molecules flanking the specified nucleic acid are no more than 50 kb. In addition, the specified nucleic acid may have a nucleotide sequence that is identical to a naturally occurring nucleic acid, or a modified form, or mutant form thereof having one or more mutations such as nucleotide substitution, deletion/insertion, inversion, and the like.

In alternative embodiments, "isolated nucleic acid" further includes a chemically synthesized nucleic acid having a naturally occurring nucleotide sequence or an artificially modified form thereof (e.g., dideoxy forms).

In alternative embodiments, the term "isolated polypeptide" means a polypeptide molecule is present in a form other than found in nature in its original environment with respect to its association with other molecules. The term "isolated polypeptide" encompasses a "purified polypeptide" which is used herein to mean that a specified polypeptide is in a substantially homogenous preparation, substantially free of other cellular components, other polypeptides, viral materials, or culture medium, or when the polypeptide is chemically synthesized, substantially free of chemical precursors or by-products associated with the chemical synthesis. For a purified polypeptide, preferably the specified polypeptide molecule constitutes at least 15 percent of the total polypeptide in the preparation. A "purified polypeptide" can be obtained from natural or recombinant host cells by standard purification techniques, or by chemical synthesis.

In alternative embodiments, the term "isolated polypeptide" also encompasses a "recombinant polypeptide," which is used herein to mean a hybrid polypeptide produced by recombinant DNA technology or chemical synthesis having a specified polypeptide molecule covalently linked to one or more polypeptide molecules which do not naturally link to the specified polypeptide.

In alternative embodiments, "haplotype" is a combination of genetic (nucleotide) variants in a region of an mRNA or a genomic DNA on a chromosome found in an individual. Thus, a haplotype includes a number of genetically linked polymorphic variants that are typically inherited together as a unit.

In alternative embodiments, the term "reference sequence" refers to a polynucleotide or polypeptide sequence known in the art, including those disclosed in publicly accessible databases (e.g., GenBank), or a newly identified gene sequence, used simply as a reference with respect to the variants provided in the invention. The nucleotide or amino acid sequence in a reference sequence is contrasted to the alleles disclosed in the invention having newly discovered nucleotide or amino acid variants.

Genetic Polymorphic Variations in the TMEM216 Gene

The invention is based on the discovery of a number of polymorphisms in human Transmembrane Protein 216 ("TMEM216"), a gene identified on the basis of its genetic linkage to Joubert Syndrome and Related Disorders (JSRD) and Meckel Syndrome (MKS), particularly in the Ashkenazi Jewish population. A detailed description of the newly discovered polymorphisms is provided in Table 1, below (for example, c.G218T; p.R73L).

These polymorphisms are believed to be deleterious and cause significant alterations in structure or biochemical activities in the TMEM216 gene products expressed from mutant TMEM216 genes. Patients with such polymorphisms in one of their TMEM216 genes are predisposed to, and thus have a significantly increased likelihood of, having JSRD and MKS: or have one of these conditions. Therefore, the polymorphisms of this invention are useful in genetic testing as markers for the prediction of predisposition to ciliopathies, including JSRD and MKS.

The inventors discovered that the great majority, if not all, Ashenazi Jewish patients with Joubert syndrome share a common mutation (c.G218T; p.R73L) in this new gene TMEM216. Of 12 Jewish families tested, 100% of the patients were homozygous for the G218T mutation. These families exhibit phenotypically the classical form of Joubert Syndrome (which includes the neuroradiological hallmark molar tooth image (MTI), hypotonia, mental retardation, abnormal breathing and ocular motor apraxia). Additionally, retinal involvement was seen in 25% of Jewish patients and kidney involvement was seen in 17% of Jewish patients. This makes it possible to perform genetic testing in this population very easily. Other mutations at the R73 amino acid account for disease in other isolated populations, e.g., R73L. R73H and R73C.

Figure 2A:
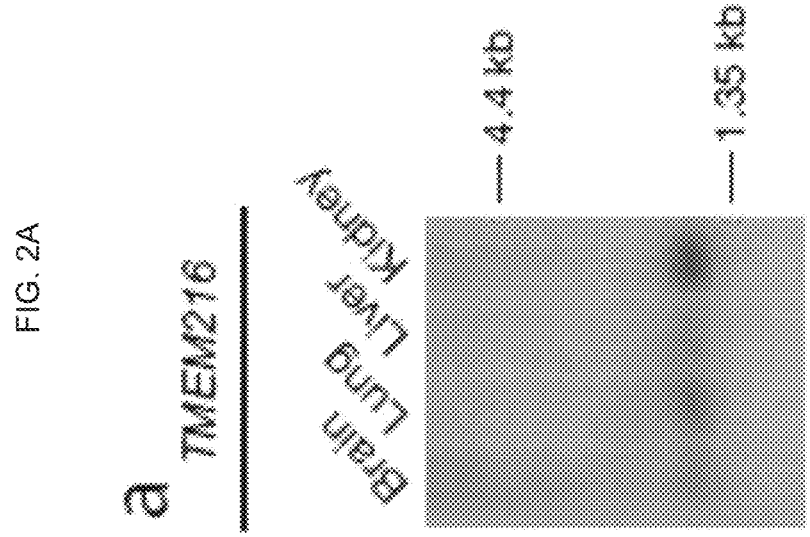
Figure 2B:
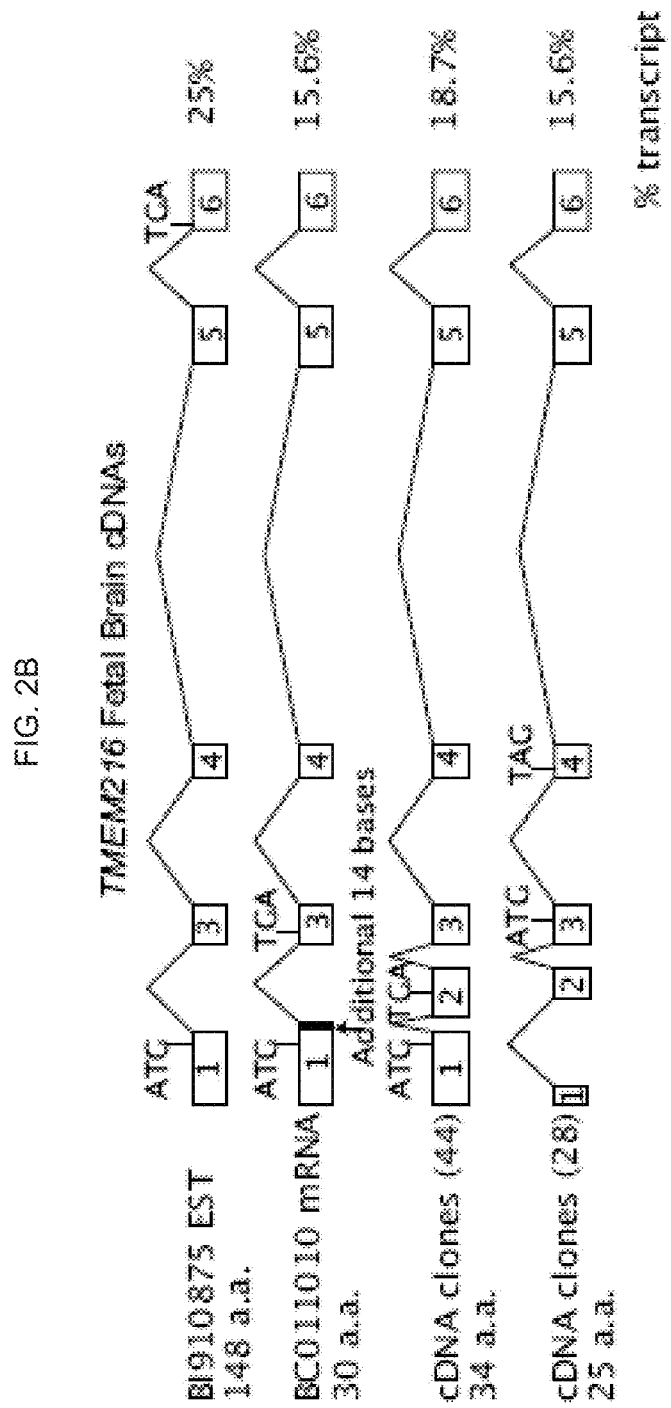

In alternative embodiments, the invention provides 4 major splice isoforms, the longest and most prevalent encoding a protein of 148 amino acid (aa) (SEQ ID NO: 1); encoded by an RNA structure having a sequence SEQ ID NO:3, which is considered to be the full-length mRNA. TMEM216 genomic organization is schematically illustrated in FIG. 2b.

Figure 2I:
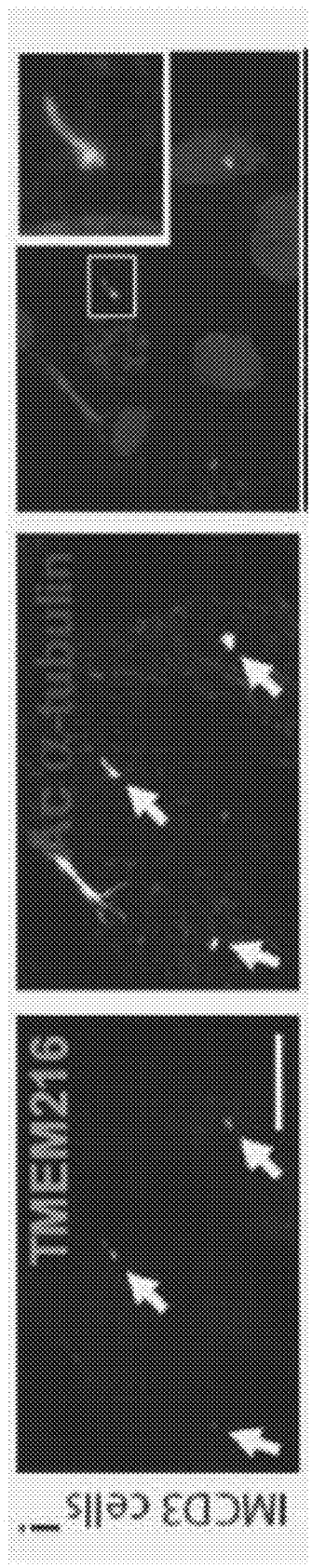
Figure 2J:
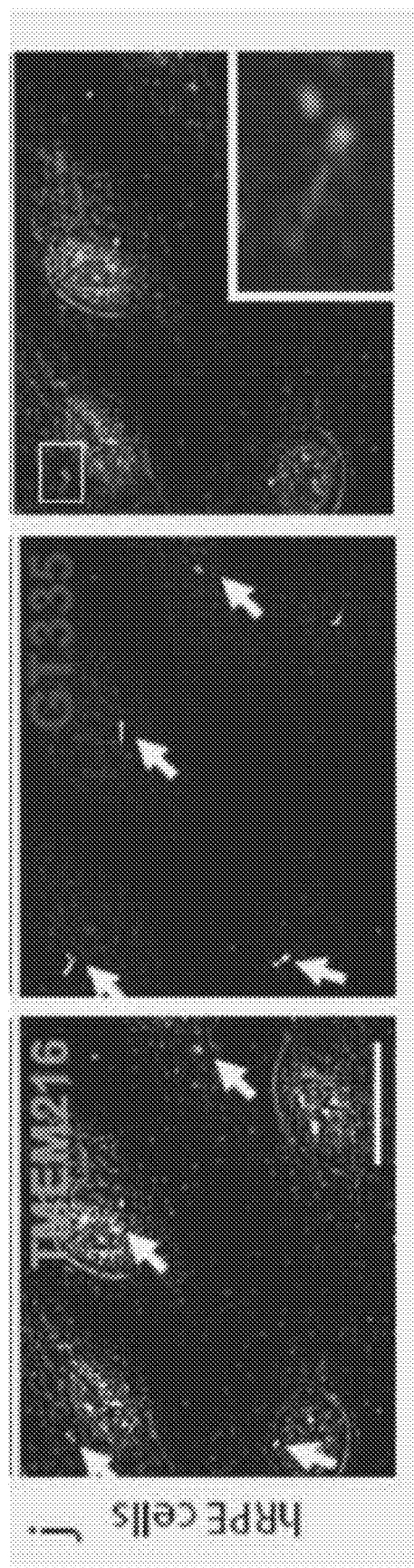

In FIGS. 2i and 2j, the arrows are pointing to the location of the TMEM216 protein inside of culture cells. The protein is found to co-localize with known markers of cilia, including the Ac alpha-tubulin and the GT335 proteins. This data is generated using antibodies to report the localization of the proteins of interest. The antibodies react to the protein of interest in the cell and are labeled with a fluorescent color so that the protein of interest can be detected under the microscope.

TABLE 1

Clinical and molecular data of TMEM216 mutated families.

| | Family data | | | | | | | Genetic data | |
|---|---|---|---|---|---|---|---|---|---|
| | Age | | | | Clinical data | | | Nucleotide | Protein |
| Fam | (sex) | Origin | CNS | Eye | Kidney | Liver | Other | changes | alterations |
| | | | | Joubert syndrome related disorders | | | | | |
| COR000 | 11y, M | Italian | MTS | — | NPH | ELE | — | 218G > T | R73L |
| | 15y, F | | | — | NPH | — | | | |
| | 20y, F | | | — | NPH | — | | | |
| | 29y, M | | | — | NPH | — | | | |
| COR284 | 22y, F | Italian | MTS | | NPH | | | 218G > T | R73L |
| COR114 | 1m, M | Turkish | MTS | MicroC | N/A | N/A | PD | 218G > A | R73H |
| | 13w, M | | Ec | | CK | BDP | PD, BLB | | |
| F401 | N/A | New Zealand | MTS | + | NPH | N/A | N/A | 217C > T | R73C |
| | | | | | | | | 398T > G | L133X |
| COR076 | 1y, F fetus | Ashk | MTS, PMG | — | | | ToF | 218G > T | R73L |
| COR287 | 3m, M | Ashk | MTS | | | | PD | 218G > T | R73L |
| MTI005 | 13y, M | Euro | MTS | OMA | NPH? | — | CD | 218G > T | R73L |
| | 3y, F | | MTS | OMA | | — | CD | | |
| MTI161 | 4y, M | Ashk | MTS | OMA, Nys | — | — | PD, TT, MP | 218G > T | R73L |
| MTI214 | 4y, F | Ashk | MTS | OMA | — | — | CMD | 218G > T | R73L |
| MTI467 | fetus | Ashk | MTS, DWM | N/AA | — | — | PD, MOF CD, HYPT | 218G > T | R73L |
| MTI585 | 1y, F | Ashk | MTS | Co | ACMD | — | CMD | 218G > T | R73L |
| MTI658 | 8y, F | Ashk | MTS | Nys | NPH? | — | PD, CMD | 218G > T | R73L |
| | 5y, F | | MTS | Nys | NPH? | — | PD, CMD | | |
| | 2 fetuses | | | | N/A | | PD | | |
| MTI1006 | 9y, M | Ashk | MTS | OMA, Nys, | — | — | — | 218G > T | R73L |
| | 1y, M2 (cousin) | | MTS | OMA, Nys, | — | — | PD | | |
| MTI1008 | 4y, F | Ashk | MTS, DWM | OMA | N/A | N/A | RTP | 218G > T | R73L |
| | | | | Meckel syndrome | | | | | |
| F002 | MKS15 21w, M | Tunisian | Mc | | CK | BDP | PD, CP, BLB | 341T > G | L114R |
| | MKS16 14w, F | | An | | CK | BDP | PD, BLB | | |
| F005 | MKS74 24w, M | Tunisian | Mc | MicroO | CK | BDP | PD, CP, IUGR, BLB, HypoG | 341T > G | L114R |
| F56 | MKS491 N/A | Palestinian | An | | CK | N/A | | 230G > C | G77A→splice: |
| | MKS492 15w | | DW, Ec | | CK | N/A | IUGR | | T78KfsX30 |

TABLE 1-continued

Clinical and molecular data of TMEM216 mutated families.

| Fam | Age (sex) | Origin | CNS | Eye | Kidney | Liver | Other | Nucleotide changes | Protein alterations |
|---|---|---|---|---|---|---|---|---|---|
| F58 | MKS511 SB, M | Palestinian | Ec | | CK | BDP | PD, CP | 230G > C | G77A→splice: T78KfsX30 |
|  | MKS512 N/A | | Ec | | CK | BDP | PD | | |
| F154 | MKS1077 22wSB | Palestinian | Mc | | CK | N/A | | 230G > C | G77A→splice: T78KfsX30 |
| A2423 | 162 21w, M | British | Ec | — | CK | BDP | PD, CP, VSD, IM, BLB CH, Omph | 253C > T | R85X |
|  | 163 12w, M | | Ec | — | CK | — |  | | |

Legend:
ACMD: abnormal cortico-medullary differentiation;
An: anencephaly;
Ashk: Ashkenazi Jewish;
BDP: bile ducts proliferation;
BLB: bowing of long bones;
CD: clinodactyly;
CH: cystic hygroma;
CK: cystic kidneys;
CMD: camptodactyly;
Co: chorioretinal coloboma;
CP: cleft palate;
CVA: cerebellar vermis agenesis;
DW: Dandy-Walker malformation;
Ec: encephalocele;
ELE: elevated liver enzymes;
Euro: European;
F: female;
HypoG: hypoplastic external genitalia;
HYPT: hypertelorism;
IM: intestinal malrotation;
IUGR: intrauterine growth retardation;
M: male;
m: months;
IUGR: intrauterine growth retardation;
Mc: meningocele;
MEc: meningoencephalocele;
MOF: multiple oral frenulae;
MicroC: microcornea;
MicroO: microphthalmia;
MP: micropenis;
MTS: molar tooth sign;
N/A: not available;
NPH: nephronophthisis;
Nys: nystagmus;
OMA: oculomotor apraxia;
Omph: omphalocele;
PD: polydactyly;
PMG: polymicrogyria;
RTP: rhythmic tongue protrusions;
SB: stillbirth;
ToF: tetralogy of Fallot;
TT: tongue tumors;
VSD: ventricular septal defect;
w: gestational weeks;
y: years.

TABLE 1

Clinical and molecular data of TMEM216 mutated families.

| Fam | Age (sex) | Origin | CNS | Eye | Kidney | Liver | Other | Nucleotide changes | Protein alterations |
|---|---|---|---|---|---|---|---|---|---|
| Joubert syndrome related disorders | | | | | | | | | |
| COR000 | 11y, M | Italian | MTS | — | NPH | ELE | — | 218G > T | R73L |
|  | 15y, F | | | — | NPH | — | | | |
|  | 20y, F | | | — | NPH | — | | | |
|  | 29y, M | | | — | NPH | — | | | |

TABLE 1-continued

Clinical and molecular data of TMEM216 mutated families.

| Fam | | Age (sex) | Origin | CNS | Eye | Kidney | Liver | Other | Nucleotide changes | Protein alterations |
|---|---|---|---|---|---|---|---|---|---|---|
| COR284 | | 22y, F | Italian | MTS | | NPH | | | 218G > T | R73L |
| COR114 | | 1m, M | Turkish | MTS | MicroC | N/A | N/A | PD | 218G > A | R73H |
| MKS350 | | 13gw, M | New Zealand | Ec | | CK | BDP | PD, BLB | | |
| F401 | | N/A | | MTS | + | NPH | N/A | N/A | 217C > T | R73C |
| | | | | | | | | | 398T > G | L133X |
| COR076 | | 1y, F fetus | Ashk | MTS, PMG | — | — | | ToF | 218G > T | R73L |
| COR287 | | 3m, M | Ashk | MTS | | | | PD | 218G > T | R73L |
| MTI005 | | 13y, M | Euro | MTS | OMA | NPH? | — | CD | 218G > T | R73L |
| | | 3y, F | | MTS | OMA | | — | CD | | |
| MTI161 | | 4y, M | Ashk | MTS | OMA, Nys | — | — | PD, TT, MP | 218G > T | R73L |
| MTI214 | | 4y, F | Ashk | MTS | OMA | — | — | CMD | 218G > T | R73L |
| MTI467 | | fetus | Ashk | MTS, DWM | N/AA | — | — | PD, MOF CD, HYPT | 218G > T | R73L |
| MTI585 | | 1y, F | Ashk | MTS | Co | ACMD | — | CMD | 218G > T | R73L |
| MTI658 | | 8y, F | Ashk | MTS | Nys | NPH? | — | PD, CMD | 218G > T | R73L |
| | | 5y, F | | MTS | Nys | NPH? | — | PD, CMD | | |
| | | 2 fetuses | | | | N/A | | PD | | |
| MTI1006 | | 9y, M | Ashk | MTS | OMA, Nys, | — | — | — | 218G > T | R73L |
| | | 1y, M2 (cousin) | | MTS | OMA, Nys, | — | — | PD | | |
| MTI1008 | | 4y, F | Ashk | MTS, DWM | OMA | N/A | N/A | RTP | 218G > T | R73L |
| Meckel syndrome | | | | | | | | | | |
| F002 | MKS15 | 21gw, M | Tunisian | Mc | | CK | BDP | PD, CP, BLB | 341T > G | L114R |
| | MKS16 | 14gw, F | | An | | CK | BDP | PD, BLB | | |
| F005 | MKS74 | 24gw, M | Tunisian | Mc | MicroO | CK | BDP | PD, CP, IUGR, BLB, HypoG | 341T > G | L114R |
| F56 | MKS491 | N/A | Palestinian | An | | CK | N/A | | 230G > C | G77A→splice: T78KfsX30 |
| | MKS492 | 15gw | | DW, Ec | | CK | N/A | IUGR | | |
| F58 | MKS511 | SB, M | Palestinian | Ec | | CK | BDP | PD, CP | 230G > C | G77A→splice: T78KfsX30 |
| | MKS512 | N/A | | Ec | | CK | BDP | PD | | |
| F154 | MKS1077 | 22gw | Palestinian | Mc | | CK | N/A | | 230G > C | G77A→splice: T78KfsX30 |
| A2423 | 162 | 21gw, M | British | Ec | — | CK | BDP | PD, CP, VSD, IM, BLB | 253C > T | R85X |
| | 163 | 12gw, M | | Ec | — | CK | — | CH | | |

Legend:
ACMD: abnormal cortico-medullary differentiation;
An: anencephaly;
Ashk: Ashkenazi Jewish;
BDP: bile ducts proliferation;
BLB: bowing of long bones;
CD: clinodactyly;
CH: cystic hygroma;
CK: cystic kidneys;
CMD: camptodactyly;
Co: chorioretinal coloboma;
CP: cleft palate;
CVA: cerebellar vermis agenesis;
DW: Dandy-Walker malformation;
Ec: encephalocele;
ELE: elevated liver enzymes;
Euro: European;
F: female;
HypoG: hypoplastic external genitalia;
HYPT: hypertelorism;
IM: intestinal malrotation;
IUGR: intrauterine growth retardation;
M: male;
m: months;
IUGR: intrauterine growth retardation;
Mc: meningocele;
MEc: meningoencephalocele;
MOF: multiple oral frenulae;
MicroC: microcornea;
MicroO: microphthalmia;
MP: micropenis;
MTS: molar tooth sign;
N/A: not available;
NPH: nephronophthisis;

TABLE 1-continued

Clinical and molecular data of TMEM216 mutated families.

| | Family data | | | | Clinical data | | | | Genetic data | |
|---|---|---|---|---|---|---|---|---|---|---|
| Fam | Age (sex) | Origin | CNS | Eye | Kidney | Liver | Other | | Nucleotide changes | Protein alterations |

Nys: nystagmus;
OMA: oculomotor apraxia;
PD: polydactyly;
PMG: polymicrogyria;
RTP: rhythmic tongue protrusions;
SB: stillbirth;
ToF: tetralogy of Fallot;
TT: tongue tumors;
VSD: ventricular septal defect;
gw: gestational weeks;
y: years.

Nucleotide and Amino Acid Variants Tetraspan transmembrane proteins are characterized by four hydrophobic, putative transmembrane domains (TM1-TM4), forming two extracellular and one intracellular loop, which regulate signaling and trafficking properties of their partner proteins in multiple cellular contexts[1]. While little is known about their function, they can act with Wnt receptors[2], and their ability to form complexes with a wide variety of membrane and cytosolic proteins[3], suggests that they may participate in the formation of membrane domains that regulate signaling and sorting processes.

The neurological features of JSRD include hypotonia, ataxia, psychomotor delay, irregular breathing pattern and oculomotor apraxia and are variably associated with multiorgan involvement, mainly retinal dystrophy, nephronophthisis (NPH) and congenital liver fibrosis. JSRD are genetically heterogeneous, and all known genes encode for proteins localized at or near the primary cilium[4]. The JBTS2 (also known as CORS2) locus was mapped to chromosome 11p12-q13.3 in a large Sicilian family and in three consanguineous pedigrees from the Middle East[5,6]. Aligning the two datasets suggested a minimal candidate interval between D11S1344 and D11S1883 (46.123-63.130 Mb) 7 (FIG. 1a).

Figure 6A:
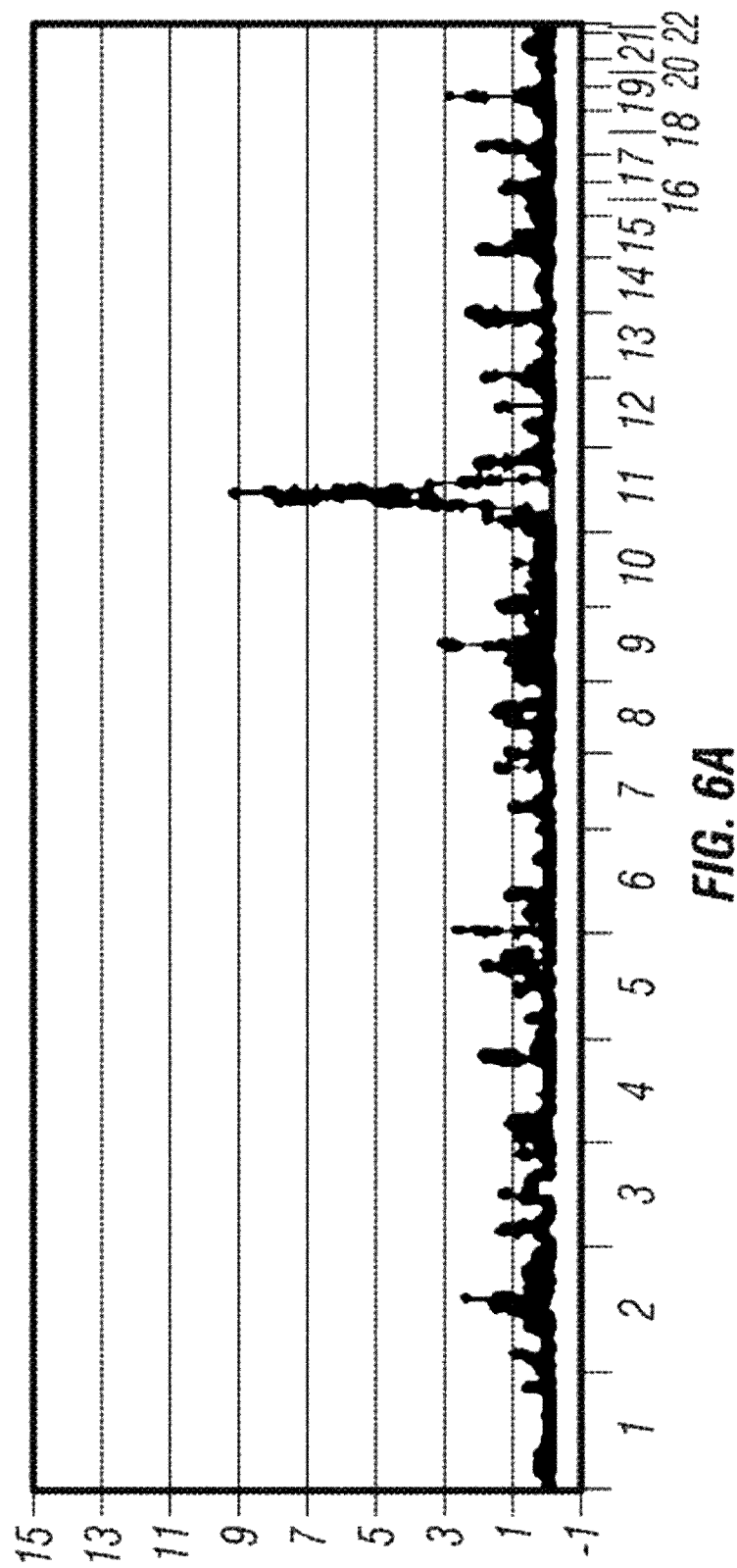

In addition to occipital encephalocele, MKS patients display other posterior fossa defects, cystic dysplastic kidneys, hepatic bile duct proliferation, and polydactyly, which overlap with JSRD, and the two conditions are known to be allelic at four loci[8-11]. The MKS2 locus was initially mapped in families of North African and Middle Eastern ancestry chromosome 11q to a region telomeric to JBTS2[12], but our subsequent identification of additional families, as well as SNP re-analysis of the initial families indicated allelism with JBTS2 between rs 113480 and rs953894 (48.014-62.518 Mb). (FIG. 6). Because JSRD and MKS are considered ciliopathies, of the 200 total candidate genes, the exons and splice sites of genes listed in the cilia proteome databases[13-14] were sequenced from one affected from each JBTS2/MKS2 family, but no mutations were identified.

Transmembrane proteins also represented attractive candidates, due to similarities to MKS3'TMEM67 encoding Meckelin, which is mutated both in JSRD and MKS[8,15]. Therefore the eight genes encoding transmembrane proteins were sequenced, eventually identifying homozygous deleterious mutations in TMEM216 in six of the 12 JSRD/MKS families compatible with linkage to the locus. The residue p.R73 was mutated both in the Sicilian family with JSRD (COR00, p.R73L) and in a Turkish family, in which MKS and JSRD coexisted in the same sibship (COR114, p.R73H).

Figure 7B:
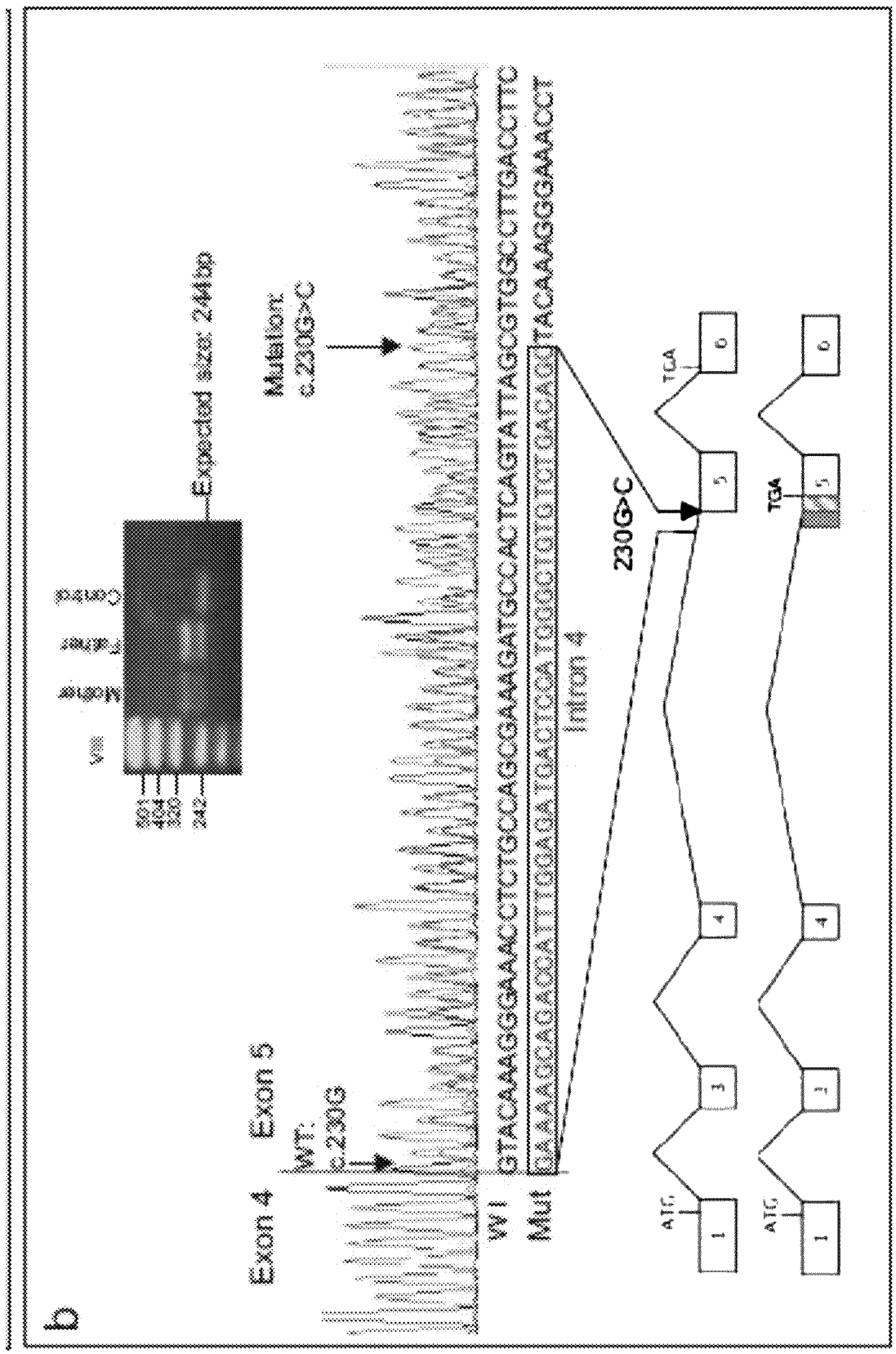

Two Tunisian families, not known to be related (F002, F005), carried the same p.L114R mutation, and two Palestinian families (F56, F58) carried the same p.G77A mutation. The p.G77A mutation resulted from a substitution (c.230G>C) affecting the first base of exon 5, thus possibly altering splicing. RT-PCR confirmed defective splicing (FIG. 7), leading to use of an alternative splice site in intron 4, the inclusion of an additional 46 bp and resultant premature protein termination (p.T78KfsX30). No mutations were identified in ethnically matched cohorts. These include 227 Italian and 109 Turkish (all wildtype at p.R73), 158 Palestinian and 112 Tunisian individuals, (all wildtype at p.G77 and p.L114). Additionally, all mutations were screened in 200 Central Asian (predominantly Pakistani), 200 European (predominantly British), as well as a cohort of 96 ethnically diverse individuals.

An additional 460 JSRD and 132 MKS probands were screened and mutations were identified in 12 and 2 further cases, respectively. Interestingly, 11 of 12 JSRD families shared the same homozygous p.R73L mutation, of which one family was also from Sicily and ten were of Ashkenazi Jewish descent. Additionally, a JSRD family from New Zealand was compound heterozygous for the missense change p.R73C and the truncating mutation p.L133X. Of the two mutated MKS families, one Palestinian family was also homozygous for the same splice site mutation p.G77A (T78KfsX30); and one British family with no known consanguinity had two affected fetuses carrying the homozygous truncating mutation p.R85X. Saturation of the region surrounding the p.R73L mutation with 17 SNP/microsatellite markers indicated that the Ashkenazi Jewish and the Sicilian families shared the same ancestral haplotype, spanning 472 Kb around the mutation (FIG. 8), and could be dated back at least 20 generations. Microsatellite analysis also detected shared haplotypes in the two Palestinian (F56, F58) and in the two Tunisian families (F002, F005), homozygous for the same mutations (FIG. 6).

Overall, 21 JSRD patients from 14 families and 10 MKS fetuses from 6 families carried TMEM216 mutations (FIG. 1b, Table 1). Among JSRD, the phenotype was characterized by frequent occurrence of NPH (9/21) and polydactyly (9/21), while retinal dystrophy and congenital hepatic fibrosis were never observed. In keeping with this, sequence analysis of 96 patients with Bardet-Biedl syndrome identified no mutations, since retinopathy is a key feature of this disease. However, two heterozygous changes p.L28F and p.R54C were identified, which were absent from 386 control chromosomes and were predicted to be evolutionarily intolerant, suggesting that TMEM216 might contribute epistatic alleles to BBS in a fashion similar to what has been observed for other MKS loci[16]. Of note, in two JS patients (MTI161 and MTI467) the polydactyly was associated with either tongue tumors or multiple oral frenula, corresponding to the Oro-Facio-Digital type VI (or Varadi-Papp) syndrome[17] (OMIM %277170), indicating that TMEM216 is the first known identified cause. In the 10 MKS fetuses with TMEM216 mutations, distinctive clinical features were skeletal dysplasia, including intrauterine growth retardation or bowing of the long bones in 7/11 fetuses, cleft palate in 4/11, and anencephaly in 2/11 (Table 1, FIG. 9), suggesting extreme pleiotrophic expressivity. Missense mutations predominated in JSRD patients whereas truncating or splice mutations predominated in MKS patients, suggesting that partially inactive but not null mutations may be compatible with survival.

All of the nonsynonymous changes occurred in evolutionarily conserved residues (FIG. 1c-d), and led to unstable protein when transfected into heterologous cells (FIG. 1e, FIG. 10). Although truncating mutations were identified in both the middle and end of the protein, p.R73 transversions predominated (FIG. 1c), with the p.R73L clearly a founder mutation. The carrier frequency in the Ashkenazi population was determined to be about 1:100, as two heterozygous healthy unrelated carrier individuals were identified among a screened cohort of 212 Ashkenazi individuals, making carrier detection possible at least in this population.

TMEM216 is a poorly annotated gene, with RefSeq predicting a protein of just 86 aa, suggesting potential alternative splicing. To characterize this mRNA Northern analysis was performed with a commercial human fetal blot, and found a single major mature isoform at about 1.4 Kb (FIG. 2a), agreeing with the predicted 1.3 Kb of the longest representative cDNAs. To interrogate splicing primers complementary to the furthest 5' and 3' regions of the known cDNA were designed, and sequenced 48 cloned PCR products from a 20 week gestation human fetal brain library. Four major splice isoforms were identified, the longest and most prevalent predicting a protein of 148 as (FIG. 2b), which is considered to be the full-length mRNA. There is a cryptic splice donor site in exon 1, which, when spliced to exon 3 (15.6%0/of clones) leads to a 30 aa protein. Furthermore, a cryptic exon 2 is spliced into the mature mRNA in over 30% of the recovered clones, but these two resultant mRNAs predict proteins of only 34 or 25 aa. Thus, there is extensive alternative splicing in relevant tissue, encoding for very short proteins, the functions of which were not evaluated further. No mutations were found in any of these cryptic coding regions.

TMEM216 contains a transmembrane 17 superfamily domain, also contained in TMEM17 and TMEM80, the only two proteins with similar homology. Based on this sequence similarity, mutations were tested in the predicted full length TMEM17 and TMEM80 genes among a cohort of 96 JS patients and 60 MKS patients, but found no mutations, suggesting a unique role of TMEM216 in these diseases.

Figure 6C:
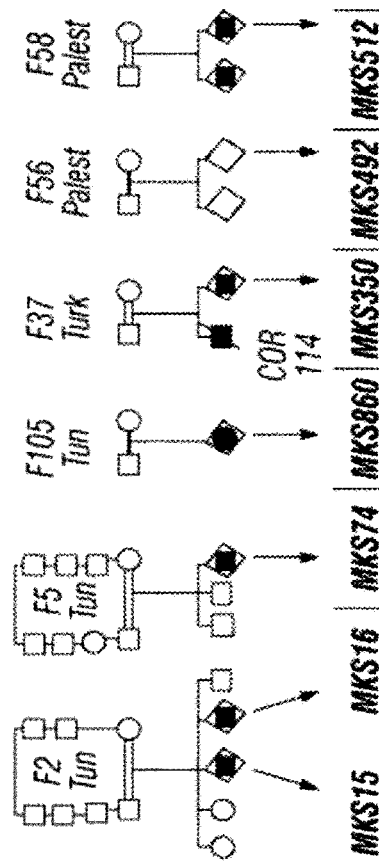

To elucidate potential physiological roles for TMEM216 in human development, its expression was examined in human embryonic tissues. In situ hybridization analysis in human embryos confirmed its ubiquitous expression (FIG. 2c-h) and may help explain the multi-organ involvement observed in these patients. In particular, expression was observed in the central nervous system, limb bud, kidney and cartilage, which is similar to the broad and relatively low-level expression pattern of other JSRD/MKS genes. An anti-TMEM216 polyclonal affinity-purified antibody was raised against amino acids 81-90, demonstrated specificity (FIG. 11), and immunostained two different ciliated cell lines (intramedullary collecting duct [IMCD3] and retinal pigment epithelium [hRPE]), used widely to study ciliary biology. Partial overlapping localization was observed with the primary cilium or adjacent basal body in the majority of cells, as marked by either acetylated or glutamylated tubulin staining (FIG. 2i-j), which was blocked by preincubation with the TMEM216 peptide (FIG. 11b, Supplemental FIG. 6b). TMEM216 antibody also reacted strongly in organs like fetal kidney containing ciliated cells (FIG. 11c, Supplemental FIG. 6c). Epitope tagged TMEM216 showed similar but more diffuse localization to cilia and other microtubule structures (i.e. mitotic spindle in cells undergoing late telophase, FIG. 12), suggesting TMEM216 may exert its effect on both cilia and other microtubule-based structures.

Figures 3A, 3B:
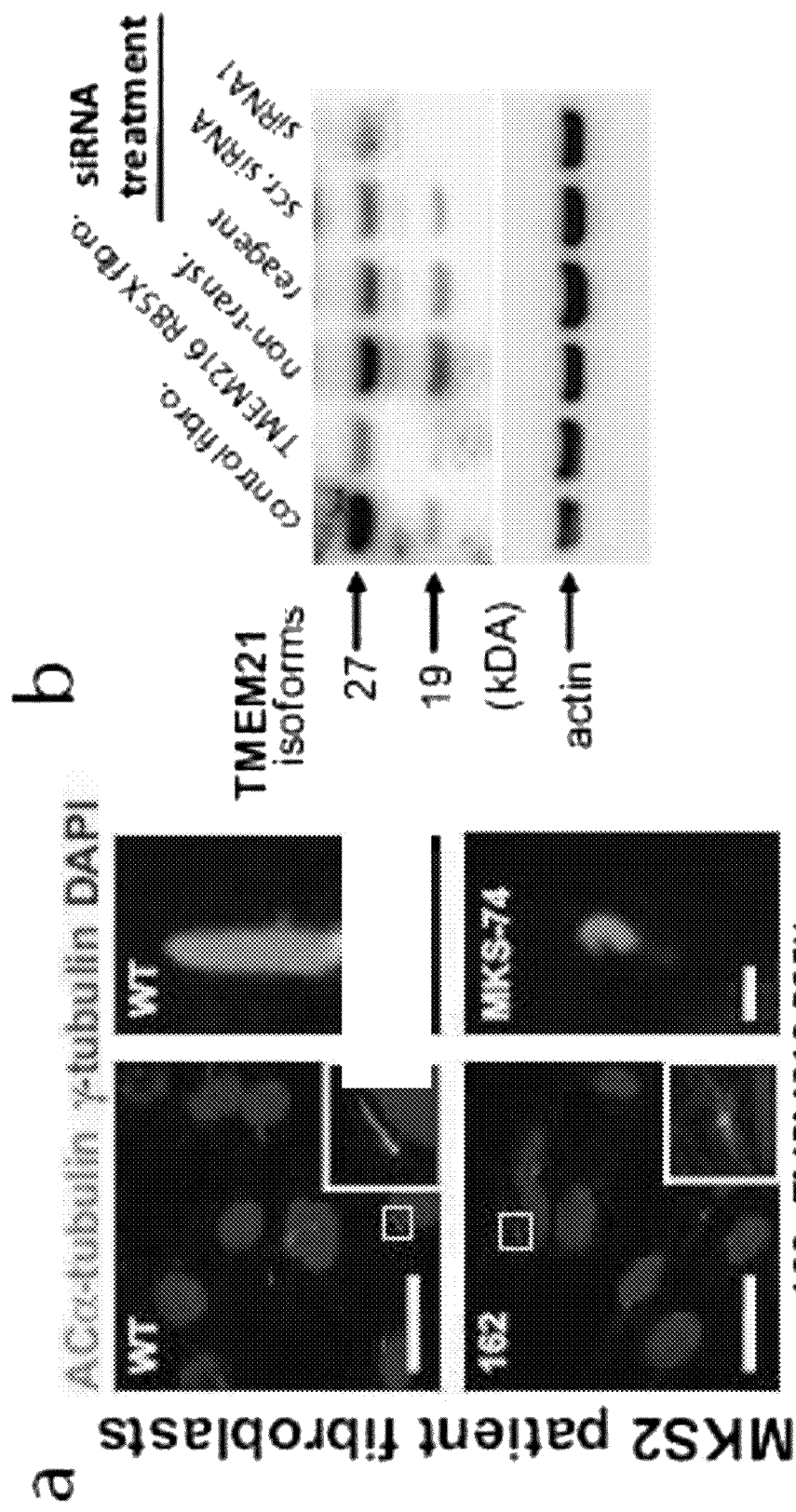
FIG. 3(a) illustrates immunostaining of two different TMEM216-mutated patient fibroblasts lines to show defective ciliogenesis and impaired centrosome docking (marked by γ-tubulin). Scale ba: left 20 um; right 1 um.
FIG. 3(b) illustrates a Western blot showing the specificity of TMEM216 antiserum towards endogenous protein. Control fibroblasts show 27 and 19 kD bands, which are reduced in TMEM216 p.R85X fibroblasts (some residual is apparent likely due to read-through from geneticin treatment), as well as in siRNA1-treated IMCD3 cells (especially the 19 dK band). Fibro.=fibroblasts; Non-transf.=nontransfected; scr.=scrambled.
Figure 3C:
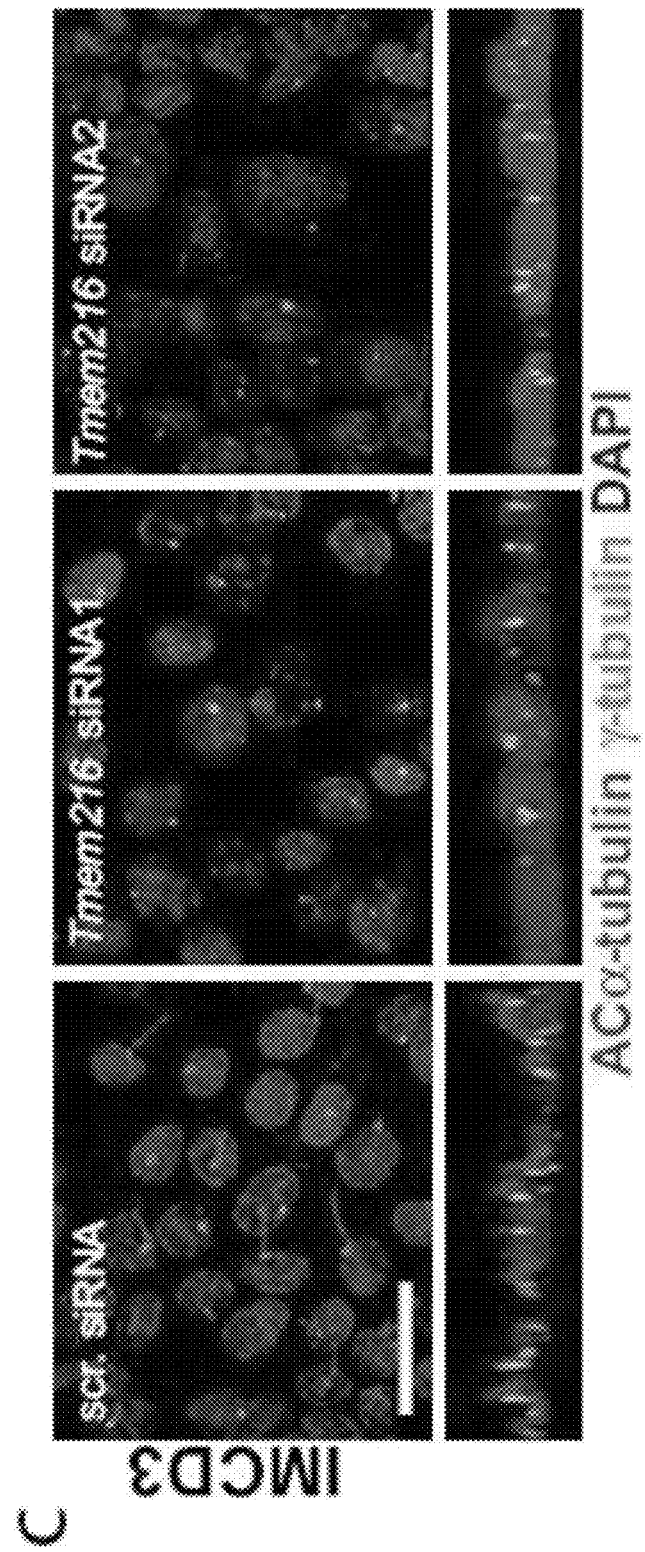
FIG. 3(c) illustrates cell staining of transfected IMCD3 cells showing effect of Tmem216 siRNA treatment, with reduced ciliogenesis and centrosome docking (note lack of cilia and lack of apically located centrosomes following knockdown) Top is x-y, and bottom is x-z projection, scale bar 10 um.
Figure 3D:
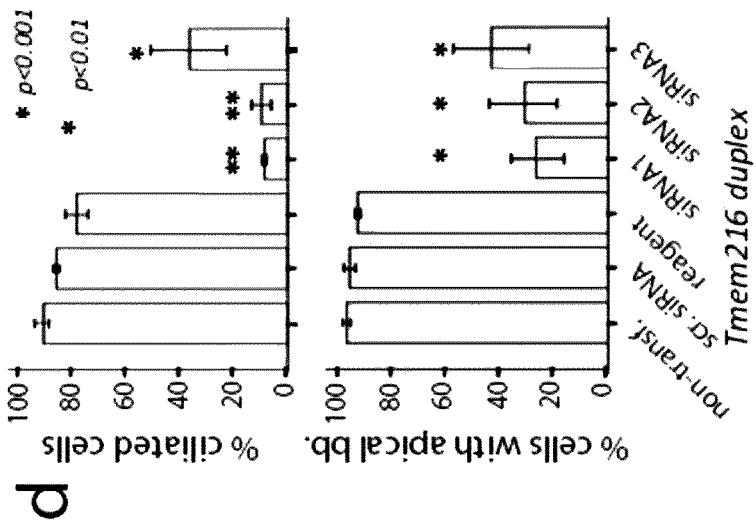
FIG. 3(d) graphically illustrates that the percent of ciliated cells (defined as cilia>1 um length) is reduced following Tmem216 siRNA treatment. Percent cells with apical basal bodies (defined as most superior 1.0 um sections compared to nuclear position) is similarly reduced. * p<0.01, ** p<0.001, chi-squared test.

In hTERT-immortalized fetal TMEM216 p.R85X homozygous mutant fibroblasts, a failure in ciliogenesis was noticed following 48 hr serum starvation (FIG. 3a) compared with controls. Acetylated microtubules in TMEM216-mutated fibroblasts also appeared disorganized. Western analysis of whole cell lysates from control fibroblasts identified two major TMEM216 isoforms of 19 and 27 kD (FIG. 3b) with the 19 kD band matching the predicted 148 as full length protein. No cDNAs were identified encoding a 27 kD protein despite comprehensive attempts to extend the ORF, and both were lost or attenuated (most notably the 19 kD isoform) in TMEM216 p.R85X fibroblasts from fetus 162, or following siRNA knockdown. Therefore transient transfection of monolayers was performed of the mouse ciliated cell line IMCD3 with two separate Tmem216 siRNA duplexes. Tmem216 knockdown prevented ciliogenesis in polarized cells, and blocked correct docking of centrosomes at the apical cell surface (FIG. 3c), as seen previously for Meckelin and MKS 1[18]. These data were quantified by analyzing the percent of cells with clearly evident cilia (defined as >1 um length) vs. those without cilia (defined as <1 um length), and by analyzing the percent of cells with apically positioned centrosomes (defined as the centrosome located apical to the nucleus). In cells in which Tmem216 was knocked down, striking defect was observed in both of these measurements compared with two separate control lines (FIG. 3d-e, chi-squared test, p<0.001, for 350 cells from each condition).

Figures 4A, 4B:
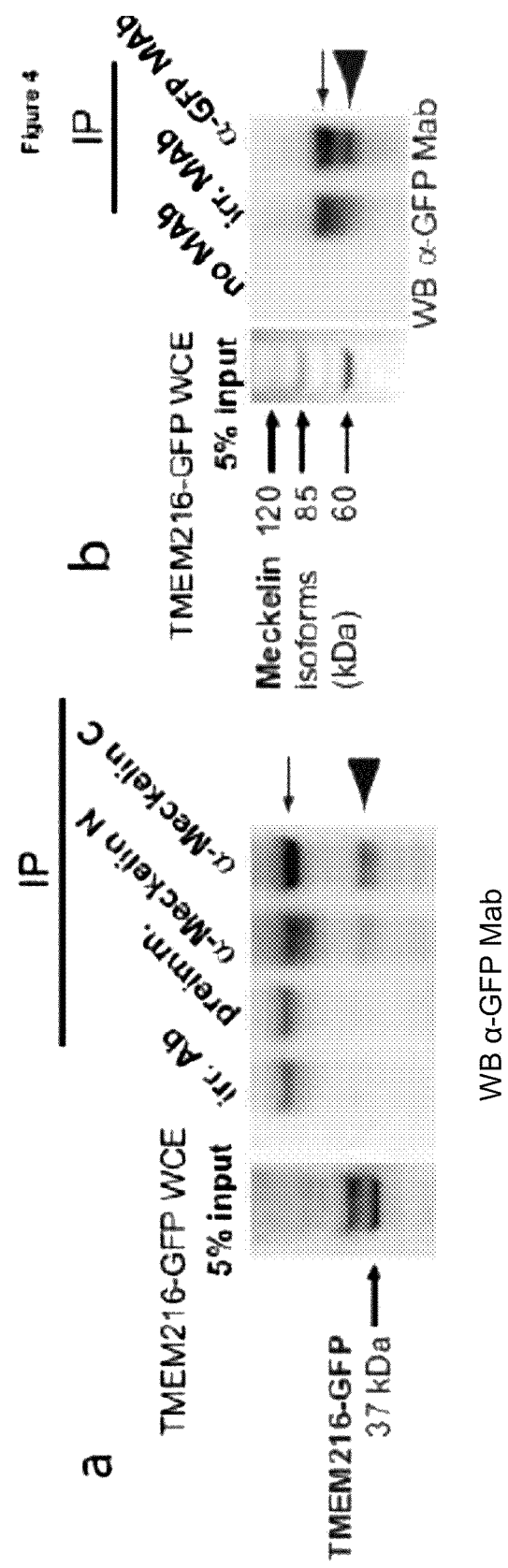

The similarities in cellular phenotypes of Mks3 and Tmem216 knockdown, and subcellular localizations of Meckelin and TMEM216, then prompted us to ask if the two proteins could interact. Lysates of cell transfected with GFP-tagged TMEM216 were immunoprecipitated with antibodies to either N- or C-terminal portions of Meckelin compared with negative controls, and then analyzed by Western for the presence of TMEM216. A complex between TMEM216 and Meckelin was observed using this assay (FIG. 4a). The complementary experiment was performed by immunoprecipitating the same lysates with GFP antibody compared with negative controls, and then analyzed by Western for the presence of Meckelin. No evidence of this complex was found (FIG. 4b), suggesting that TMEM216 can complex with Meckelin in cells.

Figure 4C:
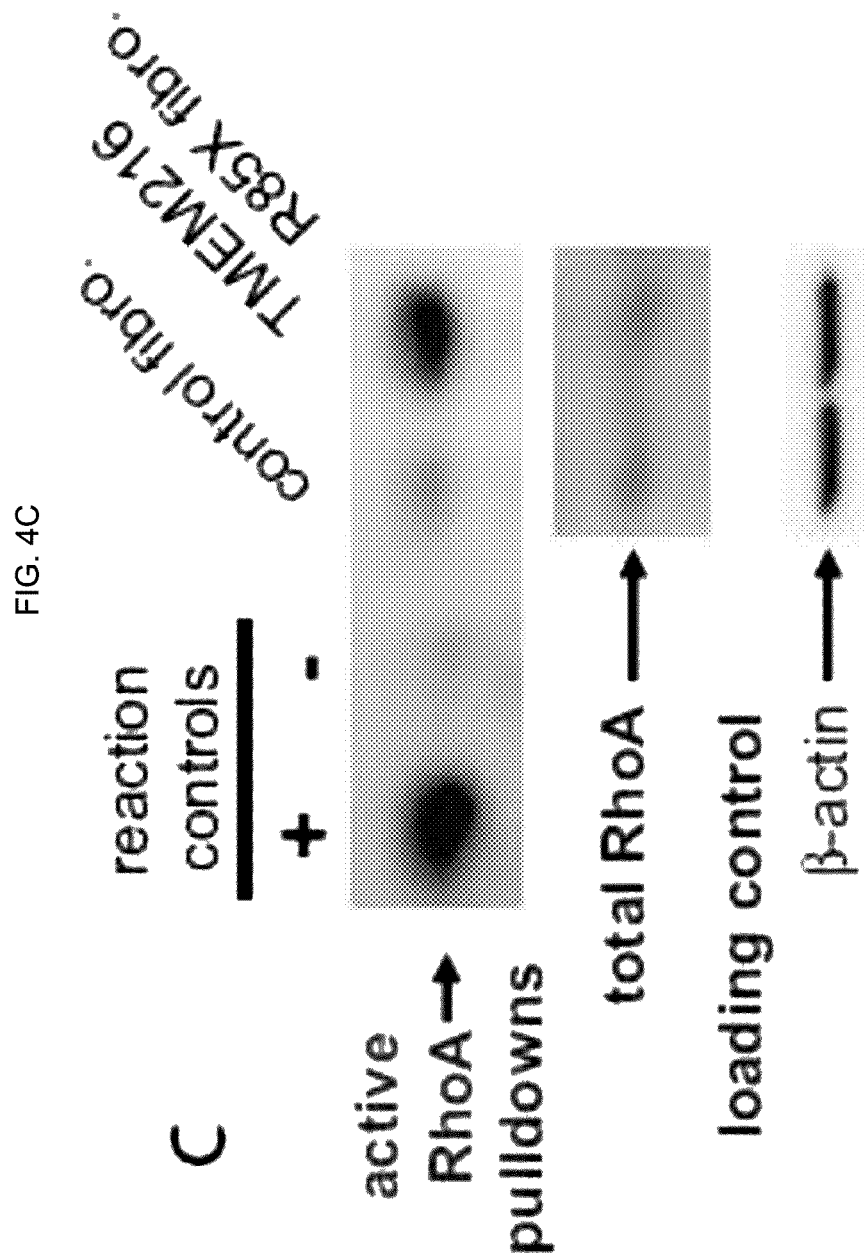
Figure 4D:
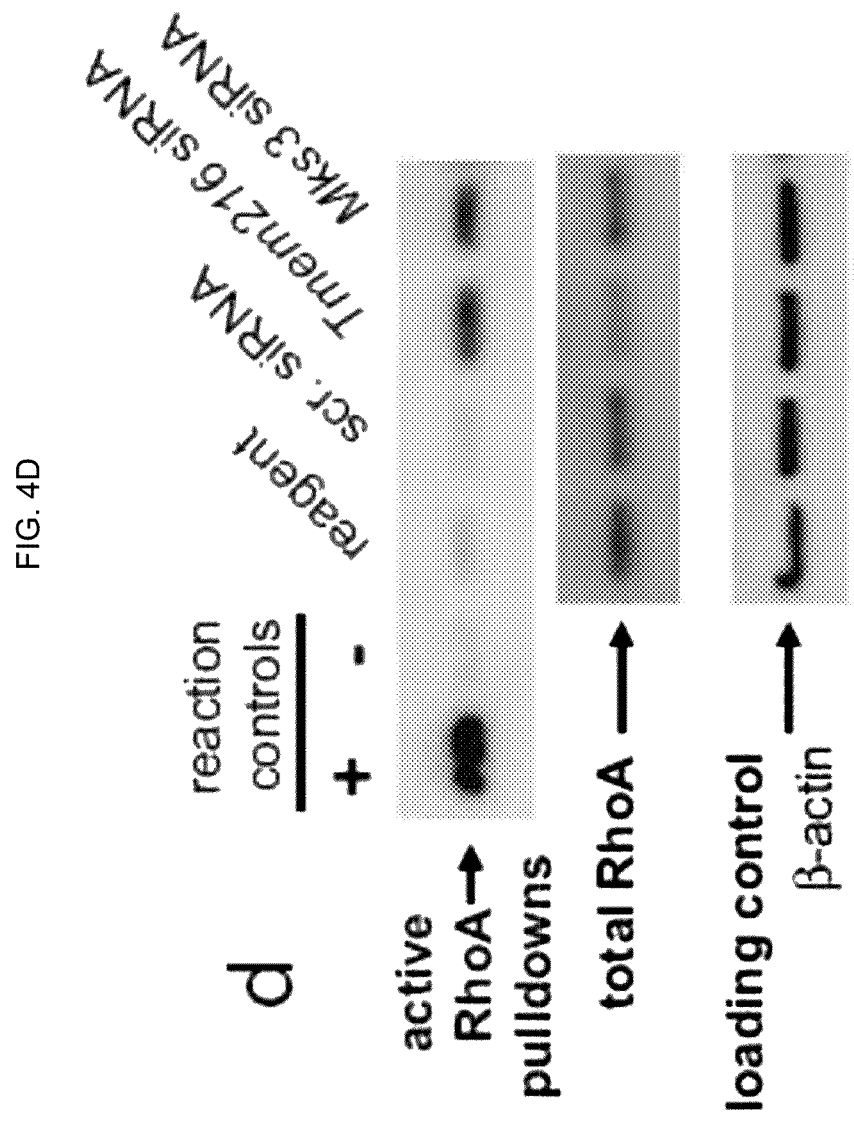
Figure 4F:
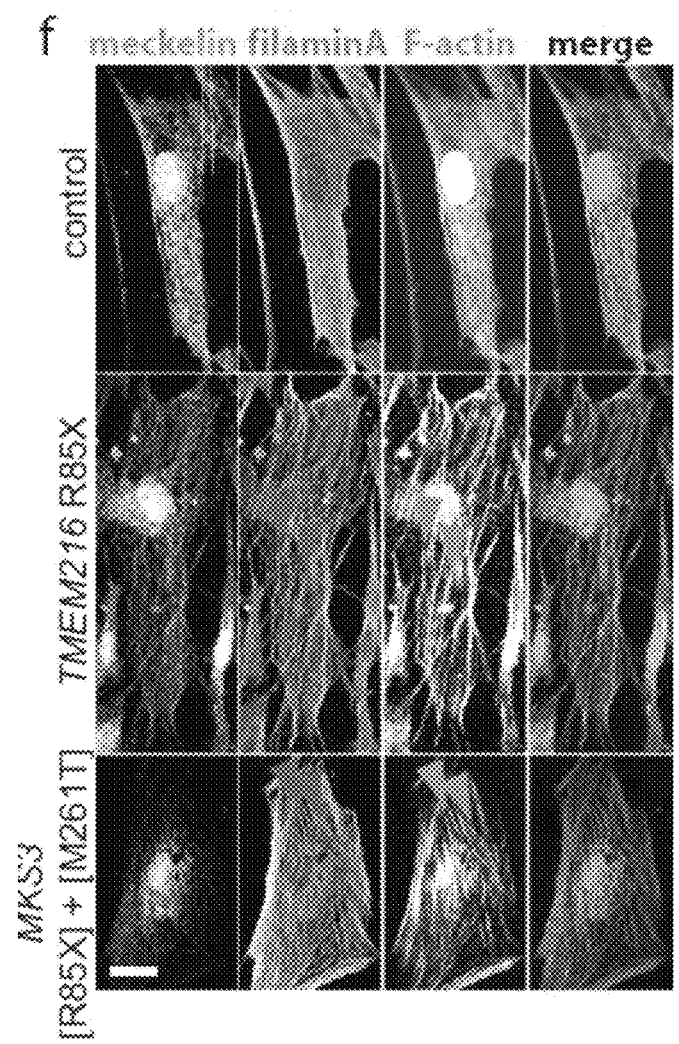

Many aspects of actin-dependent polarized cell behavior, including morphogenetic cell movements[19] and ciliogenesis[20] are mediated by the planar cell polarity (PCP) pathway of non-canonical Wnt signaling[21]. Therefore RhoA was first examined, since the Rho family of small GTPases are key mediators of this pathway[21,22]. Consistent with previous results for MKS3 patient fibroblasts or knockdown[23], it was found that RhoA signaling was hyperactive in both TMEM216 p.R85X fibroblasts or following Tmem216 knockdown (FIG. 4c-d), despite normal total amounts of RhoA in these cells. Since centrosome docking at the apical cell surface is prevented by the interruption of actin remodeling[24], and is dependent on both RhoA activation and regulation by the core PCP protein Dishevelled (Dvl)[25], it was therefore confirmed that RhoA is localized to the basal body in confluent IMCD3 cells (FIG. 4e). This result is consistent with previous findings that RhoA co-localizes with most basal bodies in multi-ciliated cells[25]. However, following Tmem216 knockdown for 24 hr, RhoA was mislocalized to peripheral regions of the basal body and to basolateral cell-cell contacts (FIG. 4e), consistent with translocation of ectopically-activated RhoA to the cytosol[26]. Tmem216 knockdown also showed evidence of a mislocalization of γ-tubulin at the centrosomei asal body for this timepoint, which suggests a defect in γ-tubulin nucleation, one of the earliest steps in ciliogenesis[27]. Mislocalization was not apparent at later timepoints (72 hr) in post-confluent cells. The established role of RhoA in modulating the actin cytoskeleton in the PCP pathway then led us to evaluate MKS2 patient fibroblast lines for alterations. A co-localization of actin stress fibers and the actin cross-linker filamin-A in the cytoplasm of these mutant cells was found, which was absent in control (FIG. 4f).

Figure 5C:
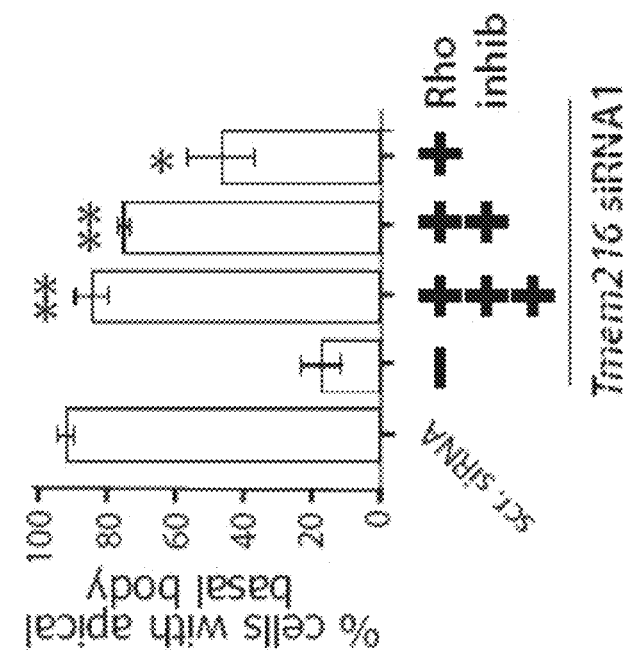
Figure 5B:
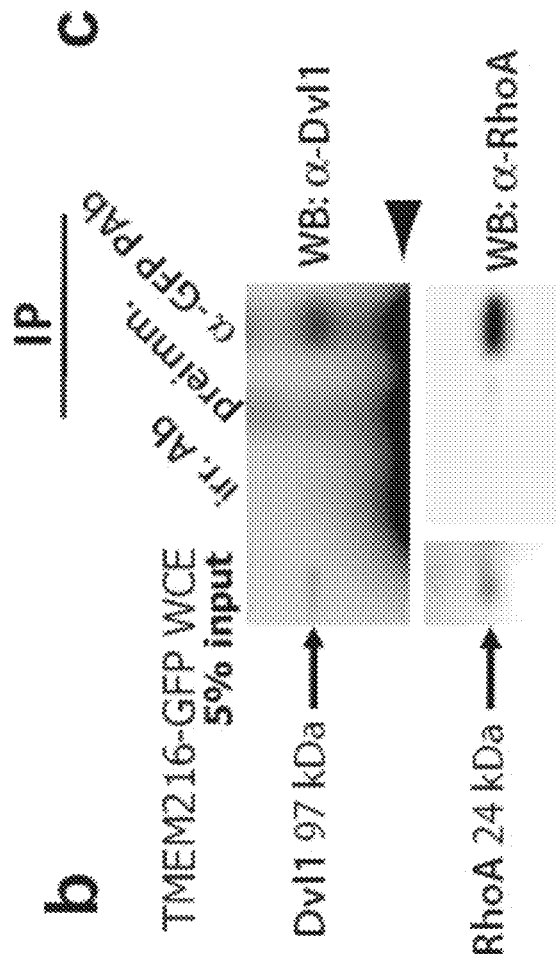

Dvl signaling in cells was looked at, since cilia negatively regulate Dvl activation[28], and Dvl mediates Rho activation at the apical surface of ciliated epithelial cells[25]. It was found that loss of TMEM216 (in both TMEM216 mutated cells and following Tmem216 knockdown) caused constitutive phosphorylation of Dvl1 (FIG. 5a, left panel), implying that TMEM216 modulates hyperresponsiveness of signaling pathways mediated by Dvl and RhoA. It was found that Rho inhibition also increased the Dvl1 phosphorylation in ciliated cells, implying the existence of feedback mechanism between Rho and Dvl (FIG. 5a, right panel). Unexpectedly, the constitutive Dvl1 phosphorylation associated with TMEM216 knockdown was blocked by Rho inhibition (FIG. 5a, right panel), suggesting that the loss of TMEM216 in ciliated cells can modify this feedback mechanism. Although this possibility warrants further investigation, our data nevertheless suggests a working model in which Dvl1, RhoA and TMEM216 may serve as part of a complex in the pericentrosomal compartment to mediate cellular polarization and centrosomal apical docking, and in support of this hypothesis, previous studies have shown that Dvl and Rho contribute to a core framework for regulating the apical docking of centrosomes[25]. Furthermore, it was observed evidence of a common complex containing TMEM216, Dvl1 and RhoA in TMEM216-transfected cells (FIG. 5b), and because there was no difference in the localization of Dvl1 following Tmem216 knockdown, this data predicts that the hyperactivation of Rho in the absence of TMEM216 might be responsible for the centrosome docking defect at the apical cellular surface. As expected, it was found that the impaired centrosome docking that was observed following Tmem216 knockdown was rescued in a dose-dependent fashion the using Rho inhibitor (FIG. 5c). High levels of this inhibitor (>2 ug/ml) impaired centrosome docking in normal siRNA-untreated IMCD3 cells, consistent with previous findings[24] (data not shown).

Figures 5D, 5E:
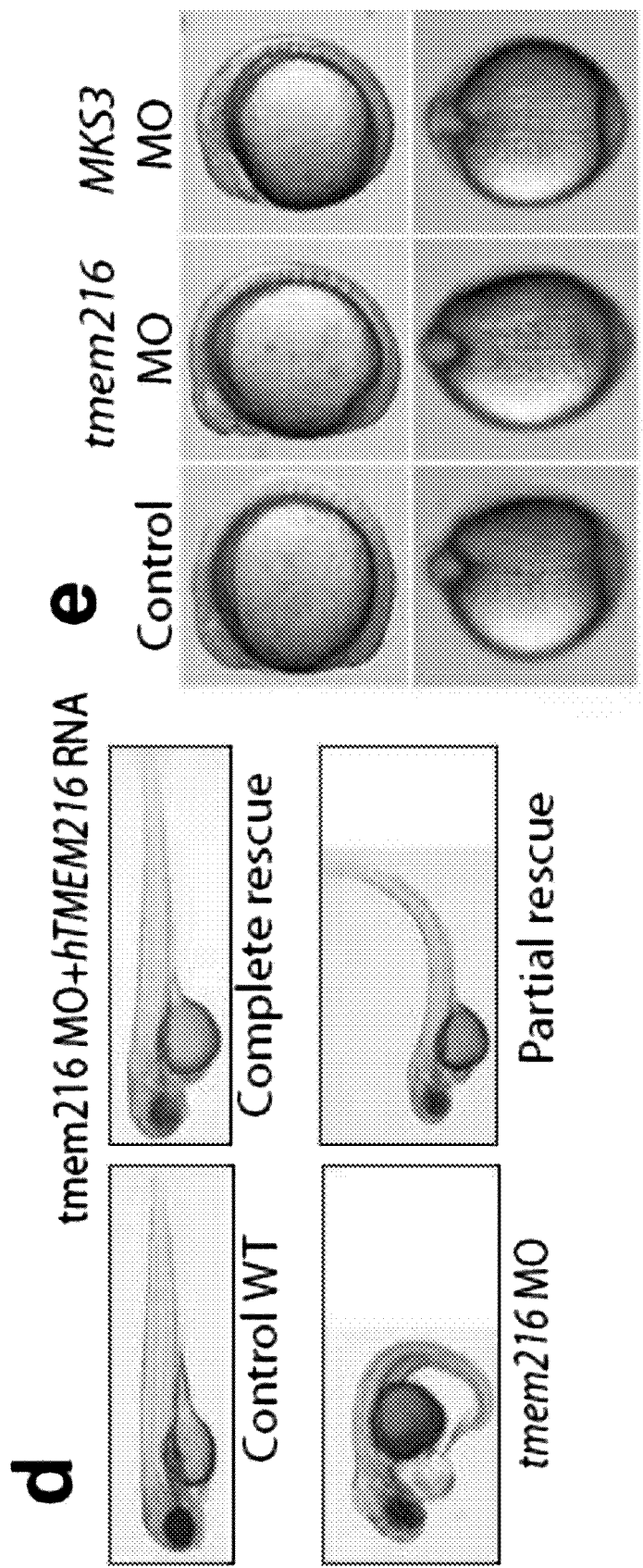
Figure 5F:
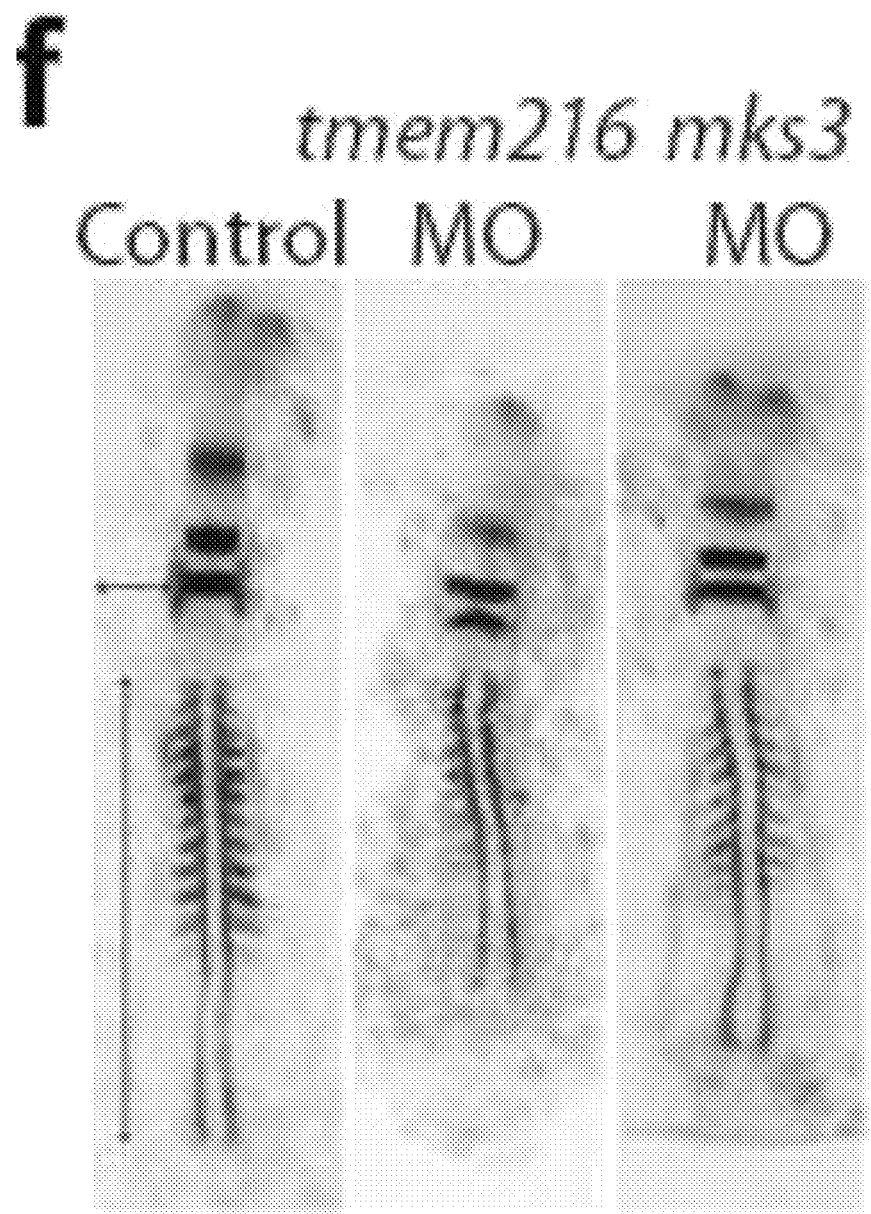
Figure 5G:
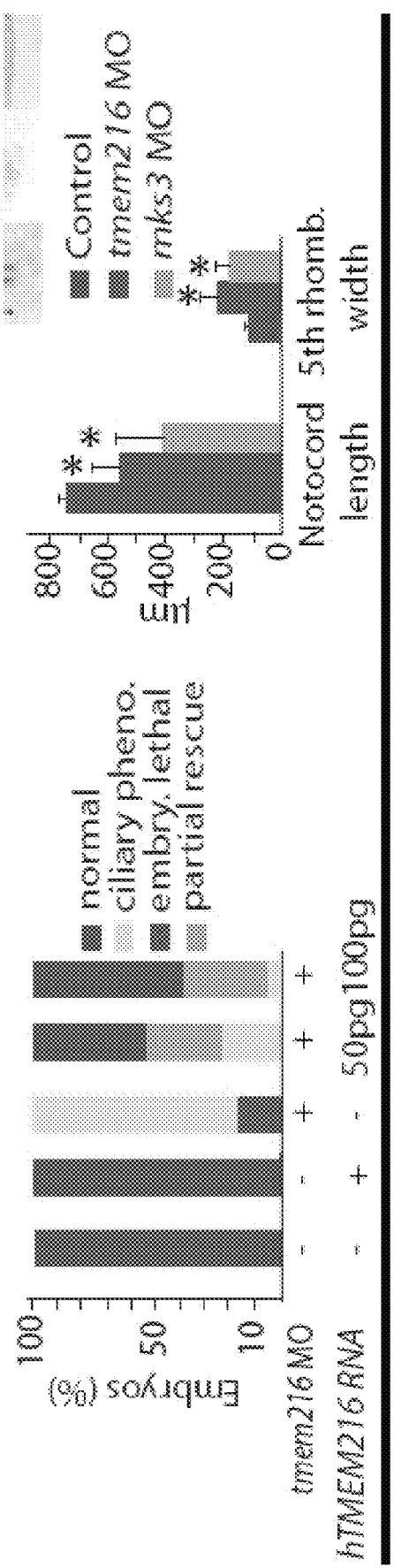

Meckelin is proposed to regulate centrosomal docking through the RhoA signaling pathway[23], and bears similarity to the Frizzled family of transmembrane Wnt receptors 15. Direct evidence of a role for Meckelin in PCP signaling stems from zebrafish embryo morphant phenotypes following morpholino knock-down of mks3[29]. These included defects in gastrulation movement (a shortened body axis, broad notochords and misshapen somites), which are typical of defects in non-canonical (PCP) Wnt signaling, and which have been observed in numerous ciliary and basal body morphants[29,30]. Strikingly similar phenotypes ciliary phenotypes was seen in tmem216 morphants, which are largely rescued by RNA encoding human TMEM216 (FIG. 5d), and fully rescued by RNA encoding nontargetable zebrafish tmem216 (not shown). Therefore the tmem216 and mks3 morphant phenotypes in zebrafish were compared, and noted similar defects in both live embryos and in embryros in which pronephric mesoderm, anterior neural structures, adaxial mesodermal cells, and somites were labeled with a krox20, pax2, and myoD riboprobe cocktail (FIG. 5e-f). Quantification (FIG. 5(g)) demonstrated alteration of convergence to the midline and extension along the AP axis consistent with a PCP defect, although the AP extension defect was more pronounced in the mks3 compared to the tmem216 morphant.

Recent work has implicated the tetraspanin TSPAN12 in the regulation of Norrin signaling by the Wnt receptor Frizzled-4 and coreceptor LRP5[2]. Therefore, without being bound by a particular theory, it is believed that TMEM216, a novel tetraspan protein, forms a non-canonical Wnt receptor-coreceptor complex with Meckelin. Our data supports a role for both proteins in mediating PCP signaling through the RhoA pathway to cause actin cytoskeleton rearrangements, although whether Rho functions upstream or downstream of Dvl1 remains to be determined. In apical regions of the cell, such actin reorganization would be an essential step before the centrosome/basal body could dock correctly and initiate ciliogenesis. The identification of mutations in TMEM216 as a cause of JSRD and MKS therefore further emphasizes the interrelationship between cell polarity, cellular morphogenesis and signal transduction pathways.

TMEM216 Nucleic Acids

In alternative embodiments, the invention provides isolated, synthetic or recombinant nucleic acids comprising a nucleotide sequence of a TMEM216 nucleic acid variant, as described herein. In alternative embodiments, nucleotide sequences of the invention comprise at least about 12, 13, 14, 15, 16, 17, 18, 19, 20, 21, 22, 23, 24, 25, 26, 27, 28, 29, 30, 31, 32, 33, 34, or 35 or more contiguous nucleotides spanning the locus in one of the mutant TMEM216 genomic DNAs having one of the nucleotide variations encoding TMEM216 protein, including R73L, R73H and R73C mutations, or the locus in one of the mutant TMEM216 mRNAs, or cDNAs prepared therefrom, expressed from the mutant TMEM216 genomic DNAs expressing one of the TMEM216 protein mutations, including R73L, R73H and R73C mutations. In alternative embodiments, nucleic acid molecules of the invention can be in a form of recombinant, synthetic, DNA, RNA, and/or a chimeric or hybrid thereof, and can be in any physical structure or form, e.g., including a single-strand or double-strand or in the form of a triple helix.

In one embodiment, isolated, synthetic or recombinant nucleic acids of the invention have a sequence of SEQ ID NO:2, and (complete) complements thereof. In alternative embodiments, nucleotide sequences of the invention comprise TMEM216 nucleic acid variants that are mutant TMEM216 genomic DNAs (or equivalents) expressing one of the TMEM216 protein variants including R73L, R73H and R73C mutations, or those mutant TMEM216 mRNAs derived from the mutant TMEM216 genomic DNAs, expressing one of the TMEM216 protein variants including R73L, R73H and R73C mutations, or cDNAs derived from such mRNAs. In alternative embodiments, nucleotide sequences of the invention comprise TMEM216 genomic DNAs, cDNAs and/or mRNAs (e.g., as isolated, synthetic or recombinant forms) having a full-length sequence (i.e., including the entire coding regions and, in the case of genomic DNAs, optionally introns, promoter, and other regulatory sequences) or partial sequence (i.e., a portion of the full-length sequence).

In one embodiment, isolated, synthetic or recombinant nucleic acids of the invention comprise a TMEM216 nucleic acid as an oligonucleotide, primer or probe comprising a contiguous span of the nucleotide sequence of a mutant TMEM216 sequence (either genomic DNA or cDNA or mRNA sequence), as described herein, and spanning a cDNA locus resulting in the expression of one of the TMEM216 protein variants, including the R73L, R73H and R73C mutations.

In alternative embodiments, an oligonucleotide, primer or probe contains (comprises or consists of) at least about 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, to about 80, 90, or 100 or more nucleotides, and alternatively from about 30 to about 50 or more nucleotides. Exemplary TMEM216 nucleic acid sequences of the invention are found in Supplemental Table 1 below.

In one embodiment, the oligonucleotides, primers and probes are specific to a TMEM216 nucleic acid variant of the invention. In alternative embodiments, nucleic acids of the invention comprise sequence variations as described in Table 1 above.

In alternative embodiments, they selectively hybridize, under stringent conditions generally recognized in the art, to a TMEM216 nucleic acid variant of the invention, but do not substantially hybridize to a reference TMEM216 nucleic acid sequence under stringent conditions. Such oligonucleotides will be useful in hybridization-based methods, or alternatively amplification-based methods, for detecting the nucleotide variants of the invention as described in detail below. A skilled artisan would recognize various sufficiently stringent conditions that enable the oligonucleotides of the invention to differentiate between a reference TMEM216 gene sequence and an isolated TMEM216 nucleic acid variant of the invention. For example, in one embodiment, sufficiently stringent condition comprises the hybridization conditions comprising: hybridization overnight in a solution containing (comprising) about 50% formamide, 5×SSC, pH 7.6, 5×Denhardt's solution, 10%° dextran sulfate, and 20 microgramiml denatured, sheared salmon sperm DNA. The hybridization filters can be washed in 0.1×SSC at about 65° C.

The oligonucleotide primers or probes of the invention can have a detectable marker selected from, e.g., radioisotopes, fluorescent compounds, enzymes, or enzyme cofactors operably linked to the oligonucleotide. The primers, probes and oligonucleotide sequences of the invention are useful in genotyping and haplotyping as will be apparent from the description below.

In another embodiment, TMEM216 nucleic acids are provided having 100, 200, 300, 400 or 500 nucleotides or basepairs, which contain the TMEM216 variant nucleotide or basepair sequences provided by SEQ ID NO: 3 wherein the variations are provided above in Table 1, and/or the complements thereof. Such nucleic acids can be DNA or RNA, and single-stranded or double-stranded.

In alternative embodiments, any nucleic acid molecules containing or comprising a sequence according to SEQ ID NO:3 and having at least one of the variations provided in Table 1 above fall within the scope of this invention. For example, a hybrid nucleic acid molecule of the invention can have a sequence according to SEQ ID NO:3 and having at least one of the variations provided in Table 1, above operably linked to a non-TMEM216 sequence such that the hybrid nucleic acid encodes a hybrid protein having a mutant TMEM216 peptide sequence.

In alternative embodiments, the invention provides plasmids, vectors, expression constructs and the like containing (having contained therein) one of the nucleic acid molecules of the invention. In alternative embodiments, the plasmids, vectors, expression constructs and the like are employed to express or amplify a nucleic acid molecule of the invention that is contained in the vector construct. In alternative embodiments, the plasmids, vectors, expression constructs and the like are used in expressing a polypeptide encoded by a nucleic acid molecule of the invention that is contained in the vector construct. In alternative embodiments, plasmids, vectors, expression constructs and the like include or comprise a promoter operably linked to an isolated nucleic acid molecule (e.g., a full-length sequence or 32/85 a fragment thereof in the 5' to 3' direction or in the reverse direction for the purpose of producing antisense nucleic acids), an origin of DNA replication for the replication of the plasmids, vectors etc. in host cells and a replication origin for the amplification of the vectors in, e.g., $E.\ coli$, and selection marker(s) for selecting and maintaining only those host cells harboring the vectors.

In alternative embodiments, plasmids, vectors, expression constructs and the like comprise inducible elements which function to control the expression of the isolated gene sequence. In alternative embodiments, plasmids, vectors, expression constructs and the like comprise other regulatory sequences such as transcriptional termination sequences and translation regulation sequences (e.g., Shine-Dalgarno sequence). An epitope tag coding sequence for detection and/or purification of the encoded polypeptide can also be incorporated into the vector construct. Exemplary epitope tags include, but are not limited to, influenza virus hemagglutinin (HA), Simian Virus 5 (V5), polyhistidine (6×His), c-myc, lacZ, GST, and the like. In alternative embodiments, proteins of the invention can comprise epitope tags or polyhistidine tags, which can be easily detected and/or purified with Ni affinity columns, while specific antibodies to many epitope tags are generally commercially available.

In alternative embodiments, plasmids, vectors, expression constructs and the like are introduced into the host cells or organisms by any techniques known in the art, e.g., by direct DNA transformation, microinjection, electroporation, viral infection, lipofection, biolystics (gene gun), and the like. The plasmids, vectors, expression constructs and the like can be maintained in host cells in an extrachromosomal state, i.e., as self-replicating plasmids or viruses. Alternatively, plasmids, vectors, expression constructs and the like can be integrated into chromosomes of the host cells by conventional techniques such as selection of stable cell lines or site-specific recombination. Plasmids, vectors, expression constructs and the like can be designed to be suitable for expression in various host cells, including but not limited to bacteria, yeast cells, plant cells, insect cells, and mammalian and human cells. A skilled artisan will recognize that the designs of the plasmids, vectors, expression constructs and the like can vary with the host used.

In alternative embodiments, a nucleic acid of the invention, e.g., a TMEM216 nucleic acid, is incorporated in an array, a microchip or microarray, or other similar (equivalent) structures. In alternative embodiments the microarray allows rapid genotyping and/or haplotyping in a large scale. In alternative embodiments, in the arrays or microchips, a large number of different nucleic acids are attached or immobilized in an array on a solid support, e.g., a silicon chip or glass slide. Target nucleic acid sequences to be analyzed can be contacted with the immobilized nucleic acids on the microchip. See Lipshutz et al., Biotechniques, 19:442-447 (1995); Chee et al., Science, 274:610-614 (1996); Kozal et al., Nat. Med. 2:753-759 (1996); Hacia et al., Nat. Genet., 14:441-447 (1996); Saiki et al., Proc. Natl. Acad. Sci. USA, 86:6230-6234 (1989), Gingeras et al., Genome Res., 8:435-448 (1998). The microchip technologies combined with computerized analysis tools allow large-scale high throughput screening. See, e.g., U.S. Pat. No. 5,925,525 to Fodor et al; Wilgenbus et al., J. Mol. Med., 77:761-786 (1999); Graber et al., Curr. Opin. Biotechnol., 9:14-18 (1998); Hacia et al., Nat. Genet., 14:441-447 (1996); Shoemaker et al., Nat. Genet., 14:450-456 (1996); DeRisi et al., Nat. Genet., 14:457-460 (1996); Chee et al., Nat. Genet., 14:610-614 (1996). Lockhart et al., Nat. Genet., 14:675-680 (1996); Drobyshev et al., Gene, 188:45-52 (1997).

In alternative embodiments, a microarray is provided comprising one or a plurality of the nucleic acids of the invention such that one, several or all of the nucleotide identities at each of the genetic variant sites disclosed in Table 1 can be determined in one single microarray.

TMEM216 Polypeptides

In alternative embodiments, the invention provides isolated, synthetic or recombinant polypeptides having an amino acid sequence of a TMEM216 protein variant, as described herein. In alternative embodiments the amino acid sequence is a contiguous sequence of at least about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, or 148 amino acids of SEQ ID NO:1 comprising one or more of the variations provided in Table 1 above. In alternative embodiments, the amino acid sequence can also be a contiguous sequence of at least 3, 4, 5. 6, 7, 8, 9, 10, 12, 13, 14, 15, 16, 17, 18, 19, 20, 21, 22, 23, 24, 25, 26, 27, 28, 29, or 30 or more amino acids of SEQ ID NO:6 comprising one or more of the variations provided in Table 1 above. In alternative embodiments, the amino acid sequence can also be a contiguous sequence of at least 3, 4, 5, 6, 7, 8, 9, 10, 12, 13, 14, 15, 16, 17, 18, 19, 20, 21, 22, 23, 24, 25, 26, 27, 28, 29, 30, 31, 32, or 33 or more amino acids of SEQ ID NO:9 comprising one or more of the variations provided in Table 1 above. In alternative embodiments, the amino acid sequence can also be a contiguous sequence of at least 3, 4, 5, 6, 7, 8, 9, 10, 12, 13, 14, 15, 16, 17, 18, 19, 20, 21, 22, 23, 24, or 25 or more amino acids of SEQ ID NO: 12 comprising one or more of the variations provided in Table 1 above.

In alternative embodiments, the invention provides isolated TMEM216 protein variants, as described herein, that can be initially isolated from a patient having a variation provided in Table 1 above. In alternative embodiments, TMEM216 protein variants of the invention also include other amino acid variants, such as those created as a result of single nucleotide polymorphisms in the coding sequence of the TMEM216 gene.

In alternative embodiments, hybrid proteins of the invention can have one or more or all of the above-described mutant TMEM216 amino acid sequences and a non-TMEM216 amino acid sequence.

In alternative embodiments, nucleic acids and polypeptides of the invention can be prepared using techniques generally known in the field of protein biochemistry and molecular biology. See e.g., Sambrook et al., Molecular Cloning: A Laboratory Manual, 2nd ed., Cold Spring Harbor Laboratory, Cold Spring Harbor, N.Y., 1989.

Antibodies

In alternative embodiments, the invention also provides antibodies selectively immunoreactive with a protein or peptide of the invention, e.g., a TMEM216 protein variant.

In alternative embodiments, the term "antibody" encompasses both monoclonal and polyclonal antibodies that fall within any antibody classes, e.g., IgG. IgM, IgA, etc. The term "antibody" also includes antibody fragments including, but not limited to, Fab and F(ab')$_2$, conjugates of such fragments, and single-chain antibodies that can be made in accordance with U.S. Pat. No. 4,704,692, which is incorporated herein by reference.

In alternative embodiments the phrase "selectively immunoreactive with an isolated TMEM216 protein variant of the invention" means that the immunoreactivity of the antibody of the invention with a TMEM216 protein variant of the invention is substantially or distinguishably higher than that with a TMEM216 protein heretofore known in the art (e.g., a wild type TMEM216 protein). For example, in one embodiment, the binding of an antibody of the invention to a protein of the invention is readily distinguishable from the binding of the antibody to a TMEM216 protein known in the art (e.g., a wild type TMEM216 protein), based on e.g., the strength of the binding affinities. In alternative embodiments, the binding constant differs by a magnitude of at least 2 fold, or at least 5 fold, or at least 10 fold, or at least 100 fold.

In alternative embodiments, to make the antibody, a TMEM216 protein variant of the invention, or a suitable fragment thereof, can be used to immunize an animal. The TMEM216 protein variant can be made by any methods known in the art, e.g., by recombinant expression or chemical synthesis. In alternative embodiments, a mutant TMEM216 protein fragment having an amino acid sequence selected from SEQ ID NOs: 1, 6, 9 or 12, wherein the sequence comprises a variation provided in Table 1 above, can also be used. In alternative embodiments, the mutant TMEM216 protein fragment consists of less than 100 amino acids, or less than 50 amino acids, or less than 25 amino acids. As a result, a greater portion of the total antibodies are selectively immunoreactive with a TMEM216 protein variant of the invention. Techniques for immunizing animals for the purpose of making polyclonal antibodies are generally known in the art. See Harlow and Lane, Antibodies: A Laboratory Manual, Cold Spring Harbor Laboratory, Cold Spring Harbor, N.Y., 1988. A carrier may be necessary to increase the immunogenicity of the polypeptide. Suitable carriers known in the art include, but are not limited to, liposome, macromolecular protein or polysaccharide, or combination thereof. Preferably, the carrier has a molecular weight in the range of about 10,000 to 1,000,000. The polypeptide may also be administered along with an adjuvant, e.g., complete Freund's adjuvant.

In alternative embodiments, antibodies of the invention are synthetic or monoclonal. Such monoclonal antibodies may be developed using any conventional techniques known in the art. For example, the popular hybridoma method disclosed in Kohler and Milstein, Nature, 256:495-497 (1975); see e.g., U.S. Pat. No. 4,376,110. In alternative embodiments, B-lymphocytes producing a polyclonal antibody against a protein variant of the invention can be fused with myeloma cells to generate a library of hybridoma clones. The hybridoma population is then screened for antigen binding specificity and also for immunoglobulin class (isotype). In this manner, pure hybridoma clones producing specific homogenous antibodies can be selected. See e.g., Harlow and Lane. Antibodies: A Laboratory Manual, Cold Spring Harbor Press, 1988. Alternatively, other techniques known in the art may also be used to prepare monoclonal antibodies, which include but are not limited to the EBV hybridoma technique, the human N-cell hybridoma technique, and the trioma technique.

In alternative embodiments, antibodies of the invention, e.g., those selectively immunoreactive with a protein of the invention, may also be recombinantly or synthetically produced. In alternative embodiments, cDNAs prepared by PCR amplification from activated B-lymphocytes or hybridomas may be cloned into an expression vector to form a cDNA library, which is then introduced into a host cell for recombinant expression. The cDNA encoding a specific desired protein may then be isolated from the library. The isolated cDNA can be introduced into a suitable host cell for the expression of the protein. In alternative embodiments recombinant techniques are used to recombinantly produce specific native antibodies, hybrid antibodies capable of simultaneous reaction with more than one antigen, chimeric antibodies (e.g., the constant and variable regions are derived from different sources), univalent antibodies which comprise one heavy and light chain pair coupled with the Fc region of a third (heavy) chain, Fab proteins, and the like. See U.S. Pat. No. 4,816,567; European Patent Publication No. 0088994; Munro, Nature, 312:597 (1984); Morrison, Science, 229:1202 (1985); Oi et al., BioTechniques, 4:214 (1986); and Wood et al., Nature, 314:446-449 (1985), all of which are incorporated herein by reference. Antibody fragments such as Fv fragments, single-chain Fv fragments (scFv). Fab' fragments, and F(ab').sub.2 fragments can also be recombinantly produced by methods disclosed in, e.g., U.S. Pat. No. 4,946,778; Skerra & Pluckthun, Science, 240:1038-1041 (1988); Better et al., Science, 240:1041-1043 (1988); and Bird, et al., Science, 242:423-426 (1988).

In alternative embodiments, antibodies of the invention are partially or fully humanized antibodies. For this purpose, any methods known in the art may be used. For example, partially humanized chimeric antibodies having V regions derived from the tumor-specific mouse monoclonal antibody, but human C regions are disclosed in Morrison and Oi, Adv. Immunol., 44:65-92 (1989). In alternative embodiments, fully humanized antibodies can be made using transgenic non-human animals. For example, transgenic non-human animals such as transgenic mice can be produced in which endogenous immunoglobulin genes are suppressed or deleted, while heterologous antibodies are encoded entirely by exogenous immunoglobulin genes, preferably human immunoglobulin genes, recombinantly introduced into the genome. See e.g., U.S. Pat. Nos. 5,530,101; 5,545,806; 6,075,181; PCT Publication No. WO 94/02602; Green et. al., Nat. Genetics, 7: 13-21 (1994); and Lonberg et al., Nature 368: 856-859 (1994), all of which are incorporated herein by reference. The transgenic non-human host animal may be immunized with suitable antigens such as a protein of the invention to illicit specific immune response thus producing humanized antibodies.

In alternative embodiments, cell lines producing specific humanized antibodies are derived from the immunized transgenic non-human animals. For example, mature B-lymphocytes obtained from a transgenic animal producing humanized antibodies can be fused to myeloma cells and the resulting hybridoma clones may be selected for specific humanized antibodies with desired binding specificities. In alternative embodiments, cDNAs may be extracted from mature B-lymphocytes and used in establishing a library that is subsequently screened for clones encoding humanized antibodies with desired binding specificities. In addition, antibodies may also be produced in transgenic plants containing recombinant nucleic acids encoding antibodies.

In alternative embodiments, the invention provides arrays, microarrays, protein microchips or macroarrays having (1) a protein or antibody of the invention, e.g., a TMEM216 protein variant of the invention or a fragment thereof, e.g., comprising an amino acid sequence according to SEQ ID NO: 1, SEQ ID NO:6, SEQ ID NO:9 or SEQ ID NO: 12, and/or having a variation as provided herein, e.g., in Table 1 above, and any combination of these protein variants; and/or (2) an antibody selectively immunoreactive with a protein of the invention, e.g., a TMEM216 protein variant of the invention.

In alternative embodiments, the invention provides arrays, microarrays, protein microchips or macroarrays for proteomics research and/or protein-based detection and diagnosis of diseases. In alternative embodiments the arrays, microarrays, protein microchips or macroarrays of the invention (e.g., protein microarrays of the invention) are useful in a variety of applications including, e.g., high throughput screening for compounds capable of modulating the activities of a polypeptide of the invention, e.g., a TMEM216 protein variant of the invention. In alternative embodiments, protein or nucleic acid arrays, microarrays, microchips or macroarrays are also useful in detecting a polypeptide or nucleic acid of the invention, e.g., a mutant TMEM216 protein of the invention, and thus can be used in determining a predisposition to, or the presence of, e.g., Joubert Syndrome and Related Disorders (JSRD) and Meckel Syndrome (MKS) in patients, particularly in the Ashkenazi Jewish population.

In alternative embodiments, the arrays, microarrays, microchips or macroarrays of the invention are prepared by a number of methods known in the art. An exemplary method is disclosed in e.g., MacBeath and Schreiber, Science, 289:1760-1763 (2000). For example, glass microscope slides are treated with an aldehyde-containing silane reagent (SuperAldehyde Substrates purchased from TeleChem International, Cupertino, Calif.). Nanoliter volumes of protein samples in a phosphate-buffered saline with 40% glycerol are then spotted onto the treated slides using a high-precision contact-printing robot. After incubation, the slides are immersed in a bovine serum albumin (BSA)-containing buffer to quench the unreacted aldehydes and to form a BSA layer which functions to prevent non-specific protein binding in subsequent applications of the microchip. Alternatively, as disclosed in MacBeath and Schreiber, proteins or protein complexes of the invention can be attached to a BSA-NHS slide by covalent linkages. BSA-NHS slides are fabricated by first attaching a molecular layer of BSA to the surface of glass slides and then activating the BSA with N,N'-disuccinimidyl carbonate. As a result, the amino groups of the lysine, aspartate, and glutamate residues on the BSA are activated and can form covalent urea or amide linkages with protein samples spotted on the slides. See MacBeath and Schreiber, Science, 289:1760-1763 (2000).

Another example of useful method for preparing an array, chip, microchip, e.g., a protein microchip, of the invention is disclosed in PCT Publication Nos. WO 00/4389A2 and WO 00/04382. For example, a substrate or chip base is covered with one or more layers of thin organic film to eliminate any surface defects, insulate proteins from the base materials, and to ensure a uniform protein array. Next, a plurality of protein-capturing agents (e.g., antibodies, peptides, etc.) are arrayed and attached to the base that is covered with the thin film. Proteins or protein complexes can then be bound to the capturing agents forming a protein microarray. The protein microchips are kept in flow chambers with an aqueous solution.

Another example of useful method for preparing an array, chip, microchip, e.g., a protein microchip, of the invention is disclosed in PCT Publication No. WO 99/36576. For example, a three-dimensional hydrophilic polymer matrix, i.e., a gel, is first deposited on a solid substrate such as a glass slide. The polymer matrix gel is capable of expanding or contracting and contains a coupling reagent that reacts with amine groups. Thus, proteins and protein complexes can be contacted with the matrix gel in an expanded aqueous and porous state to allow reactions between the amine groups on the protein or protein complexes with the coupling reagents thus immobilizing the proteins and protein complexes on the substrate. Thereafter, the gel is contracted to embed the attached proteins and protein complexes in the matrix gel.

Alternatively, nucleic acids, proteins and protein complexes of the invention can be incorporated into a commercially available protein microchip, e.g., the PROTEINCHIP™ (ProteinChip) system from Ciphergen Biosystems Inc., Palo Alto, Calif. The ProteinChip System comprises metal chips having a treated surface that interact with proteins. For example, a metal chip surface is coated with a silicon dioxide film. The molecules of interest such as proteins and protein complexes can then be attached covalently to the chip surface via a silane coupling agent.

An array, chip, microchip, e.g., a protein or nucleic acid microchip, of the invention can also be prepared with other methods known in the art, e.g., those disclosed in U.S. Pat. Nos. 6,087,102, 6,139,831, 6,087,103; PCT Publication Nos. WO 99/60156, WO 99/39210, WO 00/54046, WO 00/53625, WO 99/51773, WO 99/35289, WO 97/42507, WO 01/01142, WO 00/63694, WO 00/61806, WO 99/61148, WO 99/40434.

Genotyping and Genetic Prognosis and Diagnosis

In alternative embodiments, the invention provides compositions and, methods for determining or predicting a predisposition to, or the presence of, a ciliopathy (or any genetic disorder of a cellular cilia or cilia anchoring structure, basal body or ciliary function) in an individual, e.g., determining or predicting a predisposition to, or the presence of a Joubert Syndrome and Related Disorders (JSRD) and/or a Meckel Syndrome (MKS), e.g., in the Ashkenazi Jewish population.

In alternative embodiments the TMEM216 gene variations of (e.g., identified by) the invention are deleterious and predispose individuals having those sequences to e.g., a ciliopathy. Thus, in practicing a composition or method of the invention, the presence or absence of one or more of the TMEM216 variants of the invention can be detected in an individual. In one embodiment, using this information, one of skill can reasonably predict a predisposition to, or the presence of, one of those ciliopathies, e.g., e.g., a Joubert Syndrome and Related Disorders (JSRD) and/or Meckel Syndrome (MKS), particularly in the Ashkenazi Jewish population.

In alternative embodiments, any technique for detecting a genetic variant known in the art is used to practice a method or composition of this invention. The techniques can be nucleic acid-based or protein-based. In alternative embodiments, the techniques used are sufficiently sensitive so as to accurately detect the nucleotide or amino acid variations. In alternative embodiments, a probe is utilized which is labeled with a detectable marker. In alternative embodiments, any suitable marker known in the art can be used, including but not limited to, radioactive isotopes, fluorescent compounds, biotin which is detectable using streptavidin, enzymes (e.g., alkaline phosphatase), substrates of an enzyme, ligands and antibodies, etc. See Jablonski et al., Nucleic Acids Res., 14:6115-6128 (1986); Nguyen et al., Biotechniques, 13:116-123 (1992); Rigby et al., J. Mol. Biol., 113:237-251 (1977).

In alternative embodiments, a DNA-based detection method, a target DNA sample is used. For example, a sample containing a TMEM216 gene sequence should be obtained from the individual to be tested. Any tissue or cell sample containing the TMEM216 genomic DNA or mRNA, or a portion thereof, can be used. In alternative embodiments, a tissue sample containing cell nuclei and thus genomic DNA can be obtained from the individual. Blood samples can also be useful, except that only white blood cells and other lymphocytes have cell nuclei, while red blood cells are enucleated and contain mRNA. In alternative embodiments, mRNA is used, as it can be analyzed for the presence of nucleotide variants in its sequence or serve as template for cDNA synthesis. The tissue or cell samples can be analyzed directly without much processing. Alternatively, nucleic acids including the target TMEM216 nucleic acids can be extracted, purified, or amplified before they are subject to the various detecting procedures discussed below. Other than tissue or cell samples, cDNAs or genomic DNAs from a cDNA or genomic DNA library constructed using a tissue or cell sample obtained from the individual to be tested are also useful.

In alternative embodiments, to determine the presence or absence of a sequence of the invention, e.g., a mutation identified herein, a technique comprising sequencing a target TMEM216 genomic DNA or cDNA is used, e.g., where a the region spanning the genetic variation is detected and sequenced. In alternative embodiments any sequencing technique known in the art is used, e.g., the Sanger method and the Gilbert chemical method, or a pyrosequencing method (to monitor DNA synthesis in real time using a luminometric detection system). Pyrosequencing can be effective in analyzing genetic polymorphisms such as single-nucleotide polymorphisms; see e.g., Nordstrom et al., Biotechnol. Appl. Biochem., 31(2): 107-112 (2000); Ahmadian et al., Anal. Biochem., 280:103-110 (2000). For example, sequencing primers can be designed based on either mutant or wild-type TMEM216 gene intronic or exonic sequences such that the primers have the nucleotide sequence adjacent to a variation identified herein. In another example, PCR primers are designed based on either mutant or wild-type TMEM216 gene intronic or exonic sequences such that PCR amplification generates a TMEM216 DNA fragment spanning the deletion locus. Such primers can be those provided in Supplemental Table 1 below.

In alternative embodiments, restriction fragment length polymorphism (RFLP) methods are used; e.g., for the elimination and creation of restriction enzyme recognition sites. Digestion of the mutant TMEM216 genomic DNAs or cDNAs with appropriate restriction enzyme(s) can generate restriction fragment length patterns distinct from those generated from wild-type TMEM216 genomic DNA or cDNA. In alternative embodiments, variations in TMEM216 of the invention can be detected by RFLP. In alternative embodiments RFLP techniques known in the art to the invention are used.

In alternative embodiments, genomic DNA can be obtained from a patient sample and digested by appropriate restriction enzyme(s). Southern blot can be performed using a probe having a wild-type TMEM216 sequence that is missing from one or more of the TMEM216 genetic variants of the invention. Alternatively, probes specific to the mutant TMEM216 nucleic acids of the invention can also be used.

In alternative embodiments, the presence or absence of a sequence of the invention, e.g., a TMEM216 mutation of the invention, is detected using the amplification refractory mutation system (ARMS) technique. See e.g., European Patent No. 0,332,435; Newton et al., Nucleic Acids Res., 17:2503-2515 (1989); Fox et al., Br. J. Cancer, 77:1267-1274 (1998); Robertson et al., Eur. Respir. J., 12:477-482 (1998). In the ARMS method, a primer is synthesized matching the nucleotide sequence immediately 5' upstream from the locus being tested except that the 3'-end nucleotide which corresponds to the nucleotide at the locus is a predetermined nucleotide. For example, the 3'-end nucleotide can be the same as that in the mutated locus. The primer can be of any suitable length so long as it hybridizes to the target DNA under stringent conditions only when its 3'-end nucleotide matches the nucleotide at the locus being tested. Preferably the primer has at least 12 nucleotides, more preferably from about 18 to 50 nucleotides. If the individual tested has a mutation at the locus and the nucleotide therein matches the 3'-end nucleotide of the primer, then the primer can be further extended upon hybridizing to the target DNA template, and the primer can initiate a PCR amplification reaction in conjunction with another suitable PCR primer. In contrast, if the nucleotide at the locus is of wild type, then primer extension cannot be achieved. Various forms of ARMS techniques developed in the past few years can be used. See e.g., Gibson et al., Clin. Chem. 43:1336-1341 (1997). Thus, for example, primers having a sequence selected from SEQ ID NOs:42-47, 53-63, and 70-79 can all be useful in this technique.

In alternative embodiments, the mini sequencing or single nucleotide primer extension method (similar to the ARMS technique, which is based on the incorporation of a single nucleotide) is used. In alternative embodiments, an oligonucleotide primer matching the nucleotide sequence immediately 5' to the locus being tested is hybridized to the target DNA or mRNA in the presence of labeled dideoxyribonucleotides. A labeled nucleotide is incorporated or linked to the primer only when the dideoxyribonucleotides matches the nucleotide at the variant locus being detected. Thus, the identity of the nucleotide at the variant locus can be revealed based on the detection label attached to the incorporated dideoxyribonucleotides. See Syvanen et al., Genomics, 8:684-692 (1990); Shumaker et al., Hum. Mutat., 7:346-354 (1996); Chen et al., Genome Res., 10:549-547 (2000).

In alternative embodiments other techniques useful in the invention include "oligonucleotide ligation assays" (OLA), in which differentiation between a wild-type locus and a mutation is based on the ability of two oligonucleotides to anneal adjacent to each other on the target DNA molecule allowing the two oligonucleotides joined together by a DNA ligase. See Landergren et al., Science, 241:1077-1080 (1988); Chen et al, Genome Res., 8:549-556 (1998); Iannone et al., Cytometry, 39:131-140 (2000). Thus, for example, to detect a mutation at a particular locus in the TMEM216 gene, two oligonucleotides can be synthesized, one having the TMEM216 sequence just 5' upstream from the locus with its 3' end nucleotide being identical to the nucleotide in the mutant locus of the TMEM216 gene, the other having a nucleotide sequence matching the TMEM216 sequence immediately 3' downstream from the locus in the TMEM216 gene. The oligonucleotides can be labeled for the purpose of detection. Upon hybridizing to the target TMEM216 gene under a stringent conditions, the two oligonucleotides are subjected to ligation in the presence of a suitable ligase. The ligation of the two oligonucleotides would indicate that the target DNA has a nucleotide variant at the locus being detected. Thus, for example, oligonucleotides can be readily designed based on the loci present in mutant TMEM216 genomic DNA or cDNA sequences that are provided in Table 1 above.

In alternative embodiments screening for or detection of a genetic or sequence variation is accomplished by a variety of hybridization-based approaches. In alternative embodiments Allele-specific oligonucleotides are used, see e.g., Conner et al., Proc. Natl. Acad. Sci. USA, 80:278-282 (1983); Saiki et al, Proc. Natl. Acad. Sci. USA, 86:6230-6234 (1989). Oligonucleotide probes hybridizing specifically to a TMEM216 gene allele having a particular gene variant at a particular locus but not to other alleles can be designed by methods known in the art. The probes can have a length of, e.g., from about 10 to about 50 nucleotide bases. The target TMEM216 genomic DNA or cDNA and the oligonucleotide probe can be contacted with each other under conditions sufficiently stringent such that the genetic variant can be distinguished from the wild-type TMEM216 gene based on the presence or absence of hybridization. Examples of such probes and primers are provided in Supplemental Table 1 below. The probe can be labeled to provide detection signals. Alternatively, the allele-specific oligonucleotide probe can be used as a PCR amplification primer in an "allele-specific PCR" and the presence or absence of a PCR product of the expected length would indicate the presence or absence of a particular genetic variant. In alternative embodiments, oligos having a sequence selected from those provided in Supplemental Table 1 below can be used.

In alternative embodiments, mass spectrometry is used, e.g., see Graber et al., Curr. Opin. Biotechnol., 9:14-18 (1998). For example, in the primer oligo base extension (PROBE™) method, a target nucleic acid is immobilized to a solid-phase support. A primer is annealed to the target immediately 5' upstream from the locus to be analyzed. Primer extension is carried out in the presence of a selected mixture of deoxyribonucleotides and dideoxyribonucleotides. The resulting mixture of newly extended primers is then analyzed by MALDI-TOF. See e.g., Monforte et al., Nat. Med., 3:360-362 (1997). In another example, primers can be designed based on either mutant or wild-type TMEM216 gene intronic or exonic sequences such that the primers have the nucleotide sequences adjacent to and flanking a locus identified in accordance with the invention. PCR amplification on a patient sample is carried out using the primers. Mass spectrometry is then performed on the PCR product.

In alternative embodiments, a microchip or microarray technologies is used to practice a detection method of the invention. For example, in microchips, a large number of different oligonucleotide probes are immobilized in an array on a substrate or carrier, e.g., a silicon chip or glass slide. Target nucleic acid sequences to be analyzed can be contacted with the immobilized oligonucleotide probes on the microchip. See Lipshutz et al., Biotechniques, 19:442-447 (1995); Chee et al., Science, 274:610-614 (1996); Kozal et al., Nat. Med. 2:753-759 (1996); Hacia et al., Nat. Genet., 14:441-447 (1996); Saiki et al., Proc. Natl. Acad. Sci. USA, 86:6230-6234 (1989); Gingeras et al., Genome Res., 8:435-448 (1998). Alternatively, the multiple target nucleic acid sequences to be studied are fixed onto a substrate and an array of probes is contacted with the immobilized target sequences. See Drmanac et al., Nat. Biotechnol., 16:54-58 (1998). Numerous microchip technologies have been developed incorporating one or more of the above described techniques for detecting mutations particularly SNPs. The microchip technologies combined with computerized analysis tools allow fast screening in a large scale. In alternative embodiments, adaptations of microchip technologies are used, see, e.g., U.S. Pat. No. 5,925,525 to Fodor et al; Wilgenbus et al., J. Mol. Med., 77:761-786 (1999); Graber et al., Curr. Opin. Biotechnol., 9:14-18 (1998); Hacia et al., Nat. Genet., 14:441-447 (1996); Shoemaker et al., Nat. Genet., 14:450-456 (1996); DeRisi et al., Nat. Genet., 14:457-460 (1996); Chee et al., Nat. Genet., 14:610-614 (1996); Lockhart et al., Nat. Genet., 14:675-680 (1996); Drobyshev et al., Gene, 188:45-52 (1997).

In alternative embodiments, it may or may not be necessary to amplify a target nucleic acid, e.g., an RNA or a DNA, e.g., a TMEM216 genomic DNA or cDNA sequence to e.g., increase the number of target DNA molecules, depending on the detection techniques used. For example, most PCR-based techniques combine the amplification of a portion of the target and the detection of mutations. In alternative embodiments, any PCR amplification technique known in the art is used, e.g., as disclosed in U.S. Pat. Nos. 4,683,195 and 4,800,159. For non-PCR-based detection techniques, if necessary, the amplification can be achieved by, e.g., in vivo plasmid multiplication, or by purifying the target DNA from a large amount of tissue or cell samples. See generally, Sambrook et al., Molecular Cloning: A Laboratory Manual, 2nd ed., Cold Spring Harbor Laboratory, Cold Spring Harbor, N.Y., 1989. However, even with scarce samples, many sensitive techniques have been developed in which genetic variations can be detected without having to amplify the target DNA in the sample. For example, techniques have been developed that amplify the signal as opposed to the target DNA by, e.g., employing branched DNA or dendrimers that can hybridize to the target DNA. The branched or dendrimer DNAs provide multiple hybridization sites for hybridization probes to attach thereto thus amplifying the detection signals. See Detmer et al., J. Clin. Microbiol., 34:901-907 (1996); Collins et al., Nucleic Acids Res., 25:2979-2984 (1997); Horn et al., Nucleic Acids Res., 25:4835-4841 (1997); Horn et al., Nucleic Acids Res., 25:4842-4849 (1997); Nilsen et al., J. Theor. Biol., 187:273-284 (1997).

In alternative embodiments, techniques that avoid amplification are used, e.g., surface-enhanced resonance Raman scattering (SERRS), fluorescence correlation spectroscopy, and single-molecule electrophoresis. In SERRS, a chromophore-nucleic acid conjugate is absorbed onto colloidal silver and is irradiated with laser light at a resonant frequency of the chromophore. See Graham et al., Anal. Chem., 69:4703-4707 (1997). The fluorescence correlation spectroscopy is based on the spatio-temporal correlations between fluctuating light signals and trapping single molecules in an electric field. See Eigen et al., Proc. Natl. Acad. Sci. USA. 91:5740-5747 (1994). In single-molecule electrophoresis, the electrophoretic velocity of a fluorescently tagged nucleic acid is determined by measuring the time required for the molecule to travel a predetermined distance between two laser beams. See Castro et al., Anal. Chem., 67:3181-3186 (1995). In alternative embodiments, the Invader assay and the rolling circle amplification technique are used: see e.g. Lyamichev et al., Nat. Biotechnol., 17:292-296 (1999); Lizardi et al., Nature Genetics, 19:225-232 (1998).

In alternative embodiments, allele-specific oligonucleotides (ASO) are used in in situ hybridization using tissues or cells as samples. The oligonucleotide probes which can hybridize differentially with the wild-type gene sequence or the gene sequence harboring a mutation may be labeled with radioactive isotopes, fluorescence, or other detectable markers. In situ hybridization techniques are well known in the art and their adaptation to the invention for detecting the presence or absence of a genetic variant in the TMEM216 gene of a particular individual should be apparent to a skilled artisan apprised of this disclosure.

In alternative embodiments protein-based detection techniques are used, e.g., when a genetic variant causes an amino acid substitution or deletion or insertions that affects the protein primary, secondary or tertiary structure. To detect the amino acid variations, protein sequencing techniques may be used. For example, a TMEM216 protein or fragment thereof can be synthesized by recombinant expression using a TMEM216 DNA fragment isolated from an individual to be tested. In alternative embodiments, a TMEM216 cDNA fragment of no more than 100 to 150 base pairs encompassing the polymorphic locus to be determined is used. The amino acid sequence of the peptide can then be determined by conventional protein sequencing methods. Alternatively, the recently developed HPLC-microscopy tandem mass spectrometry technique can be used for determining the amino acid sequence variations. In this technique, proteolytic digestion is performed on a protein, and the resulting peptide mixture is separated by reversed-phase chromatographic separation. Tandem mass spectrometry can be performed and the data collected therefrom is analyzed. See Gatlin et al., Anal. Chem., 72:757-763 (2000).

In alternative embodiments, other useful protein-based detection techniques include immunoaffinity assays based on antibodies selectively immunoreactive with mutant TMEM216 proteins according to the invention. Such antibodies may react specifically with epitopes comprising the polypeptide fragments spanning the junction regions of TMEM216 proteins that correspond to loci in the mutant TMEM216 mRNAs transcribed from the mutant TMEM216 genomic DNAs of the invention. Alternatively, such antibodies may react specifically with epitopes present on the novel TMEM216 protein variants provided in Table 1 above. Examples of identified epitopes are provided in the Examples section herein. Methods for producing such antibodies are described above in detail. Antibodies can be used to immunoprecipitate specific proteins from solution samples or to immunoblot proteins separated by, e.g., polyacrylamide gels. Immunocytochemical methods can also be used in detecting specific protein polymorphisms in tissues or cells. In alternative embodiments antibody-based techniques are used including, e.g., enzyme-linked immunosorbent assay (ELISA), radioimmunoassay (RIA), immunoradiometric assays (IRMA) and immunoenzymatic assays (IEMA), including sandwich assays using monoclonal or polyclonal antibodies. See e.g., U.S. Pat. Nos. 4,376,110 and 4,486,530, both of which are incorporated herein by reference.

In alternative embodiments the invention provide compositions and methods for genotyping a TMEM216 gene of an individual to determine, in the individual, the presence or absence of a TMEM216 genetic variant, e.g., as provided in Table 1 above.

In alternative embodiments, once the presence or absence of a TMEM216 genetic variant of the invention is determined, the result can be cast in a communicable form that can be communicated to the individual patient or physician. Such a form can vary and can be tangible or intangible. The result with regard to the presence or absence of a TMEM216 genetic variant of the invention in the individual tested can be embodied in descriptive statements, diagrams, photographs, charts, images or any other visual forms. For example, images of gel electrophoresis of PCR products can be used in explaining the results. In alternative embodiments diagrams showing where a variation occurs in an individual's TMEM216 gene are used in communicating the test results. The statements and visual forms can be recorded on a tangible media such as papers, computer readable media such as floppy disks, compact disks, etc., or on an intangible media, e.g., an electronic media in the form of e-mail, or on a preferably secured website on the internet or an intranet, etc. In alternative embodiments, the result with regard to the presence or absence of a TMEM216 genetic variant of the invention in the individual tested is recorded in a sound form and transmitted through any suitable media, e.g., analog or digital cable lines, fiber optic cables, etc., via telephone, facsimile, wireless mobile phone, internet phone and the like.

The invention also provides kits for practicing compositions and methods of the invention, e.g., the genotyping methods of the invention. The kits may include a carrier for the various components of the kit. The carrier can be a container or support, in the form of, e.g., bag, box, tube, rack, and is optionally compartmentalized. The carrier may define an enclosed confinement for safety purposes during shipment and storage. In alternative embodiments the kit also includes various components useful in detecting nucleotide or amino acid sequence of the invention, e.g., the TMEM216 variants of the invention, using e.g., any detection techniques.

In one embodiment, the detection kit includes one or more oligonucleotides useful in detecting nucleotide or amino acid sequence of the invention, e.g., the TMEM216 variants of the invention, e.g., the genomic variants in TMEM216 sequences of the invention. In alternative embodiments, the oligonucleotides are designed such that they are specific to a TMEM216 nucleic acid (variant) of the invention under stringent conditions. In alternative embodiments, the oligonucleotides are designed such that they can distinguish one genetic variant from another at a particular locus under predetermined stringent hybridization conditions. Examples of such oligonucleotides include nucleic acids having a sequence of the invention as described in Supplemental Table 1 below. In alternative embodiments, the oligonucleotides can be used in mutation-detecting techniques such as allele-specific oligonucleotides (ASO), allele-specific PCR. TAQMAN™ (TaqMan)-based quantitative PCR, chemiluminescence-based techniques, molecular beacons, and improvements or derivatives thereof, e.g., microchip technologies.

In another embodiment of this invention, the kit includes one or more oligonucleotides suitable for use in detecting techniques such as ARMS, oligonucleotide ligation assay (OLA), and the like. For example, the oligonucleotides in this embodiment include a TMEM216 gene sequence immediately 5' upstream from a locus to be analyzed. The 3' end nucleotide of the oligo is the first nucleotide on the 3' side of the locus. Examples of suitable oligos include, but are not limited to, those consisting of a sequence selected from those provided in Supplemental Table 1 below.

In alternative embodiments, oligonucleotides in a detection kit can be labeled with any suitable detection marker including but not limited to, radioactive isotopes, fluorophores, biotin, enzymes (e.g., alkaline phosphatase), enzyme substrates, ligands and antibodies, etc. See Jablonski et al., Nucleic Acids Res., 14:6115-6128 (1986); Nguyen et al., Biotechniques, 13:116-123 (1992); Rigby et al., J. Mol. Biol., 113:237-251 (1977). Alternatively, the oligonucleotides included in the kit are not labeled, and instead, one or more markers are provided in the kit so that users may label the oligonucleotides at the time of use.

In another embodiment of the invention, the detection kit contains one or more antibodies selectively immunoreactive with a protein of the invention, e.g., a TMEM216 protein (variant) of the invention. Methods for producing and using such antibodies have been described above in detail. In another embodiment other components are used in the detection technique and are included in a detection kit of this invention. Examples of such components include, but are not limited to, DNA polymerase, reverse transcriptase, deoxyribonucleotides, dideoxyribonucleotides other primers suitable for the amplification of a target DNA or mRNA sequence, RNase A, mutS protein, and the like. In addition, the detection kit preferably includes instructions on using the kit for detecting genetic variants in TMEM216 gene sequences, particularly the genetic variants of the invention.

Screening Assays

The invention provides compositions and methods for identifying compounds capable of modulating, e.g., enhancing or inhibiting, the activities of a protein of the invention, e.g., a TMEM216 protein (variant) of the invention. In alternative embodiments, these identified compounds are useful in treating or preventing symptoms associated with decreased TMEM216 protein activities, e.g., Joubert Syndrome and Related Disorders (JSRD) and other ciliopathies, including Meckel Syndrome (MKS), particularly in the Ashkenazi Jewish population. For this purpose, a mutant TMEM216 protein or fragment thereof containing a particular variation in accordance with the invention can be used in any of a variety of drug screening techniques. Drug screening can be performed as described herein or using well known techniques, such as those described in U.S. Pat. Nos. 5,800,998 and 5,891,628, both of which are incorporated herein by reference. The candidate therapeutic (the test) compounds may include, but are not limited to: proteins, small peptides or derivatives or mimetics thereof; non-peptide small molecules; carbohydrates; nucleic acids; lipids or fats; and analogs thereof. In another embodiments, the compounds are small organic molecules having a molecular weight of no greater than 10,000 dalton, more or less than 5,000 dalton.

In one embodiment of the invention, the screening method of the invention is based on binding affinities to screen for compounds capable of interacting with or binding to a TMEM216 protein variant. Compounds to be screened may be peptides or derivatives or mimetics thereof, or non-peptide small molecules. In alternative embodiments, commercially available combinatorial libraries of compounds or phage display libraries displaying random peptides are used. In alternative embodiments any screening techniques known in the art is used to practice the invention.

In alternative embodiments, the TMEM216 proteins of the invention (the TMEM216 variants are the putative drug target) can be prepared by any suitable methods, e.g., by recombinant expression, by synthetic methods, or by purification. In alternative embodiments, a polypeptide or fragment can be free in solution or can be immobilized on a solid support, e.g., in a protein microchip, or on a cell surface. In alternative embodiments, any techniques for immobilizing proteins on a solid support is used, e.g., example, PCT Publication WO 84/03564, which discloses synthesizing a large numbers of small peptide test compounds on a solid substrate, such as plastic pins or other surfaces. Alternatively, purified mutant TMEM216 protein, or fragments thereof, can be coated directly onto plates such as multi-well plates. Non-neutralizing antibodies, i.e., antibodies capable binding to the TMEM216 protein, or fragments thereof, that do not substantially affect its biological activities may also be used for immobilizing the TMEM216 protein, or fragments thereof, on a solid support.

In alternative embodiments, to affect the screening, test compounds can be contacted with the immobilized TMEM216 protein of the invention, or fragments thereof, to allow binding to occur and complexes to form under standard binding conditions. In alternative embodiments, either the drug target or test compounds are labeled with a detectable marker using well known labeling techniques. To identify binding compounds, one may measure the steady state or end-point formation of the drug target-test compound complexes, or kinetics for the formation thereof.

In alternative embodiments, a known ligand capable of binding to the drug target can be used in competitive binding assays. Complexes between the known ligand and the drug target can be formed and then contacted with test compounds. The ability of a test compound to interfere with the interaction between the drug target and the known ligand is measured using known techniques. One exemplary ligand is an antibody capable of specifically binding the drug target. In alternative embodiments, an antibody is used for identifying peptides that share one or more antigenic determinants of a TMEM216 protein of the invention, or fragments thereof, or for identifying antigenic determinants specific to a TMEM216 protein (variants) of the invention.

In another embodiment, a yeast two-hybrid system may be employed to screen for proteins or small peptides capable of interacting with a TMEM216 protein variant. For example, a battery of fusion proteins each containing a random small peptide fused to e.g., Gal 4 activation domain, can be co-expressed in yeast cells with a fusion protein having the Gal 4 binding domain fused to a TMEM216 protein variant. In this manner, small peptides capable of interacting with the TMEM216 protein variant can be identified. Alternatively, compounds can also be tested in a yeast two-hybrid system to determine their ability to inhibit the interaction between the TMEM216 protein variant and a known protein, which is known to interact with the TMEM216 protein or polypeptide or fragment thereof. One example of such proteins is an antibody specifically against the TMEM216 protein variant.

In alternative embodiments, yeast two-hybrid systems known in the art are used e.g., as disclosed in, e.g., Bartel et al., in: Cellular Interactions in Development: A Practical Approach, Oxford University Press, pp. 153-179 (1993); Fields and Song, Nature, 340:245-246 (1989); Chevray and Nathans, Proc. Natl. Acad. Sci. USA, 89:5789-5793 (1992); Lee et al., Science, 268:836-844 (1995); and U.S. Pat. Nos. 6,057,101, 6,051,381, and 5,525,490.

In alternative embodiments, the compounds thus identified can be further tested for activities, e.g., in stimulating the mutant TMEM216 biological activities, e.g., in ciliogenesis and in interacting with its known interacting partner proteins. In alternative embodiments, once an effective compound is identified, structural analogs or mimetics thereof can be produced based on rational drug design with the aim of improving drug efficacy and stability, and reducing side effects. Methods known in the art for rational drug design can be used in the invention. See, e.g., Hodgson et al., Bio/Technology, 9:19-21 (1991); U.S. Pat. Nos. 5,800,998 and 5,891,628, all of which are incorporated herein by reference. An example of rational drug design is the development of HIV protease inhibitors. See Erickson et al., Science, 249:527-533 (1990). In alternative embodiments, rational drug design is based on one or more compounds selectively binding to a mutant TMEM216 protein or a fragment thereof.

In one embodiment, the three-dimensional structure of, e.g., a TMEM216 protein variant, is determined by biophysical techniques such as X-ray crystallography, computer modeling, or both. In alternative embodiments, the structure of the complex between an effective compound and the mutant TMEM216 protein is determined, and the structural relationship between the compound and the protein is elucidated. In this manner, the moieties and the three-dimensional structure of a selected compound (from a screening method of the invention), e.g., a lead compound, critical to its binding to a TMEM216 protein of this invention are revealed. In alternative embodiments, analog compounds having similar moieties and structures are designed. In alternative embodiments, the three-dimensional structure of wild-type TMEM216 protein is deciphered and compared to that of a TMEM216 protein of the invention. In alternative embodiments, this will aid in designing compounds selectively interacting with a mutant TMEM216 protein.

In alternative embodiments, a selected peptide compound capable of binding the TMEM216 protein variant is analyzed by alanine scanning mutagenesis, e.g., as by Wells, et al., Methods Enzymol., 202:301-306 (1991). In this technique, an amino acid residue of the peptide is replaced by Alanine, and its effect on the peptide's binding affinity to the mutant TMEM216 protein is tested. Amino acid residues of the selected peptide are analyzed in this manner to determine the domains or residues of the peptide important to its binding to mutant TMEM216 protein. These residues or domains constituting the active region of the compound are known as its "pharmacophore". This information can be very helpful in rationally designing improved compounds. Once the pharmacophore has been elucidated, a structural model can be established by a modeling process which may include analyzing the physical properties of the pharmacophore such as stereochemistry, charge, bonding, and size using data from a range of sources, e.g., NMR analysis, x-ray diffraction data, alanine scanning, and spectroscopic techniques and the like. Various techniques including computational analysis, similarity mapping and the like can all be used in this modeling process. See e.g., Perry et al., in OSAR: Quantitative Structure-Activity Relationships in Drug Design, pp. 189-193, Alan R. Liss, Inc., 1989; Rotivinen et al., Acta Pharmaceutical Fennica, 97:159-166 (1988); Lewis et al., Proc. R. Soc. Lond., 236:125-140 (1989); McKinaly et al., Annu. Rev. Pharmacol. Toxiciol., 29:111-122 (1989). Commercial molecular modeling systems available from Polygen Corporation, Waltham, Mass., include the CHARMm program, which performs the energy minimization and molecular dynamics functions, and QUANTA program which performs the construction, graphic modeling and analysis of molecular structure. Such programs allow interactive construction, visualization and modification of molecules. Other computer modeling programs are also available from BioDesign, Inc. (Pasadena. Calif.), Hypercube, Inc. (Cambridge, Ontario), and Allelix, Inc. (Mississauga, Ontario, Canada).

In alternative embodiments, a template is formed based on the established model. Various compounds can then be designed by linking various chemical groups or moieties to the template. Various moieties of the template can also be replaced. In addition, in the case of a peptide lead compound, the peptide or mimetics thereof can be cyclized, e.g., by linking the N-terminus and C-terminus together, to increase its stability. These rationally designed compounds are further tested. In this manner, pharmacologically acceptable and stable compounds with improved efficacy and reduced side effect can be developed.

Cell and Animal Models

In alternative embodiments, the invention provides transduced or transfected cells, or cell lines, or non-human transgenic animals, comprising (e.g., carrying, or having contained therein) a nucleic acid or a polypeptide of this invention, e.g., a TMEM216 nucleic acid or TMEM216 protein variant of the invention. The cells, cell lines and/or non-human transgenic animals can be used as screening or model systems for studying ciliopathies and testing various therapeutic approaches in treating ciliopathies, e.g., JSRD and MKS.

In alternative embodiments, to establish the cell line, cells expressing a polypeptide of this invention, e.g., a mutant TMEM216 protein, is synthesized or cloned, or isolated from an individual carrying a TMEM216 genetic variant. The primary cells can be transformed or immortalized using techniques known in the art. Alternatively, normal cells expressing a wild-type TMEM216 protein or other type of genetic variants can be manipulated to replace the entire endogenous TMEM216 gene with a TMEM216 nucleic acid (variant) of the invention, or simply to introduce mutations into the endogenous TMEM216 gene. The genetically engineered cells can further be immortalized.

In alternative embodiments, non-human transgenic animals are used for screening or testing. A transgenic animal can be made by replacing its endogenous TMEM216 gene ortholog with a heterologous nucleic acid sequence of the invention (e.g., a human TMEM216 nucleic acid variant). Alternatively, deletions, insertions or substitutions can be introduced into the endogenous animal TMEM216 gene ortholog to simulate the TMEM216 of the invention. In alternative embodiments, any technique for making a non-human transgenic animal is used, e.g., as described in, e.g., Capecchi, et al., Science, 244:1288 (1989); Hasty et al., Nature, 350:243 (1991); Shinkai et al., Cell, 68:855 (1992); Mombaerts et al., Cell, 68:869 (1992); Philpott et al., Science, 256:1448 (1992); Snouwaert et al., Science, 257: 1083 (1992); Donehower et al., Nature, 356:215 (1992); Hogan et al., Manipulating the Mouse Embryo; A Laboratory Manual, 2nd edition, Cold Spring Harbor Laboratory Press, 1994; and U.S. Pat. Nos. 5,800,998, 5,891,628, and 4,873,191.

In alternative embodiments, these cells, cell lines and non-human transgenic animals are valuable tools for studying the mutant TMEM216 genes, and e.g., for testing in vivo the compounds identified in the in vitro or cell-based screening methods of this invention. Studying drug candidates in a suitable animal model before advancing them into human clinical trials is particularly important because not only can efficacy of the drug candidates can be confirmed in the model animal, but the toxicology profiles, side effects, and dosage ranges can also be determined. Such information is then used to guide human clinical trials.

Although the foregoing invention has been described in some detail by way of illustration and example for purposes of clarity of understanding, it will be obvious that certain changes and modifications may be practiced within the scope of the appended claims.

All publications mentioned in the specification are indicative of the level of those skilled in the art to which this invention pertains. All publications and patent applications are herein incorporated by reference to the same extent as if each individual publication or patent application was specifically and individually indicated to be incorporated by reference.

The invention will be further described with reference to the examples described herein; however, it is to be understood that the invention is not limited to such examples.

EXAMPLES

Aspects of the present teachings may be further understood in light of the following examples, which should not be construed as limiting the scope of the present teachings in any way.

Example 1—JSRD and MKS Studies

Research Subjects.

After obtaining informed consent from parents, we used standard methods to isolate genomic DNA from peripheral blood of the affected children and family members or from frozen fetal tissue or amniocytes. Experiments were done in accordance with local ethics committee recommendations. Pregnancies were terminated after genetic counseling, in accordance with local bioethics laws and guidelines. Chromosome analysis was performed for at least one fetus of each family. Informed consent for the use of DNA and tissue was obtained from all participating families and the studies were approved by the Ethics Boards of Leeds (East), Casa Sollievo della Sofferenza Hospital/CSS-Mendel Institute. Hôpital Necker-Enfants Malades, and UCSD.

Genetic Mapping.

To refine the MKS2/JBTS2 locus, the 10K Affymetrix SNP array was used to perform a total genome-wide search for linkage in 9 consanguineous families with MKS. Data was evaluated by performing multipoint linkage analysis using MERLIN software assuming a fully penetrant recessive model with a disease allele of frequency 0.001 and allowing for heterogeneity between families. Areas of homozygosity on chromosome 11 were confirmed by performing high-resolution haplotype analysis within the identified regions. Published microsatellite markers were used.

Mutation Screening.

Mutational screening of TMEM216 was performed by direct sequencing of the 6 coding exons and the adjacent intronic junctions in JSRD/MKS families showing potential linkage to the locus and all MKS cases. PCR products were treated with EXO-SAP IT™ (AP Biotech), and both strands were sequenced using a BIGDYE™ (BigDye) terminator cycle sequencing kit with an ABI3130™ automated sequencer (Applied Biosystems). To test for TMEM216 mutations in the cohort of 460 JSRD patients we applied the high resolution melting (HRM) technique 31 using a LIGHTCYCLER (LightCycler) 480™ (Roche Applied Science), with the same primers and optimized PCR conditions, see e.g., Supplemental Table 1, describing SEQ ID NO: 17; SEQ ID NO: 18; SEQ ID NO: 19; SEQ ID NO:20; SEQ ID NO:21; SEQ ID NO:22; SEQ ID NO:23; SEQ ID NO:24; SEQ ID NO:25; and SEQ ID NO:26, from top to bottom in Table 1:

Supplemental Table 1

| Primer | Sequence | Anneal |
| --- | --- | --- |
| TMEM216ex1F | GACCGTTATCGCTTAGGTCT | 56 |
| TMEM216ex1R | TAGGTCAAGCTCTGGGACA | |
| TMEM216ex3F | TAGACACCACCCATACGAG | 56 |
| TMEM216ex3R | TTGGTAGGAATTGGCTCTG | |
| TMEM216ex4F | TGGAAAGCTGAGAGTGATGT | 56 |
| TMEM216ex4R | TACCAGCTTGTCTCATAAGGA | |
| TMEM216ex5F | CATTCCATCACATCCCCAC | 56 |
| TMEM216ex5R | ATGAGAAATGGTCCCTCAGC | |
| TMEM216ex6F | GCTGCTCTCATTCACTGGTC | 56 |
| TMEM216ex6R | ACAGCCTTTCTCAGGACAAC | |

Parental samples were tested to overcome the limit of HRM in identifying homozygous changes. In case parental samples were not available, the proband's DNA was mixed with equal amount of DNA from a wild-type individual (1:1). Each sample showing abnormal melting profile underwent direct sequencing. Segregation of the identified mutations was investigated in all available family members. Constructs encoding wildtype or mutant TMEM216 were transfected into 293T cells in a ratio of 20:1 TMEM216:TK-βgal vector. Cells were lysed after 48 h and half of each sample was subjected to Western analysis by blotting with EGFP antibody (Covance MMS-118R 1:500) and the remainder subjected to β-gal assay to standardize transfection efficiency 32. Similar loading of each well was confirmed by blotting with α-tubulin (Sigma T9026 1:2000).

Founder Haplotype Analysis.

The region surrounding TMEM216 was saturated with 14 single nucleotide polymorphisms and 3 microsatellite markers in ten patients homozygous for the same p.R73L mutation. Estimation of the mutation age was calculated as reported 33.

Bioinformatics.

Genetic location is in accordance with the 2006 Human Genome Browser (UC Santa Cruz, The Regents of the University of California). The full length TMEM216 open reading frame is encoded in EST BI910875. The ciliary proteome was searched using web-based tools 13,14. RefSeq was accessed using the NCBI Internet, NCBI Bethesda, Md., National Library of Medicine (US), National Center for Biotechnology Information. Pfam is web-based and is supported e.g., by the Howard Hughes Medical Institute, Chevy Chase, Md.

Cloning.

Full-length TMEM216 was cloned into the pcDNA3.0 vector, and then shuttled into the mCherry- and EGFP-containing vectors. Mutations were introduced into TMEM216-pEGFP-N3 by QUICKCHANGE™ (Quick-Change) mutagenesis (Stratagene, San Diego Calif.). TMEM216 open reading frame was also cloned into pCS2+ vector in order to make RNA for injection into zebrafish embryos.

Cells and Antibodies.

Mouse inner medullary collecting duct (IMCD3), human hTERT-immortalized retinal pigmentary epithelial (hRPE), and human embryonic kidney (HEK293) cells were grown in Dulbecco's minimum essential medium (DMEM)/Ham's F12 supplemented with 10% fetal calf serum at 37° C./5% C02. Fibroblasts were immortalized with the hTERT system, and maintained in Fibroblast Growth Medium (Genlantis Inc., San Diego, Calif.) supplemented with 10% fetal calf serum and 0.2 mg/ml geneticin. Normal, undiseased control fibroblasts were gestationally-age matched to fibroblasts from MKS patients. Patient 186, a compound heterozygote for the MKS3'TMEM67 mutations [p.R217X]+[p.M261T], has been described previously 23. The following primary antibodies were used: mouse anti-GFP and rabbit A.V. peptide ("Living Colors", Clontech): mouse-anti-γ-tubulin, mouse anti-acetylated-tubulin (Sigma-Aldrich Co. Ltd.); mouse-anti-glutamylated tubulin (GT335) 34, rabbit-anti-γ-tubulin, rabbit-anti-Meckelin, mouse anti-β actin (Abcam Ltd.); mouse anti-filamin A (AbNova Inc.); mouse anti-Dvl1 (Santa Cruz Biotechnology Inc.); mouse anti-RhoA (Cytoskeleton Inc.); and anti-EFe4 (a gift from P. Robinson, Department of Ophthalmology & Neurosciences, University of Leeds, UK). Rabbit-anti-Meckelin C-terminus, raised against amino acids 982-995, has been described previously 18. Rabbit-anti-Meckelin N-terminus, raised against amino acids 100-113, has also been described 23. Secondary antibodies were Alexa-Fluor 488-Alexa-Fluor 594- and Alexa-Fluor 568-conjugated goat anti-mouse IgG and goat anti-rabbit IgG (Molecular Probes), and HRP-conjugated goat anti-mouse and goat anti-rabbit (Dako). Alexa-Fluor 488 and 633 phalloidin conjugate (Molecular Probes) was used to visualize F-actin.

Biochemical Assays.

Rabbit-anti-TMEM216 antiserum was raised against the peptide sequence NLCQRKMPLS (SEQ ID NO:27) or NLCQRKMPLSC (SEQ ID NO:28), comprising amino acids 81-90, by GenScript Inc. (Piscatawav, N.J., USA). Antiserum was precipitated with 50% [w/v] ammonium sulphate pH7.0 and affinity-purified essentially as described previously 35. Co-immunoprecipitation was performed essentially as described previously 35. Whole cell extracts (WCE) were prepared from confluent untransfected HEK293 cells, or IMCD3 cells that had been transiently transfected with 1.0 ug plasmid constructs in 90 mm tissue culture dishes, or scaled down as appropriate. WCE supernatants were processed for immunoprecipitation experiments by using 5 μg affinity-purified mouse anti-GFP ("Living Colors", Clontech Inc.), or 5 μg MAbs, or 5-10 μg purified IgG fractions from rabbit polyclonal antisera, coupled to protein G- and/or protein A-Sepharose beads (GE Healthcare UK Ltd.) Immunoprecipitations were performed in reduced salt incubation buffer (20 mM Tris, pH7.5, 25 mM NaCl, 2 mM EDTA, 0.5 mM EGTA, 0.02% [w/v] NaN3, 10% [v/v] glycerol, 10% [v/v] ethanol, 0.1% [v/v] protease inhibitor cocktail). For assessing Dvl1 phosphorylation status, extraction and wash buffers were supplemented with phosphatase inhibitor cocktail (Sigma).

In Situ Hybridization in Human Embryos.

Human embryos were collected from terminated pregnancies using the mefiprestone protocol in agreement with French bioethics laws (94-654 and 04-800). Embryos were fixed in 11% formaldehyde, 60% ethanol and 10% acetic acid, embedded in paraffin and sectioned at 5 μm. Primers were selected for RT-PCR amplification on RNA extracted from a whole C12 (4 w) embryo

```
F1:
                                         (SEQ ID NO: 29)
GGTGAGATTCCGGAGGTAAACG,

R4:
                                         (SEQ ID NO: 30)
CCAAGGTGAGCACCTCAAGT
``` used as template for generating the riboprobes. T7F/R and F/T7R primer combinations allowed the amplification of sense and antisense templates respectively, as described 36. Sections were hybridized with a Digoxygenin labeled probe at 70° C. overnight, and digoxygenin was detected with an anti-DIG-Fab' antibody (Roche) at 1:1000.

Immunofluorescence and Confocal Microscopy.

IMCD3 or human age-matched hTERT-immortalized fetal fibroblasts were seeded at 20×103 cells/well on glass coverslips in six-well plates and fixed in ice-cold methanol (5 minutes at 4° C.) or 2% paraformaldehyde (20 minutes at room-temp). For analysis of siRNA-treated cells, cells were extracted in 0.75% Triton X-100 in 100 mM PIPES pH 6.9, 2 mM EGTA, 1 mM MgSO4, 0.1 mM EDTA for 30 seconds and fixed in methanol at −20° C. for at least 10 minutes. Paraformaldehyde fixed cells were permeabilized with 0.1% Triton X-100. For immunofluorescence, cells were washed with PBS and blocked in 1% milk protein/PBS. Primary and secondary antibodies together with DAPI (2 mg/ml), were added in 1% milk protein/PBS each for an hour, with further PBS washes between each stage. Primary antibodies were used at the following dilutions: mouse anti-acetylated-tubulin (1:800); mouse-anti-glutamylated tubulin (GT335) (1:1000); rabbit-anti-γ-tubulin (1:500); rabbit-anti-Meckelin (1:50-1:250); rabbit anti-TMEM216 (1:200); mouse anti-filamin A (1:500); mouse-anti-RhoA (1:1000). Secondary antibodies and phalloidin conjugate were diluted 1:500, and DAPI was diluted 1:1000. Confocal images were obtained using a Nikon Eclipse TE2000-E system, controlled by EZC 1 3.50 (Nikon) software. Images were processed in Metamorph, and figures were assembled using Adobe Photoshop CS3.

Transfection and siRNA.

For transfection with plasmids, cells at 90% confluency were transfected using Lipofectamine 2000 (Invitrogen Inc.) according to the manufacturer's instructions. Cells were incubated for 24 to 72 hrs prior to lysis or immunostaining. For RNAi knockdown in IMCD3 cells, siRNA duplexes were designed against different regions of the mouse Tmem216 ("Stealth Select". Invitrogen Inc.) Sequences were as follows:

```
Tmem216 siRNA1:
                                         (SEQ ID NO: 31)
5'-GCU GCU GCU CUA UCU UGG CAU UGA A, Tmem216 siRNA2:
                                         (SEQ ID NO: 32)
5'-CCC UUG GCA UUA GUG UGG CCU UGA C, Tmem216 siRNA3:
                                         (SEQ ID NO: 33)
5'-CCC AUC CGC UAU GAU GGC UUC CUA U.
```

Semi-quantitative RT-PCR analysis demonstrated the effectiveness of the Tmem216 siRNA1 (FIG. 14). Mks3 siRNA reagents have been described previously (23). The medium or low GC nontargeting negative controls (Invitrogen) were used as scrambled siRNA controls. Irrelevant siRNA duplexes against Hhari were used as a second negative control (a gift from P. Robinson, Department of Ophthalmology & Neurosciences, University of Leeds, UK). Individual duplexes (20 nM) or siRNA pools (total 60 nM) were transfected into IMCD3 cells at 60-80% confluency using LIPOFECTAMINE 2000® RNAiMAX™ (Invitrogen Inc.) according to the manufacturer's instructions. The efficiency of siRNA transfections, as determined with BLOCK-iT® Fluorescent Oligo (Invitrogen Inc.), was greater than 60%. Further assays were carried out at 72 hours after transfection.

RhoA Activation Assay.

The activated GTP-bound isoform of RhoA was specifically assayed in pull-down assays using a GST fusion protein of the Rho effector rhotekin (Cytoskeleton Inc., CO, USA), using conditions recommended by the manufacturers. Cell lysates were processed as rapidly as possible at 4° C., and snap-frozen in liquid nitrogen. Total RhoA and pull-down protein was immunodetected on western blots using a proprietary anti-RhoA monoclonal antibody (Cytoskeleton Inc.) Rho activity was inhibited by treating cells with cell permeable exoenzyme-C3-transferase (Cytoskeleton Inc.) at 2 ug/ml for 5 hr under standard cell culture conditions. Results shown are representative of three separate experiments.

Identification of Ciliary Defect Phenotypes in Zebrafish.

To knockdown tmem216 in zebrafish, a translational blocking morpholino antisense oligonucleotides (MOs) (5'-GGTTGTCTTCCGTGGGCAGCCATGT-3') (SEQ ID NO:34) (Gene Tools, Philomath, Oreg.) or control was microinjected (4 ng/nl) into one-two cell stage embryos, obtained from natural spawning of wild-type (AB) zebrafish lines. The mRNA encoding full-length human TMEM216 was co-injected where indicated. Endogenous mks3 was suppressed with a splice-blocking MO described previously (3 ng/nl) 29. For assessment of gastrulation phenotypes, mid-somitic embryos were scored blind at 8 somites (live; 80-100 embryos/injection), or 10-11 somites (morphometric analyses). Embryos were fixed overnight in 4% PFA, hybridized in situ with DIG-labeled krox20, pax2, and myoD riboprobes according to standard protocols, and flat-mounted for imaging and analysis. At 3 days postfertilization, morphological phenotype of morphants were quantified under bright-field microscopy based upon ciliary defects (hydrocephalus, small brain, heart edema, and curved tail) or embryonic lethal phenotypes.

All publications, patents, patent applications, GenBank sequences and identifiers, and other references cited in this application are incorporated herein by reference in their entirety for all purposes to the same extent as if each individual publication, patent, patent application or other reference was specifically and individually indicated to be incorporated by reference in its entirety for all purposes. Publications incorporated herein by reference in their entirety include:

1. Hubner, K., Windoffer, R., Hutter, H. & Leube, R. E. Tetraspan vesicle membrane proteins: synthesis, subcellular localization, and functional properties. *Int Rev Cytol* 214, 103-59 (2002).
2. Junge, H. J. et al. TSPAN12 regulates retinal vascular development by promoting Norrin- but not Wnt-induced FZD4/beta-catenin signaling. *Cell* 139, 299-311 (2009).
3. Caplan, M. J., Kamsteeg, E. J. & Duffield, A. Tetraspan proteins: regulators of renal structure and function. *Curr Opin Nephrol Hypertens* 16, 353-8 (2007).

4. Lancaster, M. A. & Gleeson, J. G. The primary cilium as a cellular signaling center: lessons from disease. *Curr Opin Genet Dev* 19, 220-9 (2009).
5. Keeler, L. C. et al. Linkage analysis in families with Joubert syndrome plus oculo-renal involvement identifies the CORS2 locus on chromosome 11p12-q13.3. *Am J Hum Genet* 73, 656-62 (2003).
6. Valente, E. M. et al. Description, nomenclature, and mapping of a novel cerebello-renal syndrome with the molar tooth malformation. *Am J Hum Genet* 73, 663-70 (2003).
7. Valente, E. M. et al. Distinguishing the four genetic causes of Joubert syndrome-related disorders. *Ann Neurol* 57, 513-9 (2005).
Baala, L. et al. The Meckel-Gruber syndrome gene, MKS3, is mutated in Joubert syndrome. *Am J Hum Genet* 80, 186-94 (2007).
9. Baala, L. et al. Pleiotropic Effects of CEP290 (NPHP6) Mutations Extend to Meckel Syndrome. *Am J Hum Genet* 81, 170-9 (2007).
10. Delous, M. et al. The ciliary gene RPGRIP1L is mutated in cerebellooculo-renal syndrome (Joubert syndrome type B) and Meckel syndrome. *Nat Genet* 39, 875-81 (2007).
11. Mougou-Zerelli, S. et al. CC2D2A mutations in Meckel and Joubert syndromes indicate a genotype-phenotype correlation. *Hum Mutat* 30, 1574-82 (2009).
12. Roume, J. et al. A gene for Meckel syndrome maps to chromosome 1 q13. *Am J Hum Genet* 63, 1095-101 (1998).
13. Gherman, A., Davis, E. E. & Katsanis, N. The ciliary proteome database: an integrated community resource for the genetic and functional dissection of cilia. *Nat Genet* 38, 961-2 (2006).
14. Inglis, P. N., Boroevich, K. A. & Leroux, M. R. Piecing together a ciliome. *Trends Genet* 22, 491-500 (2006).
15. Smith. U. M. et al. The transmembrane protein meckelin (MKS3) is mutated in Meckel-Gruber syndrome and the wpk rat. *Nat Genet* 38, 191-6 (2006).
16. Khanna H. et al. A common allele in RPGRIP1L is a modifier of retinal degeneration in ciliopathies. *Nat Genet* 41, 739-45 (2009).
17. Viradi, V., Szabo, L. & Papp, Z. Syndrome of polydactyly, cleft lip/palate or lingual lump, and psychomotor retardation in endogamic gypsies. *J Med Genet* 17, 119-22. (1980).
18. Dawe, H. R. et al. The Meckel-Gruber Syndrome proteins MKS1 and meckelin interact and are required for primary cilium formation. *Hum Mol Genet* 16, 173-86 (2007).
19. Wallingford, J. B. et al. Dishevelled controls cell polarity during *Xenopus* gastrulation. *Nature* 405, 81-5 (2000).
20. Park, T. J., Haigo, S. L. & Wallingford, J. B. Ciliogenesis defects in embryos lacking inturned or fuzzy function are associated with failure of planar cell polarity and Hedgehog signaling. *Nat Genet* 38, 303-11 (2006).
21. Veeman, M. T., Axelrod, J. D. & Moon, R. T. A second canon. Functions and mechanisms of beta-catenin-independent Wnt signaling. *Dev Cell* 5, 367-77 (2003).
22. Winter, C. G. et al. *Drosophila* Rho-associated kinase (Drok) links Frizzledmediated planar cell polarity signaling to the actin cytoskeleton. *Cell* 105, 81-91 (2001).
23. Dawe, H. R et al. Nesprin-2 interacts with meckelin and mediates ciliogenesis via remodelling of the actin cytoskeleton. *J Cell Sci* 122, 2716-26 (2009).
24. Pan, J., You, Y., Huang, T. & Brody, S. L. RhoA-mediated apical actin enrichment is required for ciliogenesis and promoted by Foxj1. *J Cell Si* 120, 1868-76 (2007).
25. Park, T. J., Mitchell, B. J., Abitua, P. B., Kintner, C. & Wallingford, J. B. Dishevelled controls apical docking and planar polarization of basal bodies in ciliated epithelial cells. *Nat Genet* 40, 871-9 (2008).
26. Lang, P. et al. Protein kinase A phosphorylation of RhoA mediates the morphological and functional effects of cyclic AMP in cytotoxic lymphocytes. *EMBO J* 15, 510-9 (1996).
27. Dutcher, S. K. Elucidation of basal body and centriole functions in *Chlamydomonas reinhardtii*. *Traffic* 4, 443-51 (2003).
28. Corbit, K. C. et al. Kif3a constrains beta-catenin-dependent Wnt signaling through dual ciliary and non-ciliary mechanisms. *Nat Cell Biol* 10, 70-6 (2008).
29. Leitch, C. C. et al. Hypomorphic mutations in syndromic encephalocele genes are associated with Bardet-Biedl syndrome. *Nat Genet* 40, 443-8 (2008).
30. Badano, J. L. et al. Dissection of epistasis in oligogenic Bardet-Biedl syndrome. *Nature* 439, 326-30 (2006).
31. Wittwer, C. T. High-resolution DNA melting analysis: advancements and limitations. *Hum Mutat* 30, 857-9 (2009).
32. Lancaster, M. A. et al. Impaired Wnt-beta-catenin signaling disrupts adult renal homeostasis and leads to cystic kidney ciliopathy. *Nat Med* 15, 1046-54 (2009).
33. Budde, B. S. et al. tRNA splicing endonuclease mutations cause pontocerebellar hypoplasia. *Nat Genet* 40, 1113-8 (2008).
34. Wolff, A. et al. Distribution of glutamylated alpha and beta-tubulin in mouse tissues using a specific monoclonal antibody, GT335. *Eur J Cell Biol* 59, 425-32 (1992).
35. Johnson, C. A., Padget, K., Austin, C. A. & Turner. B. M. Deacetylase activity associates with topoisomerase II and is necessary for etoposide-induced apoptosis. *J Biol Chem* 276, 4539-42 (2001).
36. Trueba, S. S. et al. PAX8, TITF1, and FOXE1 gene expression patterns during human development: new insights into human thyroid development and thyroid dysgenesis-associated malformations. *J Clin Endocrinol Metab* 90, 455-62 (2005).

APPENDIX A

```
SEQ ID NO: 1-TMEM216 amino acid sequence (148 aa)
MLPRGLKMAP RGKRLSSTPL EILFFLNGWY NATYFLLELF IFLYKGVLLP YPTANLVLDV    60

VMLLLYLGIE VIRLFFGTKG NLCQRKMPLS ISVALTFPSA MMASYYLLLQ TYVLRLEAIM   120

NGILLFFCGS ELLLEVLTLA AFSSMDTI                                      148

SEQ ID NO: 2-TMEM216 EST (GenBank Accession No. BI910875.1)
ctgcagacga cggcgtcgtg ggtggtcacc gttatccctt aggtctggag aggggacatc    60
cgagcgaggg ccacttgcgg ccaggcccga gctcgtccag ctccgggtga ccacagagtg   120
```

APPENDIX A-continued

```
ccgcgggcgg gcagaggggc cggaaaccca ggccgcttcg tccctgtttc cggcagcgcc      180
gcgctgctcc gggagccgct gtggcagcgt atgctgccac ggggactgaa gatggcgccg      240
cgaggtaaac ggttgtcctc caccccgctg gaaatcctgt tctttctgaa cgggtggtat      300
aatgctacct atttcctgct ggaacttttc atatttctgt ataaaggtgt cctgctacca      360
tatccaacag ctaacctagt actggatgtg gtgatgctcc tcctttatct tggaattgaa      420
gtaattcgcc tgttttttgg tacaaaggga aacctctgcc agcgaaagat gccactcagt      480
attagcgtgg ccttgacctt cccatctgcc atgatggcct cctattacct gctgctgcag      540
acctacgtac tccgcctgga agccatcatg aatggcatct tgctcttctt ctgtggctca      600
gagcttttac ttgaggtgct caccttggct gctttctcca gtatggacac gatttgaagt      660
acagaatttc agccagcagc ccatcaggct gacaccacac atattgcttc tggtacttta      720
gccacaccag tgagaattgg tggggcaagt tgtcctgaga aaggctgtgt ggcttttctt      780
cagcacagac ctttgggcaa ggcaactcag cataaggccg tgggtaccat cttctaaaac      840
caggaccatc caggccaaga ga                                               862
```
SEQ ID NO: 3-Nucleotide sequence encoding 148 aa TMEM216 (SEQ ID NO: 1)
```
atgctgccac ggggactgaa gatggcgccg cgaggtaaac ggttgtgctc caccccgctg       60
gaaatcctgt tctttctgaa cgggtggtat aatgctacct atttcctgct ggaacttttc      120
atatttctgt ataaaggtgt cctgctacca tatccaacag ctaacctagt actggatgtg      180
gtgatgctcc tcctttatct tggaattgaa gtaattcgcc tgttttttgg tacaaaggga      240
aacctctgcc agcgaaagat gccactcagt attagcgtgg ccttgacctt cccatctgcc      300
atgatggcct cctattacct gctgctgcag acctacgtac tccgcctgga agccatcatg      360
aatggcatct tgctcttctt ctgtggctca gagcttttac ttgaggtgct caccttggct      420
gctttctcca gtatggacac gatttga                                          447
```
SEQ ID NO: 4-BC011010 mRNA
```
gtgggtggtc accgttatcc cttaggtctg gagagggac atccgagcga gggccacttg        60
cggccaggcc cgagctcgtc cagctccggg tgaccacaga gtgccgcggg cgggcagagg      120
ggccggaaac ccaggccgct tcgtccctgt ttccggcagc gccgcgctgc tccgggagcc      180
gctgtggcag cgtatgctgc acggggact gaagatggcg ccgcgaggtg agattccgga      240
ggtaaacggt tgtcctccac cccgctggaa atcctgttct ttctgaacgg tggtataat      300
gctacctatt tcctgctgga acttttcata tttctgtata aggtgtcct gctaccatat      360
ccaacagcta acctagtact ggatgtggtg atgctcctcc tttatcttgg aattgaagta      420
attcgcctgt tttttggtac aaagggaaac ctctgccagc gaaagatgcc actcagtatt      480
agcgtggcct tgaccttccc atctgccatg atggcctcct attacctgct gctgcaaacc      540
tacgtactcc gcctggaagc catcatgaat ggcatcttgc tcttcttctg tggctcagag      600
cttttacttg aggtgctcac cttggctgct tctccagta tggacacgat ttgaagtaca      660
gaatttcagc cagcagicca tcaggctgac accacacata tttgcttctg gtactttagc      720
cacaccagtg agaattggtg gggcaagttg tcctgagaaa ggctgtgtgg cttttcttca      780
gcacagacat ttgggcaagc aactcagcat aaggccagtg gtaccatctc tcaaaccag      840
gaccatcagc ccaagagact cttctacact ccagtatagg gaggggcaag gttattccca      900
tcctgcccct tctcagaacc agtccctgc tgacctcaag ttctcctcct tgatcaccgt      960
ggccagagca tctcgtgtgg accatctagg ctccttgggc ttcaagcagg acctgagcca     1020
catgctccct gtacgagctg tgctataccct gtcccacatg agcacggaga gcctcatgtt     1080
```

APPENDIX A-continued

```
ggtgggtttc cagagtgatg tgaaagcctc tcaccccaat cctcggagac tgagttccac    1140
aactttttta gtagctcata gtgttatttt tctactctct tcatgaaa                 1188

SEQ ID NO: 5-BC011010 nucleotide sequence encoding 30 aa (SEQ ID NO: 6)
atgctgccac ggggactgaa gatggcgccg cgaggtgaga ttccggagg aaacggttgt      60 cctccacccc gctggaaatc ctgttctttc tga                                  93

SEQ ID NO: 6-BC0110101, amino acid sequence (30 a.a.)
MLPRGLKMAP RGEIPEVNGC PPPRWKSCSF                                       30

SEQ ID NO: 7-cDNA clones (44)
gtgggtggtc accgttatcc cttaggtctg gagaggggac atccgagcga gggccacttg     60
cggccaggcc cgagctcgtc cagctccggg tgaccacaga gtgccgcggg cgggcagagg    120
ggccggaaac ccaggccgct tcgtccctgt ttccggcagc gccgcgctgc tccgggagcc    180
gctgtggcag cgtatgctgc cacggggact gaagatggcg ccgcgagcgt tagggacgtc    240
gcgcctccct ggtccaaagc cggcttccgc ggtcccgccc accctgggtg cctgaaggtc    300
tcaaggtgca cagctcaaat aaacgcacct ccttggctgg ccacttcta ggctggctca    360 ggtaaacggt tgtcctccac cccgctggaa atcctgttct ttctgaacgg tggtataat    420 gctacctatt tcctgctgga acttttcata tttctgtata aaggtgtcct gctaccatat    480
ccaacagcta acctagtact ggatgtggtg atgctcctcc tttatcttgg aattgaagta    540
attcgcctgt tttttggtac aaagggaaac ctctgccagc gaaagatgcc actcagtatt    600
agcgtggcct tgaccttccc atctgccatg atggcctcct attacctgct gctgcagacc    660
tacgtactcc gcctgaagc catcatgaat ggcatcttgc tcttcttctg tggctcagag    720
cttttacttg aggtgctcac cttggctgct ttctccagta tggacacgat ttgaagtaca    780
gaatttcagc cagcagccca tcaggctgac accacacata ttgcttctgg tactttagcc    840
acaccagtga gaattggtgg ggcaagttgt cctgagaaag gctgtgtggc ttttcttcag    900
cacagacatt tgggcaagca actcagcata aggccagtgg gtaccatctt ctaaaccagg    960
accatcagcc caagagactc ttctacactc cagtataggg aggggcaagg ttattcccat   1020
cctgcccctt ctcagaacca gtcccctgct gacctcaagt tctcctcctt gatcaccgtg   1080
gccagagcat ctcgtgtgga ccatctaggc tccttgggct tcaagcagga cctgagccac   1140
atgctccctg tacgagctgt gctataccta tcccacatga gcacggagag cctcatgttg   1200
gtgggtttcc agagtgatgt gaaagcctct caccccaatc ctcggagact gagttccaca   1260
acttttttag tagctcatag tgttattttt ctactctctt catgaaa                 1307

SEQ ID NO: 8-cDNA clone 44 nucleotide sequencing encoding 33 aa (SEQ ID NO: 9)
atgctgccac ggggactgaa gatggcgccg cgagcgttag gacgtcgcg cctccctggt      60 ccaaagccgg cttccgcggt cccgccacc ctgggtgcct ga                        102

SEQ ID NO: 9-Amino acid sequence of cDNA clone 44
MLPRGIKMAP RALGTSRLPG PKPASAVPPT LGA                                   33

SEQ ID NO: 10-cDNA clones (28)
gtggctggtc accgttatcc cttcctgggt gcctgaaggt ctcaaggtgc acagctcaaa     60
taaacgcaga tccttggctg gccacttcct aggctggctc aggtaaacgg ttgtcctcca   120
ccccgctgga atcctgttc tttctgaacg gtggtataa tgctacctat ttcctgctgg    180
aacttttcat atttctgtat aaaggtgtcc tgctaccata tccaacagct aacctagtac   240
tggatgtggt gatgctcctc ctttatcttg gaattgaagt aattcgcctg ttttttggaa   300
aagcagacca tttggagatg actccatggg ctgtgtctga caggtacaaa gggaaacctc   360
tgccagcgaa agatgccact cagtattagc gtggccttga ccttcccatc tgccatgatg   420
```

APPENDIX A-continued

```
gcctcctatt acctgctgct gcagacctac gtactccgcc tggaagccat catgaatggc    480
atcttgctct tcttctgtgg ctcagagctt ttacttgagg tgctcacctt ggctgctttc    540
tccagtatgg acacgatttg aagtacagaa tttcagccag cagcccatca ggctgacacc    600
acacatattg cttctggtac tttagccaca ccagtgagaa ttggtggggc aagttgtcct    660
gagaaaggct gtgtggcttt tcttcagcac agacatttgg gcaagcaact cagcataagg    720
ccagtgggta ccatcttcta aaccaggacc atcagcccaa gagactcttc tacactccag    780
tatagggagg ggcaaggtta ttcccatcct gcccttctc agaaccagtc cctgctgac     840 ctcaagttct cctccttgat caccgtggcc agagcatctc gtgtggacca tctaggctcc    900
ttgggcttca agcaggacct gagccacatg ctccctgtac gagctgtgct atacctgtcc    960
cacatgagca cggagagcct catgttggtg ggtttccaga gtgatgtgaa agcctctcac   1020
cccaatcctc ggagactgag ttccacaact tttttagtag ctcatagtgt tatttttcta   1080
ctctcttcat gaaa                                                     1094
```

SEQ ID NO: 11-cDNA clone 28 nucleotide sequence encoding 25 aa (SEQ ID NO: 12)
```
atgctaccta tttcctgctg gaactttca tatttctgta taaaggtgtc ctgctaccat     60
atccaacagc taacctag                                                  78
```

SEQ ID NO: 12-cDNA clone 28 amino acid sequence
MLPISCWNES YECIKVSCYH IQQLT                                          25

SEQ ID NO: 13 and SEQ ID NO: 14: PCR primers located in TMEM216 exon 4
forward: GATGTGGTGATGCTCCTCCT (SEQ ID NO: 13)
and reverse: CCAAGGTGAGCACCTCAAGT (SEQ ID NO: 14).

TMEM216 WT sequence is SEQ ID NO: 15:
GTACAAA GGGAAACCTC TGCCAGCGAA AGATGCCACT CAGTATTAGC GTGGCCTTGA CCTTC TMEM216 Mut sequence is SEQ ID NO: 16:
GAAAA GCAGA CCATT TGGAG ATGAC TCCAT GGGCT GTGTC TGACA GCTAC AAAGG GAAAC CT

SEQ ID NO: 17 CACCGTTATCCCTTAGGTCT

SEQ ID NO: 18 TAGGTCAAGCTCTGGGACA

SEQ ID NO: 19 TAGACACCAACCCATACGAG

SEQ ID NO: 20 TTGGTAGGAATTGGCTCTG

SEQ ID NO: 21 TGGAAAGCTGAGACTGATGT

SEQ ID NO: 22 TACCAGCTTGTCTCATAAGGA

SEQ ID NO: 23 CATTCCATCACATCTCCCAC

SEQ ID NO: 24 ATGAGAAATGGTCCCTCAGC

SEQ ID NO: 25 GCTGCTCTCATTCACTGGTC

SEQ ID NO: 26 ACAGCCTTTCTCAGGACAAC

A number of embodiments of the invention have been described. Nevertheless, it will be understood that various modifications may be made without departing from the spirit and scope of the invention. Accordingly, other embodiments are within the scope of the following claims.

What is claimed is:

1. A method of detecting or identifying a variant Transmembrane Protein 216 (TMEM216) gene in an individual, comprising:
   (i) providing a sample from an individual, wherein the sample comprises a nucleic acid;
   (ii) contacting the TMEM216 encoding nucleic acid in the sample with a probe capable of hybridizing to a TMEM216 encoding nucleic acid sequence variant, wherein the TMEM216 encoding nucleic acid sequence variant encodes an amino acid variation of SEQ ID NO:1 selected from the group consisting of L133X, L114R, G77A, R85X, wherein the probe is labeled with a detectable marker, and wherein the selectable marker is selected from the group consisting of a radioisotope, fluorescent compound, biotin, enzyme, enzyme co-factor, ligand, and antibody, and
   (iii) detecting hybridization of the probe with the TMEM216 encoding nucleic acid sequence variant, wherein detection of hybridization detects or identifies the presence of a variant TMEM216 gene in the sample from the individual.

2. The method of claim 1, wherein the amino acid variation comprises L133X.

3. The method of claim 1, wherein the amino acid variation comprises s L114R.

4. The method of claim 1, wherein the amino acid variation comprises G77A.

5. The method of claim 1, wherein the amino acid variation comprises R85X.

6. The method of claim 1, wherein the method comprises isolating the TMEM216-encoding nucleic acid from the sample before detecting hybridization of the probe with the TMEM216-encoding nucleic acid sequence variant.

7. The method of claim 1, wherein the TMEM216-encoding nucleic acid comprises a TMEM216 RNA, a TMEM216 DNA, a TMEM216 cDNA or a TMEM216 genomic DNA.

8. The method of claim 1, wherein the method further comprises analyzing or sequencing the TMEM216-encoding nucleic acid by performing a technique comprising: a polymerase chain reaction (PCR) assay; a chain-terminator method; an emulsion PCR assay; an oligonucleotide ligation and detection method; a high-throughput sequencing; a DNA nanoball sequencing; a Massive Parallel Signature Sequencing (MPSS); a dye-terminator sequencing procedure; a reversible dye-terminator sequencing procedure; an ion semiconductor sequencing; a parallelized version of pyrosequencing; or, any combination thereof.

9. The method of claim 8, wherein the technique comprises a PCR assay.

10. The method of claim 8, wherein the technique comprises high-throughput sequencing.

11. The method of claim 1, wherein the enzyme is an alkaline phosphatase.

* * * * *